US010669256B2

(12) United States Patent
Sheng et al.

(10) Patent No.: US 10,669,256 B2
(45) Date of Patent: Jun. 2, 2020

(54) CRYSTALLINE FORMS OF LASMIDITAN, PREPARATION METHODS, PHARMACEUTICAL COMPOSITIONS AND USES THEREOF

(71) Applicant: Hangzhou SoliPharma Co., Ltd., Hangzhou, Zhejiang (CN)

(72) Inventors: Xiaohong Sheng, Zhejiang (CN); Xiaoxia Sheng, Zhejiang (CN); Xiawei Jiang, Zhejiang (CN)

(73) Assignee: Hangzhou SoliPharma Co., Ltd., Hangzhou, Zhejang (CN)

( * ) Notice: Subject to any disclaimer, the term of this patent is extended or adjusted under 35 U.S.C. 154(b) by 0 days.

(21) Appl. No.: 16/318,055

(22) PCT Filed: Nov. 11, 2016

(86) PCT No.: PCT/CN2016/105405
§ 371 (c)(1),
(2) Date: Jan. 15, 2019

(87) PCT Pub. No.: WO2018/010345
PCT Pub. Date: Jan. 18, 2018

(65) Prior Publication Data
US 2019/0233393 A1      Aug. 1, 2019

(30) Foreign Application Priority Data

Jul. 15, 2016 (CN) .......................... 2016 1 0559448

(51) Int. Cl.
*C07D 401/06*     (2006.01)
*A61K 31/444*    (2006.01)
*A61P 25/06*      (2006.01)

(52) U.S. Cl.
CPC .......... *C07D 401/06* (2013.01); *A61K 31/444* (2013.01); *A61P 25/06* (2018.01); *C07B 2200/13* (2013.01)

(58) Field of Classification Search
CPC ..... C07D 401/06; A61K 31/444; A61P 25/06; C07B 2200/13
See application file for complete search history.

(56) References Cited

U.S. PATENT DOCUMENTS 7,423,050 B2 * 9/2008 Cohen .................. C07D 401/06
                                                             514/318
8,697,876 B2    4/2014 Carniaux et al.
2015/0376178 A1* 12/2015 Cohen .................. C07D 401/06
                                                             514/274

FOREIGN PATENT DOCUMENTS

CN         100352817 C  * 12/2007 .......... C07D 401/06
WO         WO 03/084949 A1   10/2003

OTHER PUBLICATIONS

Giamberardino, M.A., "Emerging drugs for migraine treatment." Expert opinion on emerging drugs 20.1 (2015): 137-147.*
Färkkilä, M., "Efficacy and tolerability of lasmiditan, an oral 5-HT1F receptor agonist, for the acute treatment of migraine: a phase 2 randomised, placebo-controlled, parallel-group, dose-ranging study." The Lancet Neurology 11.5 (2012): 405-413.*
CN-100352817-C; ProQuest English Machine Translation; accessed online Oct. 7, 2019; p. 1-84.*
International search report for United States Application No. PCT/CN2016/105405, State Intellectual Property Office of the P.R China, China, dated May 2, 2017.

* cited by examiner

*Primary Examiner* — John M Mauro
(74) *Attorney, Agent, or Firm* — Sterne Kessler Golstein & Fox PLLC

(57) ABSTRACT

The present invention relates to the crystalline forms of a 5-$HT_{1F}$ receptor agonist 2,4,6-trifluoro-N-[6-[(1-methyl-piperidin-4-yl)carbonyl]pyridin-2-yl]-benzene formamide (lasmiditan) and its hydrochloride. The crystalline forms of the present invention have advantages in crystallinity, hygroscopicity, morphology, crystal form stability, and chemical stability as compared with the known forms of lasmiditan and lasmiditan hydrochloride. The present invention also relates to processes for the preparation of the crystalline forms of lasmiditan and lasmiditan hydrochloride, pharmaceutical compositions thereof and their use in treating and/or preventing a patient's migraine and other diseases or conditions associated with 5-$HT_{1F}$ receptor dysfunction.

28 Claims, 24 Drawing Sheets

CRYSTALLINE FORMS OF LASMIDITAN, PREPARATION METHODS, PHARMACEUTICAL COMPOSITIONS AND USES THEREOF

FIELD OF THE INVENTION

The present invention relates to the technical field of crystallization in pharmaceutical chemistry. Specifically, the present invention relates to the crystalline forms of a 5-$HF_{1F}$ receptor agonist and its hydrochloride, preparation methods, pharmaceutical compositions and uses thereof. The receptor agonist is 2,4,6-trifluoro-N-[6-(1-methyl-piperidine-4-carbonyl)pyridin-2-yl]-benzamide (lasmiditan).

BACKGROUND

Lasmiditan, known as COL-144 or LY573144, is a 5-$HF_{1F}$ receptor agonist. It is used to inhibit plasma protein extravasation, treat or prevent migraine and other diseases or symptoms related to dysfunction of 5-$HF_{1F}$ receptor. The chemical name is 2,4,6-trifluoro-N-[6-(1-methyl-piperidine-4-carbonyl)pyridin-2-yl]-benzamide. Its chemical structural is shown in formula (I) below:

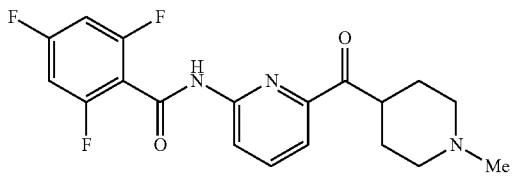

(I)

Lasmiditan is a novel selective and efficient 5-$HF_{1F}$ receptor agonist. It increases activation of 5-$HF_{1F}$ receptor, while avoiding vasoconstrictive activity, inhibiting plasma protein extravasation, for treating or preventing migraine and other diseases or symptoms related to dysfunction of 5-$HF_{1F}$ receptor. Included among these disorders are migraine (including hemicephalic neuralgia, headache related to vascular diseases, neurovascular headache), general pain, trigeminal neuralgia, anxiety, panic disorder, depression, post-traumatic syndrome, dementia and other diseases.

Patent document CN100352817C disclosed lasmiditan, lasmiditan semi-succinate and hydrochloride and their preparation methods, meanwhile disclosed their characterization data of mass spectra, $^1$H-NMR, $^{13}$C-NMR, as well as melting points. According to the study of the present inventor, lasmiditan, obtained by the preparation method of embodiments 17 and 21 in CN100352817C, is a light brown oil-like amorphous form, which has the disadvantages including unstable solid form, susceptible to moisture absorption and poor morphology.

The embodiment 8 of patent document CN100352817C reported the preparation method of lasmiditan hydrochloride, in which it was mentioned that lasmiditan free base was oil-like. Lasmiditan hydrochloride obtained by the preparation method of embodiment 8 in CN100352817 is a white amorphous form, which has the disadvantages including unstable solid form, susceptible to moisture absorption and poor morphology.

The embodiment 2 of patent document U.S. Pat. No. 8,697,876B2, disclosed the preparation method of lasmiditan semi-succinate intermediates, including lasmiditan and lasmiditan hydrochloride. According to the study of the inventor, lasmiditan, prepared according to U.S. Pat. No. 8,697,876B2 is also a light brown oily amorphous form; and lasmiditan hydrochloride is also a white amorphous form.

In view of the defects in the prior art, it is still necessary to discover more new crystalline forms of lasmiditan in this field, with improved properties to meet the strict requirements of pharmaceutical preparations on the morphology, stability and other physicochemical properties of active substances.

SUMMARY OF THE INVENTION

According to the defects in the prior art, the purpose of the present invention is mainly to provide new crystalline forms of lasmiditan and lasmiditan hydrochloride, and their preparation method, pharmaceutical compositions and uses thereof. The crystalline forms are stable crystalline solid with one or more improved properties, especially in the aspects of crystallinity, hygroscopicity, morphology, processability of the preparation, solid-state form stability and chemical stability.

According to the purpose of the invention, the first aspect of the invention is to provide a solid-state lasmiditan Form 1 and its preparation method.

The present invention provides lasmiditan Form 1 with its structure shown in the formula (I) below:

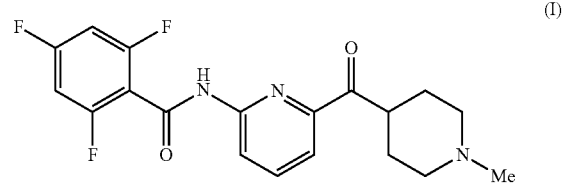 [SMILES: CN1CCC(C(=O)c2cccc(NC(=O)c3c(F)cc(F)cc3F)n2)CC1]

(I)

Measured using Cu-Kα radiation, the X-ray powder diffraction pattern of lasmiditan Form 1, expressed as 2θ angles, has the following characteristic peaks: 5.3±0.2°, 12.5±0.2°, 13.3±0.2°, 15.2±0.2°, 16.6±0.2° and 19.8±0.2°.

In a preferred embodiment of the present invention, the X-ray powder diffraction pattern of lasmiditan Form 1, expressed as 2θ angles, has the following characteristic peaks: 5.0±0.2°, 5.3±0.2°, 7.2±0.2°, 10.1±0.2°, 12.5±0.2°, 13.3±0.2°, 14.9±0.2°, 15.2±0.2°, 16.6±0.2°, 19.8±0.2°, 21.7±0.2° and 22.4±0.2°.

In a further preferred embodiment of the present invention, the X-ray powder diffraction pattern of lasmiditan Form 1, expressed as 2θ angles, has the following characteristic peaks and relative intensities:

| 2θ | Relative intensity % (I) |
|---|---|
| 5.0 ± 0.2° | 50.0 |
| 5.3 ± 0.2° | 96.2 |
| 7.2 ± 0.2° | 37.4 |
| 10.1 ± 0.2° | 52.9 |
| 10.7 ± 0.2° | 31.7 |
| 12.5 ± 0.2° | 62.0 |
| 13.3 ± 0.2° | 81.1 |
| 14.9 ± 0.2° | 77.3 |
| 15.2 ± 0.2° | 89.5 |
| 15.9 ± 0.2° | 46.2 |
| 16.6 ± 0.2° | 100.0 |
| 18.6 ± 0.2° | 39.9 |
| 19.8 ± 0.2° | 59.7 |

| 2θ | Relative intensity % (I) |
| --- | --- |
| 21.7 ± 0.2° | 26.1 |
| 22.4 ± 0.2° | 60.5 |
| 22.8 ± 0.2° | 46.2 |
| 24.0 ± 0.2° | 49.4 |
| 24.5 ± 0.2° | 29.0 |
| 25.5 ± 0.2° | 41.2. |

Non-restrictively, in one typical embodiment, the X-ray powder diffraction pattern of lasmiditan Form 1 is depicted in FIG. 6.

Non-restrictively, the DSC thermogram of lasmiditan Form 1 is depicted in FIG. 7.

Non-restrictively, the TGA thermogram of lasmiditan Form 1 is depicted in FIG. 8.

Non-restrictively, the PLM plot of lasmiditan Form 1 is shown in FIG. 9. The results show that the morphology of Form 1 is granular, and the particle size is relatively uniform, generally between 10 and 50 μm.

Non-restrictively, the isothermal sorption plot of lasmiditan Form 1 is shown in FIG. 10. The results show that the weight change of Form 1 is 0.1% between 0 to 80% RH.

Compared with the known lasmiditan amorphous form, lasmiditan Form 1 of the present invention has the following beneficial properties:

1) According to the XRPD pattern and PLM plot, lasmiditan Form 1 is a crystalline solid with high crystallinity and regular morphology.

2) According to the DVS isothermal sorption plot, the weight change of lasmiditan Form 1 is 0.1% between 20 to 80% RH, while the weight change of lasmiditan amorphous form in the same humidity range is 9.5%; therefore the lasmiditan Form 1 of the invention is less hygroscopic, and its hygroscopicity is much lower than that of the lasmiditan amorphous form.

3) According to Comparative Example 1, lasmiditan amorphous form began to crystallize after having been stored for 1 day, while lasmiditan Form 1 of the present invention remained unchanged after having been stored for 10 days, indicating that the lasmiditan Form 1 of the present invention has better solid-state form stability.

4) According to Comparative Example 2, the chemical purity of lasmiditan amorphous form decreased by more than 2% after 10 days in 40° C. dry conditions, while the chemical purity of lasmiditan Form 1 remained unchanged after having been stored for 10 days. Therefore, lasmiditan Form 1 of the present invention has higher chemical stability.

The above advantageous properties of lasmiditan Form 1 show that, compared to the known amorphous form, lasmiditan Form 1 of the present invention has many advantages and is more suitable to be used as the solid form of the active component in pharmaceutical preparations. The amorphous form is unstable and it is prone to crystallize under the influences of environmental factors such as temperature and humidity. Such instability may further affect the quality and stability of the pharmaceutical formulations. Lasmiditan Form 1 is crystalline, and its solid form stability is obviously better (than amorphous solids). Crystalline solids usually have better flowability and processing characteristics (processing such as filtrating, drying, weighing, screening, and so on), which are beneficial in improving the homogeneity of the pharmaceutical formulations. In addition, lasmiditan Form 1 has lower hygroscopicity, which may better guarantee the quality, safety and stability of the active ingredient, ensure the quality, safety and stability of lasmiditan formulation in its manufacturing and storage processes, avoid problems such as content uniformity issues of active ingredients and increase in impurities, and also avoid special and expensive packaging.

The present invention provides preparation methods of lasmiditan Form 1, which comprise any one of the following preparation methods:

1) dissolving lasmiditan in a mixed solvent to form a solution; and volatilizing the solution to dryness to obtain lasmiditan Form 1;

preferably, the mixed solvent is a mixture of water and a water-miscible organic solvent;

more preferably, the mixed solvent is water-methanol mixture, water-acetone mixture or water-acetonitrile mixture;

preferably, the mass to volume ratio of lasmiditan to the mixed solvent is from 50 to 500 mg: 1 mL, more preferably from 200 to 500 mg: 1 mL;

preferably, the volume percentage of water in the mixed solvent is from 1% to 10%, more preferably from 5% to 10%;

preferably, the volatilization is carried out at room temperature.

2) forming a suspension of lasmiditan in a solvent, stirring for crystallization; separating crystals and drying the crystals to obtain lasmiditan Form 1;

preferably, the solvent is selected from solvents containing water; more preferably, the solvent is ethanol-water mixture, tetrahydrofuran-water mixture or ethyl acetate saturated with water;

preferably, the volume percentage of water in the solvent is from 1% to 100%, more preferably from 80% to 100%;

preferably, the mass to volume ratio of lasmiditan to the solvent is from 10 to 1000 mg: 1 mL, more preferably from 100 to 1000 mg: 1 mL;

preferably, the stirring time is from 0.5 hours to 3 days, more preferably from 1 to 3 days;

preferably, the stirring is carried out at room temperature.

According to the purpose of the invention, the second aspect of the present invention is to provide a solid-state lasmiditan Form 2 and its preparation method.

Lasmiditan Form 2 of the present invention has the structural shown in formula (I) below:

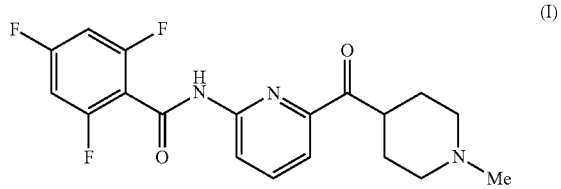 [SMILES: CN1CCC(C(=O)c2cccc(NC(=O)c3c(F)cc(F)cc3F)n2)CC1]

(I)

wherein using Cu-Kα radiation, the X-ray powder diffraction pattern of Form 2, expressed as 2θ angles, has the following characteristic peaks: 4.9±0.2°, 9.0±0.2°, 9.8±0.2°, 13.5±0.2°, 15.8±0.2° and 17.7±0.2°.

In a preferred embodiment of the present invention, the X-ray powder diffraction pattern of lasmiditan Form 2, expressed as 2θ angles, has the following characteristic peaks: 4.9±0.2°, 9.0±0.2°, 9.8±0.2°, 12.9±0.2°, 13.5±0.2°, 15.8±0.2°, 17.7±0.20, 18.5±0.2°, 19.7±0.20, 22.2±0.2°, 22.7±0.2° and 23.7±0.2°.

In a further preferred embodiment of the present invention, the X-ray powder diffraction pattern of lasmiditan Form 2, expressed as 2θ angles, has the following characteristic peaks and relative intensities:

| 2θ | Relative Intensity % (I) |
|---|---|
| 4.9 ± 0.2° | 60.9 |
| 9.0 ± 0.2° | 44.5 |
| 9.8 ± 0.2° | 49.7 |
| 12.9 ± 0.2° | 27.7 |
| 13.5 ± 0.2° | 100.0 |
| 14.9 ± 0.2° | 20.8 |
| 15.8 ± 0.2° | 77.1 |
| 17.7 ± 0.2° | 87.8 |
| 18.2 ± 0.2° | 37.9 |
| 18.5 ± 0.2° | 69.2 |
| 19.3 ± 0.2° | 18.7 |
| 19.7 ± 0.2° | 59.9 |
| 20.5 ± 0.2° | 34.7 |
| 21.7 ± 0.2° | 31.0 |
| 22.2 ± 0.2° | 55.5 |
| 22.7 ± 0.2° | 51.7 |
| 23.3 ± 0.2° | 24.6 |
| 23.7 ± 0.2° | 52.4 |
| 25.2 ± 0.2° | 28.1 |
| 26.8 ± 0.2° | 18.8. |

Non-restrictively, in one typical embodiment, the XRPD pattern of lasmiditan Form 2 is depicted in FIG. 11.

Non-restrictively, the DSC thermogram of lasmiditan Form 2 is depicted in FIG. 12.

Non-restrictively, the TGA thermogram of lasmiditan Form 2 is depicted in FIG. 13.

Non-restrictively, the PLM plot of lasmiditan Form 2 is shown in FIG. 14. The results show that the morphology of Form 2 is granular, and the particle size is relatively uniform, generally between 10 and 50 μm.

Non-restrictively, the isothermal sorption plot of lasmiditan Form 2 is depicted in FIG. 15. The results show that the weight change of Form 2 is 0.1% between 0 to 80% RH.

Compared with the known lasmiditan amorphous form, lasmiditan Form 2 of the present invention has the following beneficial properties:

1) According to the XRPD pattern and PLM plot, lasmiditan Form 2 is a crystalline solid with high crystallinity and regular morphology.

2) According to the DVS isothermal plot, the weight change of lasmiditan Form 2 is 0.1% between 20 to 80% RH, while the weight change of lasmiditan amorphous form is 9.5% in the same humidity range; therefore the lasmiditan Form 2 of the invention is less hygroscopic, and its hygroscopicity is much lower than that of lasmiditan amorphous form.

3) According to Comparative Example 1, lasmiditan amorphous form began to crystallize after having been stored for 1 day, while lasmiditan Form 2 of the present invention remained unchanged after having been stored for 10 days, indicating that the lasmiditan Form 2 of the present invention has better solid form stability.

4) According to Comparative Example 2, the chemical purity of lasmiditan amorphous form decreased by more than 2% after having been stored for 10 days in 40° C. dry conditions, while lasmiditan Form 2 remain unchanged. Therefore, lasmiditan Form 2 of the present invention has higher chemical stability.

The above advantageous properties of lasmiditan Form 2 show that, compared to the known amorphous form, lasmiditan Form 2 of the present invention has many advantages and is more suitable to be used as the solid form of the active ingredient in pharmaceutical formulations. The amorphous form is unstable and is prone to crystallize under the influences of environmental factors such as temperature and humidity. Such instability may further affect the quality and stability of the pharmaceutical formulations. Lasmiditan Form 2 is crystalline, and its solid-state form stability is obviously better (than amorphous solids). Crystalline solids usually have better flowability and processing characteristics (processing such as filtrating, drying, weighing, screening, and so on), which are beneficial in improving the homogeneity of the pharmaceutical formulations. In addition, Form 2 has lower hygroscopicity, which may better guarantee the quality, safety and stability of the active ingredient, ensure the quality, safety and stability of lasmiditan formulation in its manufacturing and storage processes, avoid problems such as content uniformity issues of active ingredients and increase in impurities, and also avoid special and expensive packaging.

The present invention provides a preparation method of lasmiditan Form 2, which includes the following steps:

forming a suspension of lasmiditan in a solvent, stirring the suspension for crystallization, separating crystals and drying the crystals obtain lasmiditan Form 2;

preferably, the solvent is selected from the group consisting of $C_4$ to $C_6$ ether, $C_3$ to $C_5$ ketone, $C_1$ to $C_4$ alcohol, $C_2$ to $C_6$ ester, and $C_6$ to $C_8$ alkane; more preferably, the solvent is methyl tert-butyl ether, acetone, isopropanol, ethyl acetate, n-heptane or a mixture thereof;

preferably, the mass to volume ratio of lasmiditan to the solvent is 10 to 1000 mg: 1 mL, more preferably 10 to 100 mg: 1 mL;

preferably, the stirring time is 1 to 7 days, more preferably 3 to 7 days;

preferably, the stirring is carried out at room temperature.

According to the purpose of the invention, the third aspect of the invention is to provide a solid-state lasmiditan Form 3 and its preparation method.

Lasmiditan Form 3 of the present invention has the structural shown in formula (I) below:

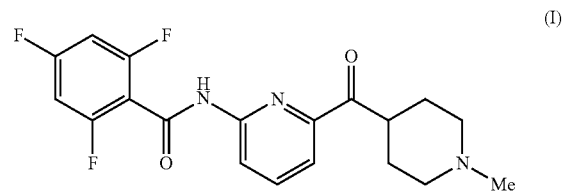 [SMILES: CN1CCC(C(=O)c2cccc(NC(=O)c3c(F)cc(F)cc3F)n2)CC1]

wherein using Cu-Kα radiation, the X-ray powder diffraction pattern of Form 3, expressed as 2θ angles, has the following characteristic peaks: 3.8±0.2°, 9.8±0.2°, 11.2±0.2°, 14.6±0.2°, 16.1±0.2° and 18.5±0.2°.

In a preferred embodiment of the present invention, the X-ray powder diffraction pattern of lasmiditan Form 3, expressed as 2θ angles, has the following characteristic peaks: 3.8±0.2°, 9.8±0.2°, 11.2±0.2°, 14.6±0.2°, 16.1±0.2°, 17.8±0.20, 18.5±0.2°, 19.6±0.2°, 20.7±0.20, 22.3±0.2°, 23.9±0.2° and 24.5±0.2°.

In a further preferred embodiment of the present invention, the X-ray powder diffraction pattern of lasmiditan Form 3, expressed as 2θ angles, has the following characteristic peaks and relative intensities:

| 2θ | Relative Intensity % (I) |
|---|---|
| 3.8 ± 0.2° | 100.0 |

-continued

| 2θ | Relative Intensity % (I) |
|---|---|
| 5.0 ± 0.2° | 5.3 |
| 7.5 ± 0.2° | 4.0 |
| 9.8 ± 0.2° | 10.2 |
| 11.2 ± 0.2° | 15.4 |
| 12.8 ± 0.2° | 4.6 |
| 13.6 ± 0.2° | 4.4 |
| 14.6 ± 0.2° | 12.4 |
| 16.1 ± 0.2° | 26.0 |
| 17.1 ± 0.2° | 4.9 |
| 17.8 ± 0.2° | 9.2 |
| 18.5 ± 0.2° | 23.0 |
| 18.9 ± 0.2° | 5.1 |
| 19.6 ± 0.2° | 11.6 |
| 20.7 ± 0.2° | 6.6 |
| 21.6 ± 0.2° | 5.5 |
| 22.3 ± 0.2° | 13.3 |
| 23.0 ± 0.2° | 8.5 |
| 23.9 ± 0.2° | 8.7 |
| 24.5 ± 0.2° | 16.5. |

Non-restrictively, in one typical embodiment, the XRPD pattern of lasmiditan Form 3 is shown in FIG. 39.

Non-restrictively, the DSC thermogram of lasmiditan Form 3 is depicted in FIG. 40.

Non-restrictively, the TGA thermogram of lasmiditan Form 3 is depicted in FIG. 41.

Non-restrictively, the PLM plot of lasmiditan Form 3 is depicted in FIG. 42.

Non-restrictively, the isothermal sorption plot of lasmiditan Form 3 is depicted in FIG. 43.

Compared with the known lasmiditan amorphous form, lasmiditan Form 3 of the present invention has the following beneficial properties:

1) According to the XRPD pattern and PLM plot, lasmiditan Form 3 is a crystalline solid with high crystallinity and regular morphology.

2) According to the DVS isothermal sorption plot, the weight change of lasmiditan Form 3 is 0.7% between 0 to 80% RH, while the weight change of lasmiditan amorphous form is 9.5% in the same humidity range; therefore lasmiditan Form 3 of the present invention is less hygroscopic, and its hygroscopicity is much lower than that of lasmiditan amorphous form.

3) According to Comparative Example 1, lasmiditan amorphous form began to crystallize after having been stored for 1 day, while lasmiditan Form 3 of the invention remained unchanged after having been stored for 10 days, indicating that the lasmiditan Form 3 of the present invention has better solid-state form stability.

4) According to Comparative Example 2, the chemical purity of lasmiditan amorphous form decreased by more than 2% after having been stored for 10 days in 40° C. dry conditions, while lasmiditan Form 3 remain unchanged after having been stored for 10 days. Therefore, Form 3 of the present invention has higher chemical stability.

The above advantageous properties of lasmiditan Form 3 show that, compared to the known amorphous form, lasmiditan Form 3 of the present invention has many advantages and is more suitable to be used as the solid form of the active ingredient in pharmaceutical formulations. The amorphous form is unstable and is prone to crystallize under the influences of environmental factors such as temperature and humidity. Such instability may further affect the quality and stability of the pharmaceutical formulations. Lasmiditan Form 3 as a crystalline solid, its solid-state form stability is obviously better. Crystalline solids usually have better flowability and processing characteristics (processing such as filtrating, drying, weighing, screening, and so on), which are beneficial in improving the homogeneity of the pharmaceutical formulations. In addition, Form 3 has lower hygroscopicity, which may better guarantee the quality, safety and stability of the active ingredient, ensure the quality, safety and stability of lasmiditan formulation in its manufacturing and storage processes, avoid problems such as content uniformity issues of active ingredients and increase in impurities, and also avoid special and expensive packaging.

The present invention provides preparation methods of lasmiditan Form 3, which comprise any one of the following preparation methods:

1) dissolving lasmiditan in a solvent to form a solution, then adding 1 to 10% (wt %) of polyethylene glycol 4000, applying ultrasound to facilitate dissolution, and volatilizing the solution to dryness to obtain lasmiditan Form 3;

preferably, the solvent is selected from a $C_1$ to $C_4$ alcohol; more preferably, the solvent is ethanol;

preferably, the mass ratio of lasmiditan to the solvent is 50 to 100 mg: 1 mL;

preferably, the volatilization process is carried out at 40° C.

2) dissolving Lasmiditan in a solvent to form a solution, and volatilizing the solution to dryness to obtain lasmiditan Form 3;

preferably, the solvent is selected from the group consisting of isopropyl ether, isopropyl acetate and toluene;

preferably, the mass to volume ratio of lasmiditan to solvent is 2 to 50 mg:1 mL;

preferably, the volatilization process is carried out at room temperature.

According to the purpose of the invention, the fourth aspect of the invention is to provide a solid-state lasmiditan hydrochloride Form A and its preparation method.

Lasmidita hydrochloride Form A having the structural shown in formula (II) below:

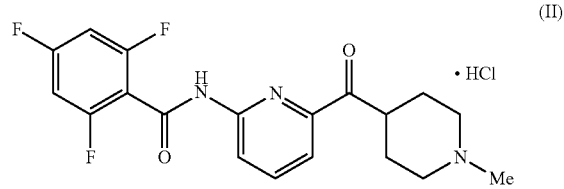

(II)

wherein using Cu-Kα radiation, the X-ray powder diffraction pattern of the Form A, expressed as 2θ angles, has the following characteristic peaks: 12.1±0.2°, 13.1±0.2°, 15.8±0.2°, 18.9±0.2°, 19.8±0.2° and 25.3±0.2°.

In a preferred embodiment of the present invention, the X-ray powder diffraction pattern of lasmiditan Form A, expressed as 2θ angles, has the following characteristic peaks: 9.3±0.2°, 12.1±0.2°, 13.1±0.2°, 15.8±0.2°, 18.9±0.2°, 19.8±0.2°, 21.0±0.20, 22.0±0.2°, 23.5±0.2°, 25.3±0.2°, 27.3±0.2° and 27.6±0.2°.

In a further preferred embodiment of the present invention, the X-ray powder diffraction pattern of lasmiditan hydrochloride Form A, expressed as 2θ angles, has the following characteristic peaks and relative intensities:

| 2θ | Relative Intensity % (I) |
|---|---|
| 9.3 ± 0.2° | 1.9 |

-continued

| 2θ | Relative Intensity % (I) |
|---|---|
| 12.1 ± 0.2° | 3.3 |
| 13.1 ± 0.2° | 11.3 |
| 15.8 ± 0.2° | 2.0 |
| 18.9 ± 0.2° | 100.0 |
| 19.8 ± 0.2° | 2.6 |
| 20.8 ± 0.2° | 2.5 |
| 21.0 ± 0.2° | 3.4 |
| 22.0 ± 0.2° | 1.9 |
| 23.5 ± 0.2° | 5.8 |
| 25.3 ± 0.2° | 11.7 |
| 25.8 ± 0.2° | 3.2 |
| 27.3 ± 0.2° | 3.6 |
| 27.6 ± 0.2° | 5.1. |

Non-restrictively, in one typical embodiment, the XRPD pattern of lasmiditan hydrochloride Form A is depicted in FIG. 22.

The DSC thermogram of lasmiditan hydrochloride Form A is depicted in FIG. 23.

The TGA thermogram of lasmiditan hydrochloride Form A is depicted in FIG. 24.

The PLM plot of lasmiditan hydrochloride Form A is depicted in FIG. 25.

The isothermal sorption plot of lasmiditan hydrochloride Form A is depicted in FIG. 26.

Compared with the known lasmiditan hydrochloride amorphous form, lasmiditan hydrochloride Form A of the present invention has the following beneficial properties:

1) According to the XRPD pattern and PLM plot, lasmiditan hydrochloride Form A is a crystal solid with high crystallinity and regular morphology;

2) According to the DVS isothermal plot, the weight change of lasmiditan hydrochloride Form A is 0.1% between 0 to 80% RH, while the weight change of lasmiditan hydrochloride amorphous form is 8.1% in the same humidity range, therefore the lasmiditan hydrochloride Form A of the present invention is less hygroscopic, and its hygroscopicity is much lower than that of lasmiditan hydrochloride amorphous form;

3) According to Comparative Example 1, lasmiditan hydrochloride amorphous form began to crystallize after having been stored for 1 day, while lasmiditan hydrochloride Form A of the present invention remained unchanged after having been stored for 10 days, indicating that the lasmiditan hydrochloride Form A of the present invention has better solid-state form stability;

4) According to Comparative Example 2, the chemical purity of lasmiditan hydrochloride amorphous form decreased by more than 1.5% after having been stored for 10 days in 40° C. dry conditions, while lasmiditan hydrochloride Form A remain unchanged after having been stored for 10 days. Therefore, lasmiditan hydrochloride Form A of the present invention has higher chemical stability.

The above advantageous properties of lasmiditan hydrochloride Form A of the present invention show that, compared to the known lasmiditan hydrochloride amorphous form, lasmiditan hydrochloride Form A of the present invention has many advantages and is more suitable to be used as the solid form of the active ingredient in pharmaceutical formulations. The amorphous form is unstable, and it is prone to crystallize under the influences of environmental factors such as temperature and humidity. Such instability may further affect the quality and stability of the pharmaceutical formulations. Lasmiditan hydrochloride Form A is crystalline, and its solid-state form stability is obviously better (than amorphpus solids). Crystalline solids usually have better flowability and processing characteristics (processing such as filtrating, drying, weighing, screening, and so on), which are beneficial in improving the homogeneity of the pharmaceutical formulations. In addition, lasmiditan hydrochloride Form A has lower hygroscopicity, which may better guarantee the quality, safety and stability of the active ingredient, ensure the quality, safety and stability of lasmiditan formulations in its manufacturing and storage processes, avoid problems such as content uniformity issues of active ingredients and increase in impurities, and also avoid special and expensive packaging.

The present invent provides preparation methods of lasmiditan hydrochloride Form A, which comprises any one of the following preparation methods:

1) dissolving lasmiditan hydrochloride in a solvent to form a solution, and volatilizing the solution to dryness to obtain Form A;

preferably, the solvent is selected from the group consisting of alcohol, nitromethane, dichloromethane, 1,4-dioxane, acetonitrile, and a mixture thereof; more preferably, the solvent is selected from the group consisting of ethanol, nitromethane, and a mixture thereof;

preferably, the mass to volume ratio of lasmiditan to solvent is 5 to 25 mg:1 mL;

preferably, the volatilization process is carried out at room temperature;

2) placing lasmiditan in a solvent to form a suspension, stirring the suspension for crystallization, separating crystals and drying the crystals to obtain Form A;

preferably, the solvent is selected from the group consisting of alcohol, ether, ester, ketone, alkane, tetrahydrofuran, 1,4-dioxane, toluene, and a mixture thereof; more preferably, the solvent is selected from the group consisting of acetone, acetonitrile, and a mixture thereof;

preferably, the mass ratio of lasmiditan to solvent is 50 to 200 mg: 1 mL, more preferably 50 to 100 mg: 1 mL;

preferably, the stirring time is from 1 day to 7 days, more preferably from 3 to 7 days;

preferably, the stirring process is carried out at room temperature.

According to the purpose of the invention, the fifth aspect of the present invention is to provide a solid-state lasmiditan hydrochloride Form B and its preparation method.

Lasmiditan hydrochloride Form B, having the structural shown in formula (III) below:

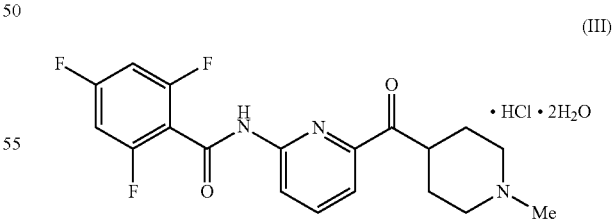

(III)

wherein Form B is dihydrate, using Cu-Kα radiation, the X-ray powder diffraction pattern of Form B, expressed as 2θ angles, has the following characteristic peaks: 14.3±0.2°, 15.6±0.2°, 23.8±0.2°, 29.5±0.2°, 23.8±0.2° and 29.5±0.2°.

In a preferred embodiment of the present invention, the X-ray powder diffraction pattern of lasmiditan hydrochloride Form B, expressed as 2θ angles, has the following characteristic peaks: 14.3±0.2°, 15.6±0.2°, 18.7±0.20, 19.3±0.2°, 21.9±0.2°, 23.8±0.2°, 26.0±0.2°, 28.3±0.2°, 29.5±0.2°, 31.4±0.2°, 32.8±0.2° and 38.2±0.2°.

In a further preferred embodiment of the present invention, the X-ray powder diffraction pattern of lasmiditan hydrochloride Form B, expressed as 2θ angles, has the following characteristic peaks and relative intensities:

| 2θ | Relative Intensity % (I) |
|---|---|
| 14.3 ± 0.2° | 100.0 |
| 15.6 ± 0.2° | 76.1 |
| 17.0 ± 0.2° | 7.0 |
| 18.7 ± 0.2° | 20.1 |
| 19.3 ± 0.2° | 19.9 |
| 21.7 ± 0.2° | 8.0 |
| 21.9 ± 0.2° | 10.7 |
| 23.8 ± 0.2° | 70.1 |
| 24.4 ± 0.2° | 12.7 |
| 26.0 ± 0.2° | 27.3 |
| 27.7 ± 0.2° | 6.3 |
| 28.3 ± 0.2° | 10.5 |
| 29.0 ± 0.2° | 10.9 |
| 29.5 ± 0.2° | 54.3 |
| 30.3 ± 0.2° | 12.3 |
| 31.4 ± 0.2° | 17.9 |
| 32.8 ± 0.2° | 36.4 |
| 38.2 ± 0.2° | 44.9. |

Non-restrictively, in one typical embodiment, the XRPD pattern of lasmiditan hydrochloride Form B is depicted in FIG. 27.

The DSC thermogram of lasmiditan hydrochloride Form B is depicted in FIG. 28.

The TGA thermogram of lasmiditan hydrochloride Form B is depicted in FIG. 29.

The PLM plot of lasmiditan hydrochloride Form B is depicted in FIG. 30.

The DVS isothermal plot of lasmiditan hydrochloride Form B is depicted in FIG. 31.

Compared with the known lasmiditan hydrochloride amorphous form, lasmiditan hydrochloride Form B of the present invention has the following beneficial properties:

1) According to the XRPD pattern and PLM plot, lasmiditan hydrochloride Form B is a crystal solid with high crystallinity and regular morphology.

2) According to the DVS isothermal sorption plot, the weight change of lasmiditan hydrochloride Form B is 4.2% between 0 to 80% RH, while the weight change of lasmiditan hydrochloride amorphous form is 8.1% in the same humidity range, therefore the hygroscopicity of lasmiditan hydrochloride Form B is lower than that of lasmiditan hydrochloride amorphous form.

3) According to Comparative Example 1, lasmiditan hydrochloride amorphous form began to crystallize after having been stored for 1 day, while lasmiditan hydrochloride Form B of the invention remained unchanged after having been stored for 10 days, indicating that the lasmiditan hydrochloride Form B of the invention has better solid-state form stability.

4) According to Comparative Example 2, the chemical purity of lasmiditan hydrochloride amorphous form decreased by more than 1.5% after having been stored for 10 days in 40° C. dry conditions, while lasmiditan hydrochloride Form B remained unchanged after having been stored for 10 days. Therefore, lasmiditan hydrochloride Form B of the present invention has better chemical stability.

The above advantageous properties of lasmiditan hydrochloride Form B of the present invention show that, compared to the known lasmiditan hydrochloride amorphous form, lasmiditan hydrochloride Form B of the present invention has many advantages and is more suitable to be used as the solid form of the active ingredient in pharmaceutical formulations. The amorphous form is unstable, and it is prone to crystallize under the influences of environmental factors such as temperature and humidity. Such instability may further affect the quality and stability of the pharmaceutical formulations. Lasmiditan hydrochloride Form B as a crystalline solid, its solid-state form stability is obviously better. Crystalline solids usually have better flowability and processing characteristics (processing such as filtrating, drying, weighing, screening, and so on), which are beneficial in improving the homogeneity of the pharmaceutical formulations. In addition, lasmiditan hydrochloride Form B has lower hygroscopicity, which may better guarantee the quality, safety and stability of the active ingredient, ensure the quality, safety and stability of lasmiditan formulations in the manufacturing and storage processes, avoid problems such as content uniformity issues of active ingredient and increases in impurities, and also avoid special and expensive packaging.

The present invention provides preparation methods of lasmiditan hydrochloride Form B, which comprise any one of the following preparation methods:

1) dissolving lasmiditan hydrochloride in a solvent to form a solution, cooling the solution for crystallization, separating crystals and drying the crystals to obtain Form B;

preferably, the solvent is selected from solvents containing water; more preferably, the solvent is a mixed solvent of water and ethanol;

preferably, the volume percentage of water in the mixed solvent is 40% to 100%, more preferably 60% to 100%;

preferably, the mass to volume ratio of lasmiditan hydrochloride to the solvent is 100 to 200 mg: 1 mL;

preferably, the crystallization time is 3 to 5 days, the crystallization temperature is lower than the solution preparation temperature, more preferably 4° C.;

preferably, the drying temperature is from 10° C. to 40° C., more preferably room temperature;

preferably, the drying time is from 1 to 12 hours, more preferably from 1 to 5 hours.

2) dissolving lasmiditan hydrochloride in a solvent to form a solution, and volatilizing the solution to dryness to obtain Form B;

preferably, the solvent is selected from aqueous solvents; more preferably, the solvent is a mixed solvent of water and ethanol.

preferably, the volume percentage of water in the mixed solvent is 40% to 100%;

preferably, the mass to volume ratio of lasmiditan hydrochloride to the solvent is 100 to 150 mg: 1 mL;

preferably, the volatilization process is carried out at room temperature.

According to the purpose of the invention, the sixth aspect of the invention is to provide a solid-state lasmiditan hydrochloride Form C and its preparation method.

The lasmiditan hydrochloride Form C, having the structural shown in formula (IV) below:

(IV)

wherein using Cu-Kα radiation, the X-ray powder diffraction pattern of Form C, expressed as 2θ angles, has the following characteristic peaks: 13.1±0.2°, 13.8±0.20, 14.9±0.2°, 16.6±0.2°, 18.0±0.2° and 22.2±0.2°.

In a preferred embodiment of the present invention, the X-ray powder diffraction pattern of lasmiditan hydrochloride Form C, expressed as 2θ angles, has the following characteristic peaks: 13.1±0.2°, 13.8±0.2°, 14.9±0.2°, 16.6±0.2°, 17.7±0.20, 18.0±0.2°, 19.6±0.2°, 20.4±0.2°, 21.6±0.2°, 22.2±0.2°, 24.6±0.2° and 27.5±0.2°.

In a further preferred embodiment of the present invention, the X-ray powder diffraction pattern of lasmiditan hydrochloride Form C, expressed as 2θ angles, has the following characteristic peaks and relative intensities:

| 2θ | Relative Intensity % (I) |
|---|---|
| 8.9 ± 0.2° | 5.0 |
| 13.1 ± 0.2° | 40.4 |
| 13.8 ± 0.2° | 45.8 |
| 14.9 ± 0.2° | 11.5 |
| 16.6 ± 0.2° | 100.0 |
| 17.0 ± 0.2° | 5.6 |
| 17.7 ± 0.2° | 13.8 |
| 18.0 ± 0.2° | 33.2 |
| 19.1 ± 0.2° | 4.3 |
| 19.6 ± 0.2° | 11.6 |
| 20.4 ± 0.2° | 8.4 |
| 21.6 ± 0.2° | 11.7 |
| 22.2 ± 0.2° | 32.9 |
| 24.6 ± 0.2° | 7.7 |
| 25.9 ± 0.2° | 9.9 |
| 26.7 ± 0.2° | 5.9 |
| 27.5 ± 0.2° | 12.7 |
| 28.3 ± 0.2° | 11 |
| 29.1 ± 0.2° | 5.2 |
| 31.1 ± 0.2° | 7.1 |

Non-restrictively, in one typical embodiment, the XRPD pattern of lasmiditan hydrochloride Form C is depicted in FIG. 32.

The DSC thermogram of lasmiditan hydrochloride Form C is depicted in FIG. 33.

The TGA thermogram of lasmiditan hydrochloride Form C is depicted in FIG. 34.

The PLM plot of lasmiditan hydrochloride Form C is depicted in FIG. 35.

The isothermal sorption plot of lasmiditan hydrochloride Form B is depicted in FIG. 36.

Compared with the known lasmiditan hydrochloride amorphous form, lasmiditan hydrochloride Form C of the present invention has the following beneficial properties:

1) According to the XRPD pattern and PLM plot, lasmiditan hydrochloride Form C is a crystal solid with high crystallinity and regular morphology.

2) According to the DVS isothermal plot, the weight change of lasmiditan hydrochloride Form C is 0.9% between 0 to 80% RH, while the weight change of lasmiditan hydrochloride amorphous form is 8.1%; therefore the hygroscopicity of lasmiditan hydrochloride Form C is much lower than that of lasmiditan hydrochloride amorphous form.

3) According to Comparative Example 1, lasmiditan hydrochloride amorphous form began to crystallize after having been stored for 1 day, while lasmiditan hydrochloride Form C of the invention remained unchanged after having been stored for 10 days, indicating that the lasmiditan hydrochloride Form C of the invention has better solid-state form stability.

4) According to Comparative Example 2, the chemical purity of lasmiditan hydrochloride amorphous form decreased by more than 1.5% after having been stored for 10 days in 40° C. dry conditions, while lasmiditan hydrochloride Form C remained unchanged after having been stored for 10 days. Therefore, lasmiditan hydrochloride Form C of the present invention has better chemical stability.

The above advantageous properties of lasmiditan hydrochloride Form C show that, compared to the known lasmiditan hydrochloride amorphous form, lasmiditan hydrochloride Form C of the present invention has many advantages and is more suitable to be used as the solid form of the active ingredient in pharmaceutical formulations. The amorphous form is unstable, and it is prone to crystallize under the influence of environmental factors such as temperature and humidity. Such instability may further affect the quality and stability of the pharmaceutical formulations. lasmiditan hydrochloride Form C is crystalline, and its solid-state form stability is obviously better (than amorphous solids). Crystalline solids usually have better flowability and processing characteristics (processing such as filtrating, drying, weighing, screening, and so on), which are beneficial to improving the homogeneity of the pharmaceutical formulations. In addition, lasmiditan hydrochloride Form C has lower hygroscopicity, which may better guarantee the quality, safety and stability of the active ingredient, ensure the quality, safety and stability of lasmiditan formulations in the manufacturing and storage processes, such as content uniformity issues of the active ingredient and increases in impurities, and also avoid special and expensive packaging.

The present invention provides preparation methods of lasmiditan hydrochloride Form C, which comprise any one of the following preparation methods:

1) dissolving lasmiditan hydrochloride in a solvent to form a solution, and volatilizing the solution to dryness to obtain Form C;

preferably, the solvent is selected from the group consisting of a mixed solvent of trifluoroethanol and water, a mixed solvent of isopropyl alcohol and water, water-saturated n-butanol, and water-saturated 2-butanol;

preferably, the volume percentage of water in the mixed solvent is 2% to 10%;

preferably, the mass to volume ratio of the lasmiditan hydrochloride to the solvent is 10 to 50 mg:1 mL, more preferably 25 to 50 mg:1 mL;

preferably, the volatilization process is carried out at room temperature.

2) dissolving lasmiditan hydrochloride in a solvent to form a solution, cooling the solution for crystallization, separating crystals and drying the crystals to obtain Form C;

preferably, the solvent is a mixed solvent of water and acetone;

preferably, the volume percentage of water in the mixed solvent is 2% to 5%;

preferably, the mass ratio of the lasmiditan hydrochloride to the solvent is 25 to 50 mg: 1 mL;

preferably, the crystallization time is 1 to 7 days, more preferably 3 to 7 days;

preferably, the crystallization temperature is lower than that of the solution preparation temperature, more preferably 4° C.;

preferably, the drying temperature is from 10° C. to 40° C., more preferably room temperature;

preferably, the drying time is from 1 to 12 hours, more preferably from 1 to 5 hours.

According to the purpose of the invention, the seventh aspect of the invention is to provide a solid-state lasmiditan hydrochloride Form E and its preparation method. wherein using Cu-Kα radiation, the X-ray powder diffraction pattern of Form E, expressed as 2θ angles, has the following characteristic peaks: 11.5±0.2°, 14.0±0.2°, 18.9±0.2°, 20.2±0.2°, 21.0±0.2°, 23.2±0.2°, 25.3±0.2°, 26.3±0.2°, 28.1±0.2°, 29.1±0.2°, 29.3±0.2° and 35.2±0.2°.

Non-restrictively, in one typical embodiment, the XRPD pattern of lasmiditan hydrochloride Form E is shown in FIG. 37.

The invention provides a preparation method of lasmiditan hydrochloride Form E, which includes the following steps: at room temperature, placing lasmiditan hydrochloride in a halogenated alkane to form a solution and volatilizing the solution to dryness to obtain the lasmiditan hydrochloride Form E. Preferably, the halogenated alkane is chloroform or dichloromethane.

According to the purpose of the invention, the eighth aspect of the invention is to provide a solid state lasmiditan hydrochloride Form G and its preparation method. wherein, using Cu-Kα radiation, the X-ray powder diffraction pattern of Form G, expressed as 2θ angles, has the following characteristic peaks: 8.3±0.2°, 12.7±0.20, 13.8±0.2°, 14.4±0.2°, 14.9±0.2°, 16.8±0.2°, 17.7±0.20, 20.1±0.2°, 23.7±0.20, 24.6±0.2°, 27.8±0.2° and 29.6±0.2°.

Non-restrictively, in one typical embodiment, the XRPD pattern of lasmiditan hydrochloride Form G is shown in FIG. 38.

The present invention provides a preparation method of lasmiditan hydrochloride Form G, which includes the following steps: heating a certain amount of lasmiditan hydrochloride Form B at 80° C. for 5 min to obtain lasmiditan hydrochloride Form G.

In the above preparation methods of crystalline forms of lasmiditan and crystalline forms of lasmiditan hydrochloride of the present invention: the starting material "lasmiditan and lasmiditan hydrochloride" may be an already disclosed lasmiditan compound, its crystalline forms or its amorphous forms, for example, including but not limited to lasmiditan and lasmiditan hydrochloride obtained by referring to either preparation methods of patents CN100352817C and U.S. Pat. No. 8,697,876B2. These patent documents are incorporated into this application by reference in their entireties.

The term "room temperature" refers to a temperature between 10° C. and 30° C.

"Stirring" may be carried out by a conventional stirring method in the art, such as magnetic stirring, mechanical stirring, and the stirring speed is 50 to 1800 r/min, preferably 300 to 900 r/min.

The "separation" may be performed using conventional methods in the field, such as centrifugation or filtration. Preferred method is vacuum filtration, generally at a pressure less than atmospheric pressure at room temperature, preferably less than 0.09 MPa.

Drying may be performed by routine methods in the field, such as room temperature drying, forced air drying or vacuum drying. Drying instruments and methods are unrestricted, and may be fume hood, blast oven, spray drying, fluidized bed drying or vacuum oven. Drying is performed under reduced pressure or atmospheric pressure, pressure less than 0.09 MPa is preferred. Drying temperature is from 10 to 40° C., the drying time is from 10 to 72 hours, preferably from 2 to 24 hours, more preferably from 2 to 8 hours.

In the present invention, "crystal" or "crystalline form" refers to that characterized by X-ray powder diffraction pattern, having a unique ordered molecular arrangement or configuration within the crystalline lattice. It is known to those skilled in the field that the experimental error depends on instrumental conditions, sample preparation and sample purity. The 2θ angle of the peaks in the XRPD pattern may change with the change of instrument and samples. The difference of peak position may vary by 1°, 0.8°, 0.5°, 0.3°, 0.10, etc. depending on the instruments and samples, and +0.2° is usually allowed. Therefore the difference in peak angle should not be regarded as the only factor. The relative intensity of peaks may change with the change of sample, sample preparation, and other experimental conditions. Therefore, the order of peak intensities should not be regarded as the only or the determining factor. Due to the effect of experimental factors including sample height, peak position may shift. Generally, a small amount of peak shifting is acceptable. Hence, it is easily understood for those skilled in the field that any crystalline form having the same or similar X-ray powder diffraction pattern as that of the crystalline form in the present invention should be within the scope of the present invention. "Single crystalline form" refers to a crystalline form confirmed by X-ray powder diffraction as a single form.

Lasmiditan and lasmiditan hydrochloride forms of the present invention are substantially pure, single, and substantially free of any other crystalline or amorphous form. As used herein, "substantially pure" when used in reference to a new crystalline form means that the new crystalline form comprises at least 80% by weight of the present compound, more preferably at least 90% (by weight), especially at least 95% (by weight), especially at least 99% (by weight).

According to the purpose of the invention, the ninth aspect of the invention is to provide a pharmaceutical composition, which comprises a therapeutic and/or preventive effective amount of pharmaceutical active ingredient selected from crystalline forms of lasmiditan and lasmiditan hydrochloride of the present invention or from crystalline forms of lasmiditan and lasmiditan hydrochloride prepared by the preparation methods of the present invention, and at least one pharmaceutically acceptable excipient or carrier. Wherein lasmiditan forms of the present invention include lasmiditan Form 1, Form 2 and Form 3. The lasmiditan hydrochloride forms of the present invention include lasmiditan hydrochloride Form A, Form B, Form C, Form E and Form G. In addition, the pharmaceutical composition may also comprise other crystalline forms, amorphous forms or pharmaceutical acceptable salts of lasmiditan.

The dosage form of the compound used in the method of the present invention can be determined by selected specific solid state of the compound, the administration route and patient status. The pharmaceutical formulation of the present invention can be prepared according to generally accepted methods in the field to be suitable for one or more of the following administration routes, which include oral administration, sublingual administration, parenteral injection (including subcutaneous injection, intravenous injection, intramuscular injection, sternum injection or infusion technology), inhalation administration, nasal administration, or rectum administration, and the pharmaceutical formulation contains at least one active ingredient.

The term "patient" used in this patent refers to an animal that is the target of treatment, observation or experiments, preferably a mammal, more preferably a human.

The term "effective dose" refers to a dose sufficient to perform a therapeutic or preventive function. "Pharmacologically acceptable" means that the components of the pharmaceutical composition are compatible with each other and are suitable for the recipient.

The "pharmaceutical composition" or "composition" is intended to include a bulk composition and/or individual dose unit consisting of one or more active pharmaceutical ingredients of the lasmiditan crystalline forms of the present invention and any non-pharmaceutically active excipients. Bulk compositions and individual dose units may contain a fixed amount of one or more of the above active pharmaceutical ingredients. Bulk compositions are substances that have not yet formed individual units of dose. Examples of nonrestrictive dose units are oral dose units for tablets, pills, and their analogues. Similarly, the pharmaceutical composition of the present invention given to the individual in need is intended to include both bulk composition and individual dose unit mentioned above.

Generally, the composition of the present invention comprises an active ingredient, which is usually mixed with an excipient, diluted by an excipient, or enclosed within such a carrier which can be in a form of a capsule, a sachet or other container. When an excipient is used as a diluent, it may be a solid, semi-solid, or liquid material, which functions as an excipient, carrier, or medium of the active ingredient. Thus, the pharmaceutical composition may be in the form of tablets, pills, lozenges, powders, sachet, cachets, elixirs, suspension, s emulsions, solutions, syrups, aerosols (either in solid or in liquid medium), sprays, ointments, soft or hard capsules, gels, suppositories, sterile injectable solutions, and sterile package powders.

In preparation of pharmaceutical formulations, active ingredient may need to be milled to provide appropriate particle size before mixing with other components.

If the active ingredient is basically insoluble, it is usually milled to a size less than 75 μm.

If the active ingredient is essentially water-soluble, it is usually milled to adjust its particle size so that it has a uniform particle size distribution in the formulation, for example, about 425 μm.

Examples of excipients for solid dosage form suitable for oral administration include sugars, such as glucose, sucrose, lactose, sorbitol, mannose, starch, gum Arabic, calcium phosphate, alginate, gelatin, calcium silicate, microcrystalline cellulose, polyvinylpyrrolidone, kaolin, cellulose, methyl cellulose, adhesives, disintegrating agents, etc. Some liquid formulations suitable for oral administration (such as suspending agents, syrups, elixirs, etc.) can use media such as water, glycol, oil or alcohol. Parenteral composition usually uses sterile water as a carrier and optionally other components such as solubilizers. Injectable solution may be prepared, for example, using a carrier containing a saline solution, a glucose solution, or a solution containing a mixture of saline and glucose. Pharmaceutical formulation may also include lubricants (such as talc powder, magnesium stearate and mineral oils), wetting agents, emulsifiers and suspensions, preservatives such as propyl hydroxybenzoate, sweeteners and flavoring agents. The compound of the present invention can be prepared by the methods known in this field, so that the active ingredient can be released rapidly, continuously or delayed after drug administration.

According to the present invention, the invention provides the pharmaceutical composition, comprising crystalline forms of lasmiditan or crystalline forms of its hydrochloride of the present invention or crystalline forms of lasmiditan or crystalline forms of its hydrochloride prepared by using preparation methods of the present invention, for treating or preventing migraine in patients and/or other diseases related to the dysfunction of 5-$HT_{1F}$ receptor.

The diseases are selected from at least one of the following: migraine, general pain, trigeminal neuralgia, dental pain or temperomandibular joint disfunctional pain, anxiety, general anxiety, panic disorder, fatigue, depression, sleep disorders, premenstrual syndrome or luteal phase syndrome, seasonal affective disorders, post-traumatic syndrome, memory loss, dementia (including dementia of aging), social panic, autism, schizophrenia, hyperactivity deficit disorder, disruptive behavior disorder, impulsive control disorder, borderline personality disorder, obsessive compulsive disorder, sexual dysfunction, appetite disorder, epilepsy, anorexia nervosa, alcoholism, tobacco abuse, mutism, and trichotillomania.

According to the purpose of the present invention, the invention provides methods for treating or preventing migraine in a patient and/or other diseases or symptoms related to the dysfunction of 5-$HT_{1F}$ receptor thereof comprising administering to a patient an effective amount of an active ingredient selected from the group consisting of lasmiditan Form 1, lasmiditan Form 2, lasmiditan Form 3, lasmiditan hydrochloride Form A, lasmiditan hydrochloride Form B, and lasmiditan hydrochloride Form C of the present invention or pharmaceutical composition comprising an active ingredient selected from the group consisting of lasmiditan Form 1, lasmiditan Form 2, lasmiditan Form 3, lasmiditan hydrochloride Form A, lasmiditan hydrochloride Form B, and lasmiditan hydrochloride Form C. The diseases are the same as those described above.

The active ingredient is usually effective in a large dose range. For example, the daily dose of the active ingredient (either single dose or fractional dose) is generally about 0.001-30 mg/kg/body weight. For treatment of adult, the preferred dose (single dose or fractional dose) is approximately 0.1 to 15 mg/kg/day. However, it should be understood that the actual amount and frequency of drug administration for any given patient varies and depend on a variety of factors, including the potency of the compound used, metabolism and duration of drug action, one or more compounds actually to be taken, the disease to be treated and its severity, administration route, age, weight, excretion rate and overall response of the specific patient, thus the above dose range shall not limit the scope of the invention in any way. In some cases, a dose level below the above said range may be more appropriate, while in others a larger dose without any side effects may be used, provided that the larger dose is first divided into smaller doses for the full day to use.

SPECIFIC IMPLEMENTATIONS

Figure 1:
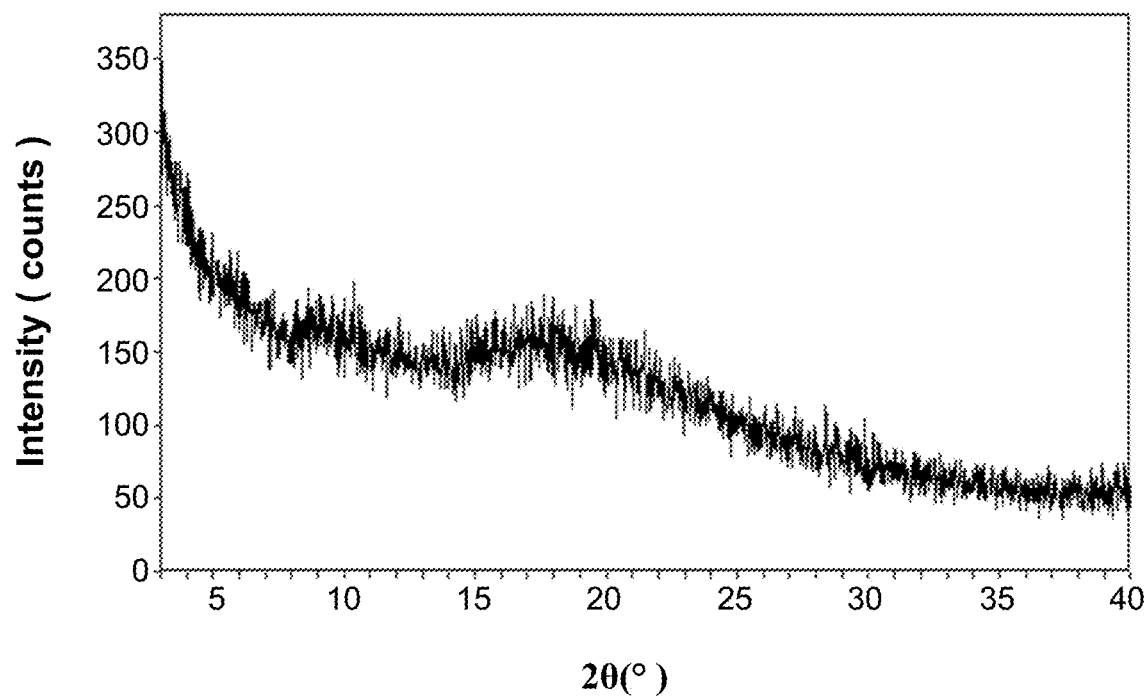
FIG. 1 is the XRPD pattern of lasmiditan amorphous form prepared according to CN100352817C.

The following examples help to further understand the present invention, but are not intended to limit the contents of the present invention.

Instruments and Characterization Methods:

X-ray powder diffraction (XRPD): performed on Bruder D8 Advance diffractometer. Samples were tested at room temperature. Testing conditions: 20 scan range 3-40°, step size 0.02°, and speed 0.2 s/step.

Polarized light microscopy (PLM) patterns were collected on XP-500E polarized light microscopy. Took a small amount of powder sample on a glass and add some mineral oil. Covered with the cover glass, placed it on the stage for observation and took a picture.

Differential thermal analysis data were collected on TA Instruments Q200 MDSC. Method: A sample of 1 to 10 mg was placed in a sealed aluminum pan, and the sample was heated from room temperature to 300° C. at a heating rate of 10° C./min under the protection of dry nitrogen purge at 40 mL/min.

Thermogravimetric analysis data were collected on TA Instruments Q500 TGA. Method: A sample of 5 to 15 mg was placed in a platinum pan, using High Resolution™, the sample was heated from room temperature to 300° C. at a heating rate of 10° C./min under the protection of dry nitrogen purge at 40 mL/min.

Dynamic vapor sorption data and isothermal sorption data were collected on TA Instruments Q5000 TGA. Method: A sample of 1 to 10 mg was placed in a platinum pan; the weight change of the sample during the change in relative humidity from 0% to 80% to 0% was measured.

$^1$H Nuclear magnetic resonance spectrum ($^1$H-NMR) data were collected on Bruker Avance II DMX 400 MHz nuclear magnetic resonance spectrometer. A sample of 1 to 5 mg was placed in a nuclear magnetic sample tube, and it was dissolved using about 0.5 mL of deuterated reagent before being tested.

Ion chromatograph data were collected on Dionex ICS-900. Data collection and analysis software was Chromeleon Console. The ion content was analyzed by an external standard method.

HPLC purity data were collected on Agilent 1260 high performance liquid chromatography under the following conditions: column, Agilent Zorbax Eclipse XDB-C18 (4.6*150 mm, 5 m); detection wavelength, 220 nm; column temperature, 40° C., flow rate, 1 mL/min, injection volume 2 μL. The sample was dissolved in acetonitrile to make a solution concentration about 1.5 mg/mL, and a gradient method to determine the purity of the sample.

|  | Time (min) | % Mobile phase A | % Mobile phase B |
|---|---|---|---|
| Gradient | 0.00 | 100 | 0.0 |
|  | 0.50 | 100 | 0.0 |
|  | 30.00 | 0.0 | 90 |
|  | 35.00 | 0.0 | 90 |
|  | 35.10 | 100 | 0.0 |
|  | 40.00 (Stop) | 100 | 0.0 |

Mobile phase A H$_2$O:ACN:TFA = 950:50:1
Mobile phase B ACN:H$_2$O:TFA = 950:50:1

Unless particularly specified, all reagents used in the embodiments were commercially available.

Unless particularly specified, all embodiments were operated at room temperature.

Preparation Example 1

Preparation of Lasmiditan (Prior Art)

Lasmiditan was prepared by referencing the method of embodiment 21 in CN100352817C. The specific operation was as follows: Added triethylamine (10.67 mL, 76.70 mmol, 2.4 eq.) to a solution of 2-amino-(6-(1-methylpiperidin-4-yl)-carbonyl)-pyridine (7 g, 31.96 mmol, 1 eq.) in anhydrous THF (100 mL) under nitrogen atmosphere. Added 2,4,6-trifluorobenzoyl chloride (7.46 g, 5 mL, 38.35 mmol, 1.20 eq.) dropwise at room temperature. After 2 hours, added additional 2,4,6-trifluorobenzoyl chloride (0.75 mL, 0.15 eq.) and triethylamine (1.32 mL, 0.3 eq.) to the reaction mixture, and agitated for an additional 3 hours. Quenched the reaction with distilled water (10 mL) and 30% NaOH (15 mL). Stirred the resulting biphasic system for 1 hour and then separate the phases. Extracted the organic fraction by adding H$_2$O (75 mL) and acetic acid (12 mL), followed by cyclohexane (70 mL). Washed the organic fraction with water (50 mL) containing acetic acid (1 mL). Combined all aqueous fractions and washes and neutralize the mixture with 30% NaOH (15 mL). Extracted with methyl-tert-butyl ether (MTBE) (3*50 mL). Combined the organic fractions and dried with MgSO$_4$, filtered, and concentrated under reduce pressure, and dried under vacuum at room temperature, to obtain the title compound as a light-brown solid (11.031 g, 91% yield). The $^1$H-NMR (CDCl$_3$) data of the product was as follows: $^1$HNMR (400 MHz, Chloroform-D) ppm 1.54 (m, 2H) 2.02 (m, 2H) 2.13 (t, J=18.37 Hz, 2H) 2.29 (s, 3H) 2.80 (m, J=19.14 Hz, 1H) 3.56 (m, 1H) 4.26 (d, J=12.59 Hz, 1H) 6.17 (d, J=13.6 Hz, 1H) 6.75 (m, 2H) 7.45 (t, J=12.59 Hz, 1H) 7.53 (m, 1H) 7.95 (s, 1H).

Its XRPD pattern is shown in FIG. 1, showing an amorphous halo form with no diffraction peaks.

Figure 2:
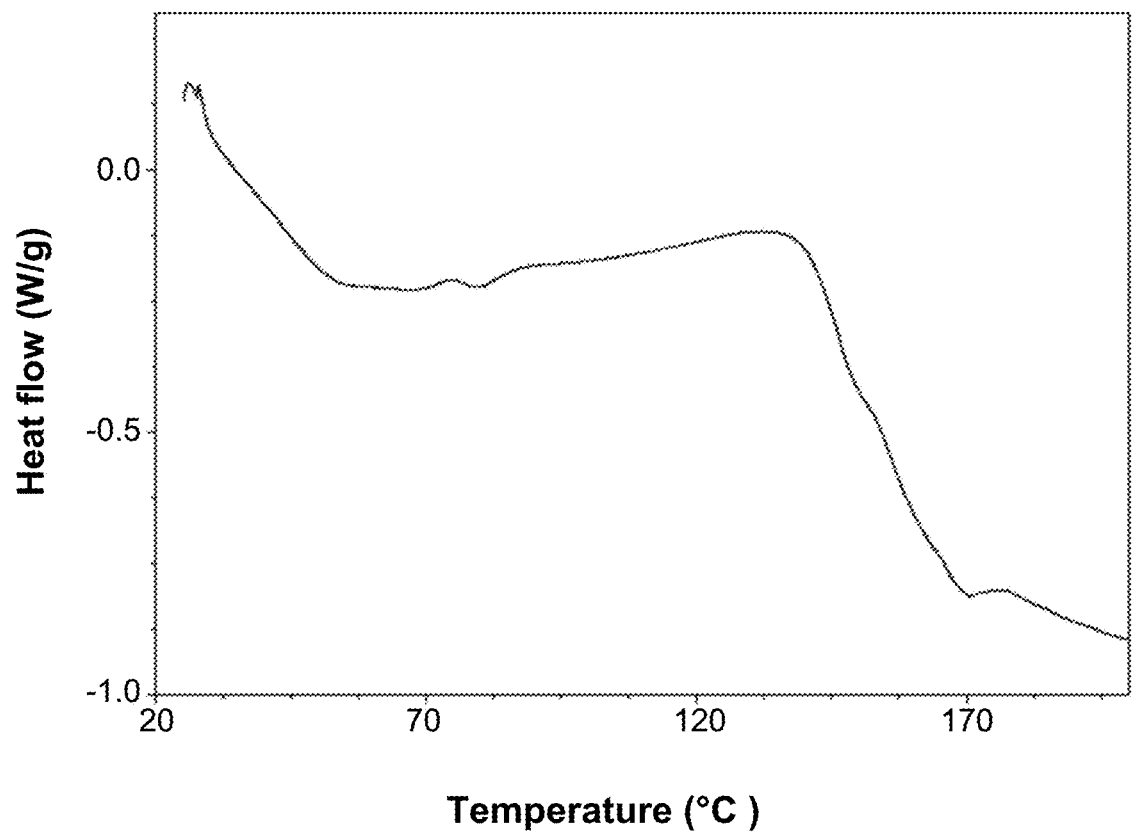
FIG. 2 is the DSC pattern of lasmiditan amorphous form prepared according to CN100352817C.

Its DSC pattern is shown in FIG. 2.

Figure 3:
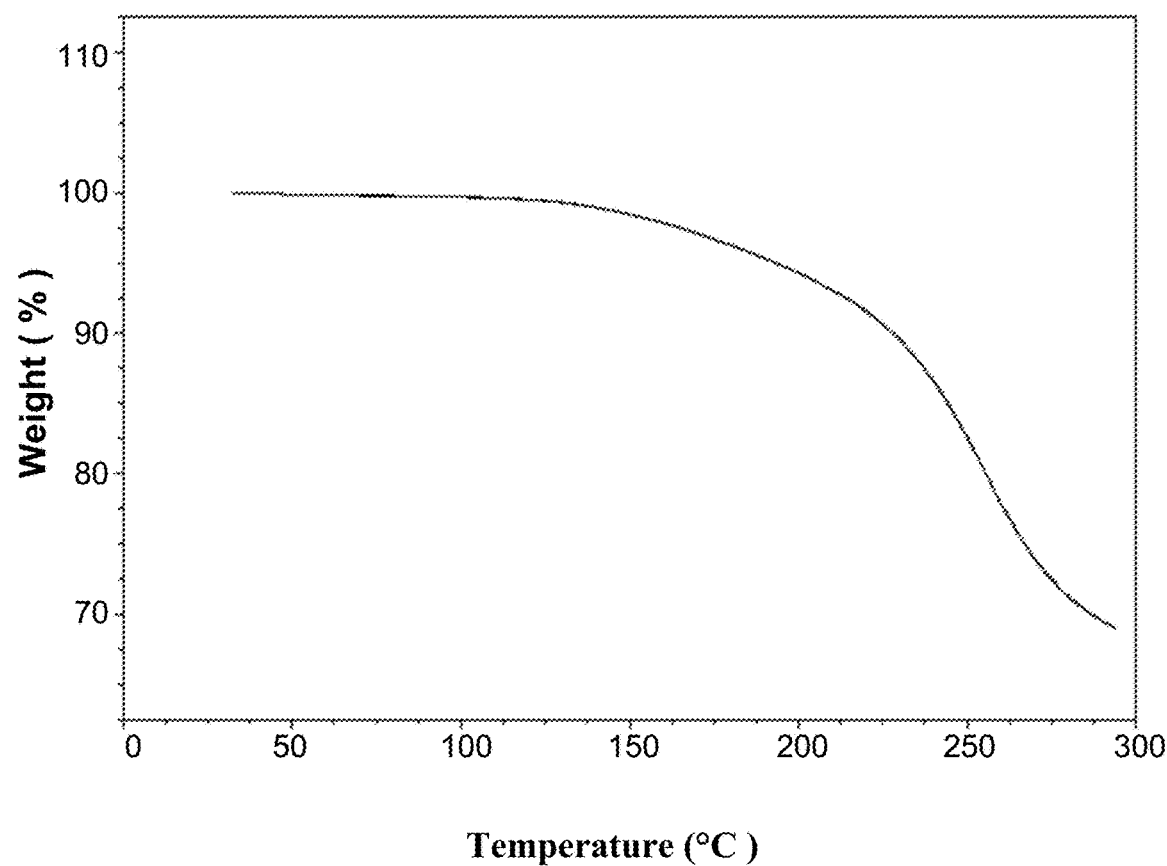
FIG. 3 is the TGA pattern of lasmiditan amorphous form prepared according to CN100352817C.

Its TGA pattern is shown in FIG. 3.

Figure 4:
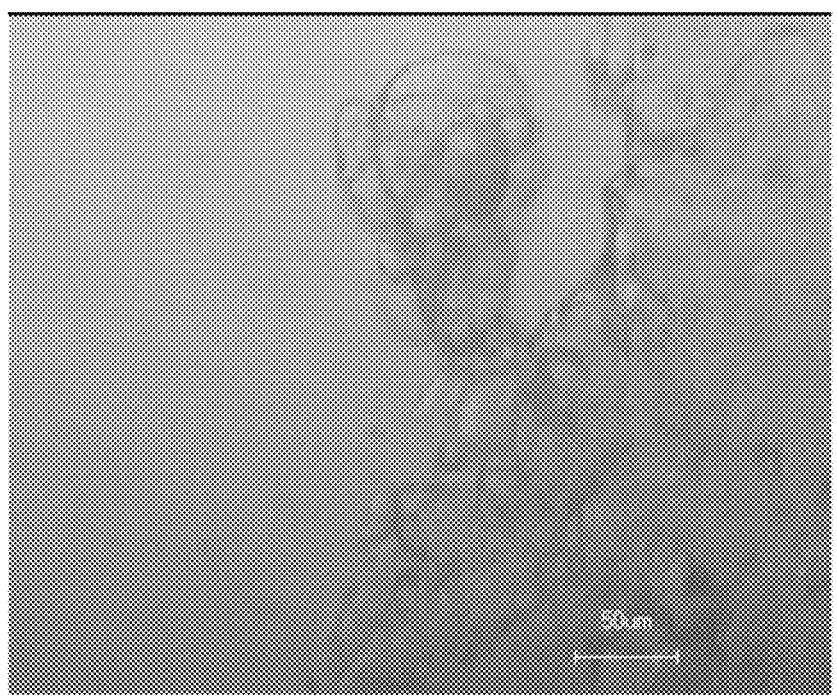
FIG. 4 is the PLM pattern of lasmiditan amorphous form prepared according to CN100352817C.

Its PLM pattern is shown in FIG. 4, showing an irregular glassy solid with no polarization.

Figure 5:
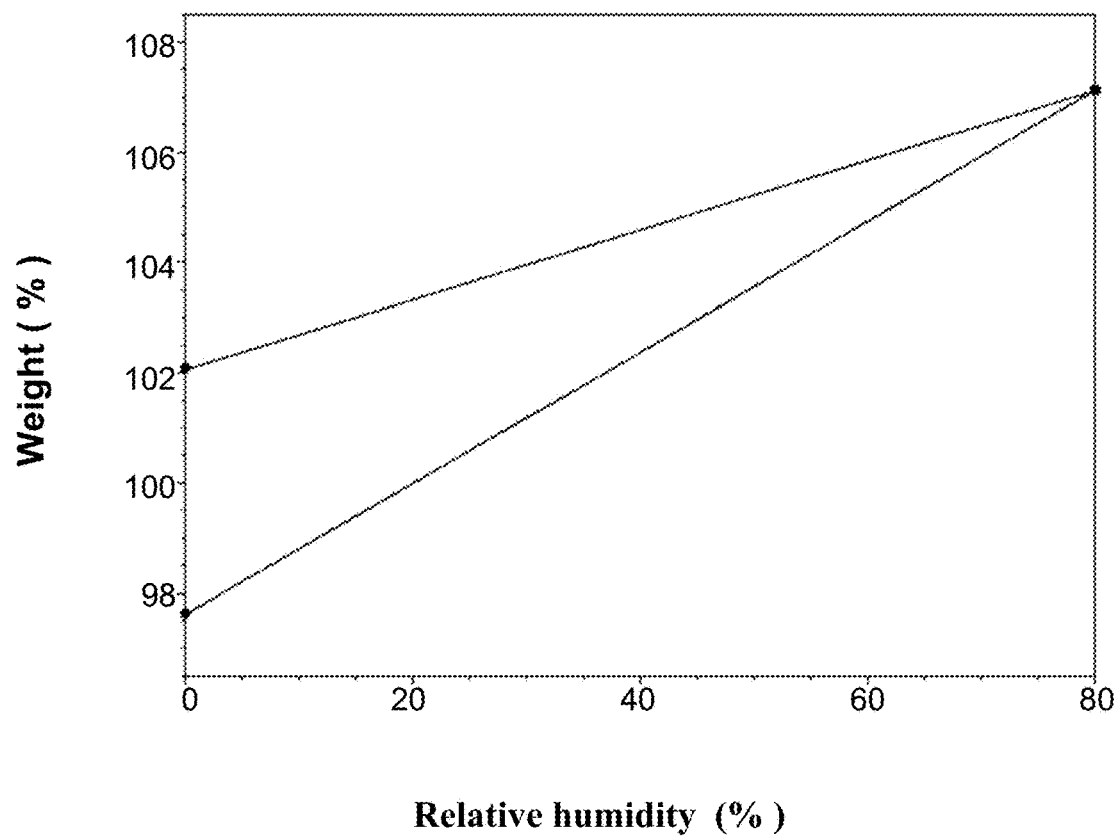
FIG. 5 is the isothermal sorption plot of lasmiditan amorphous form prepared according to CN100352817C.

Its isothermal sorption plot is shown in FIG. 5, showing weight change of 9.5% in the range of 0%-80% relative humidity.

The above characterization results indicate that lasmiditan obtained by the preparation method of CN100352817C example 21 is an amorphous form.

Preparation Example 2

The Preparation of Lasmiditan Hydrochloride (Prior Art)

Lasmiditan hydrochloride was prepared by referencing the method of embodiment 8 in CN100352817C. The specific operation was as follows: Combined 2-amino-6-(1-methylpiperidin-4-yl)pyridine (2.0 g, 9.2 mmol), 2,4,6-trifluorobenzoyl chloride (3.57 g, 18.4 mmol), and 1,4-dioxane (100 mL), and stirred while heating at reflux. After 3 hours, cooled the reaction mixture to ambient temperature and concentrate. Loaded the concentrated mixture onto an SCX column (10 g), washed with methanol, and eluted with 2M ammonia in methanol. Concentrated the eluate to obtain the free base of the title compound as an oil (3.65 g (>100%)). Dissolved the oil in methanol (50 mL) and treated with ammonium chloride (0.5 g, 9.2 mmol). Concentrated the mixture and dried under vacuum to obtain the title compound.

The IC characterization showed that lasmiditan and hydrochloric acid reacted to form a lasmiditan hydrochloride at a molar ratio of 1:1.

Figure 19:
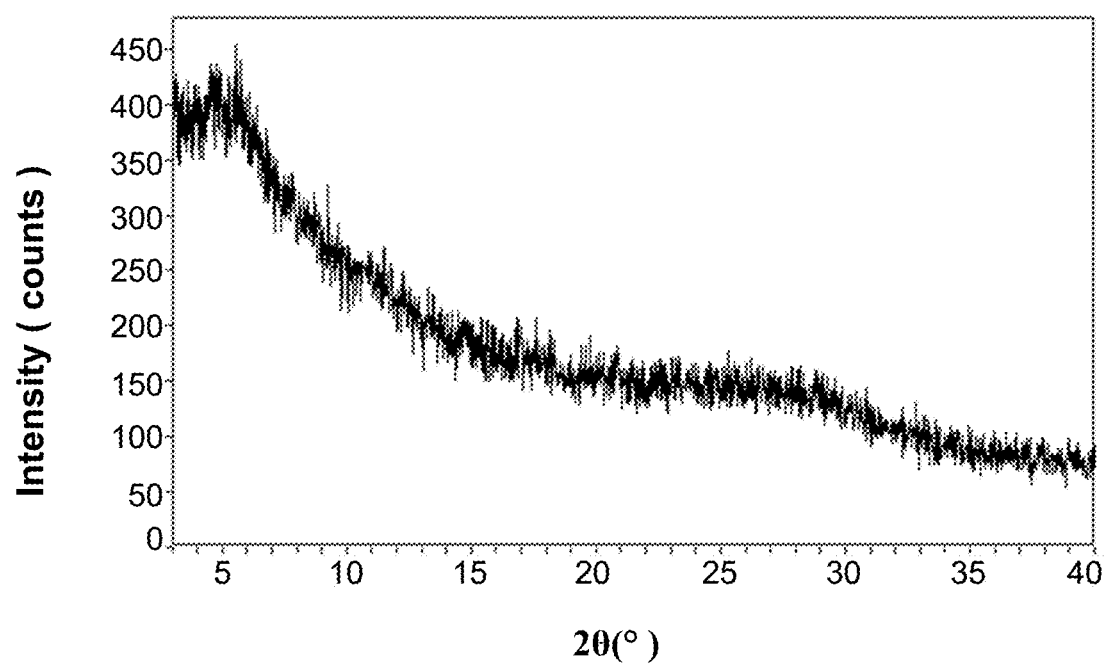
FIG. 19 is the XRPD pattern of lasmiditan hydrochloride amorphous prepared according to CN100352817C.

Its XRPD pattern is shown in FIG. 19, showing an amorphous halo with no diffraction peak.

Figure 20:
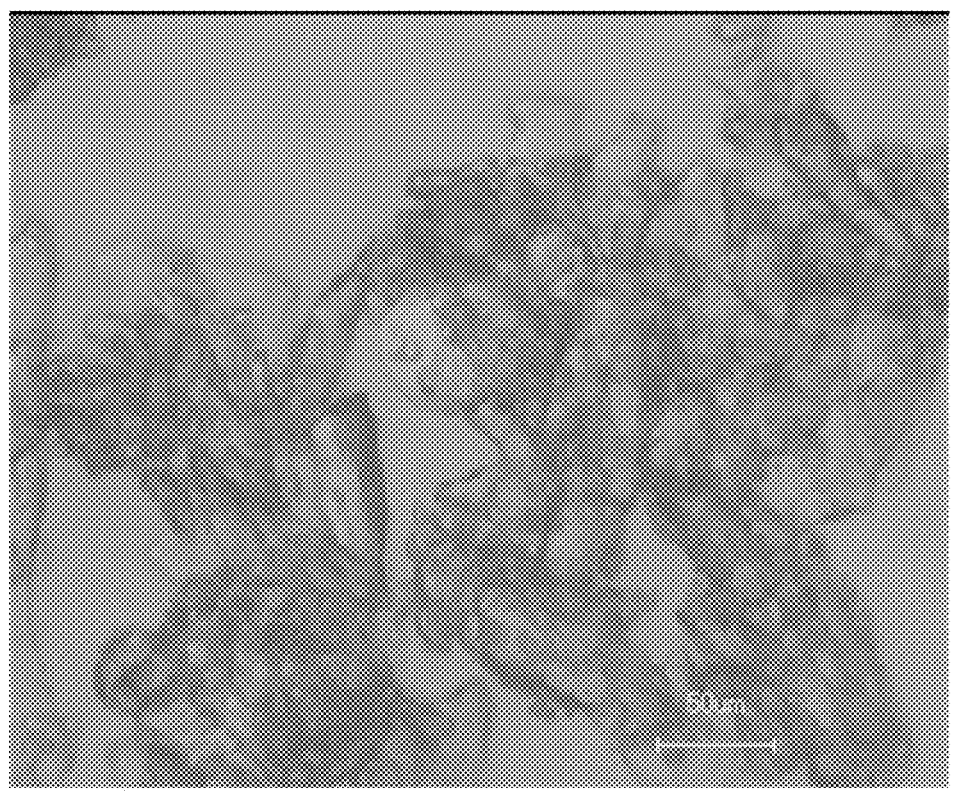
FIG. 20 is the PLM pattern of lasmiditan hydrochloride amorphous prepared according to CN100352817C.

Its PLM pattern is shown in FIG. 20, showing an irregular solid with no polarization.

Figure 21:
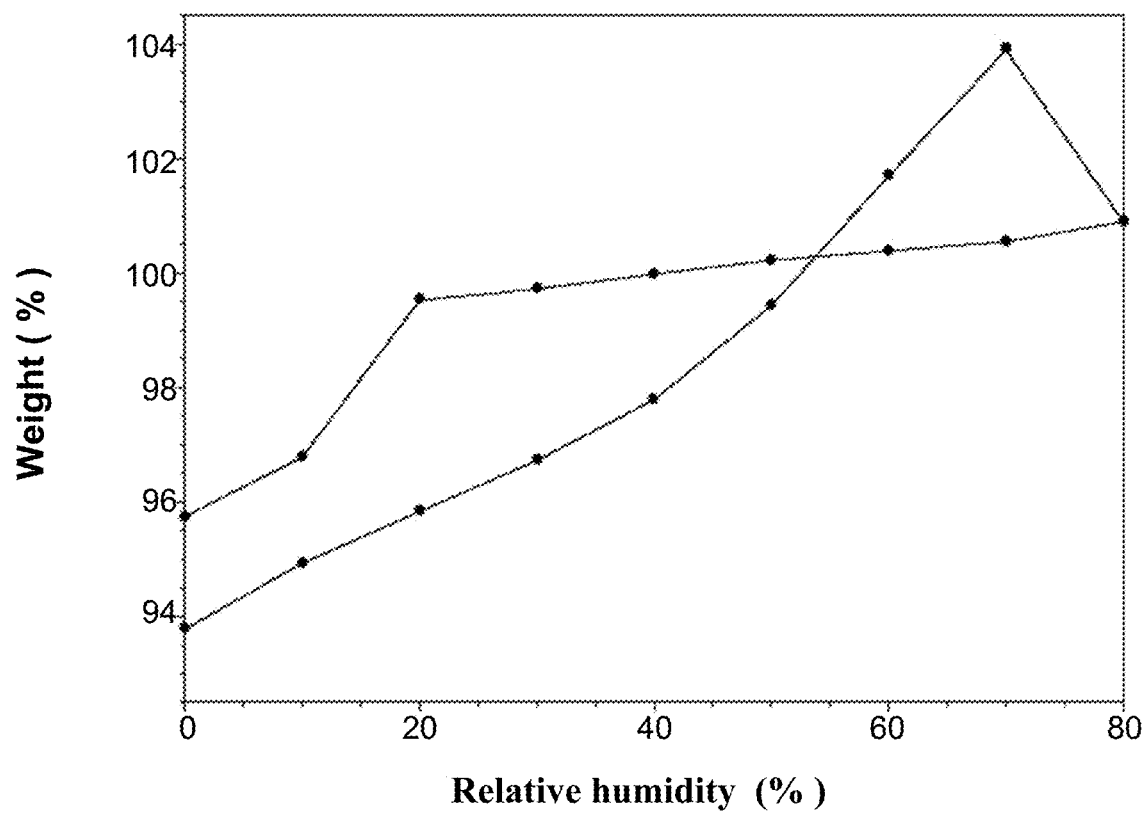
FIG. 21 is the isothermal sorption plot of lasmiditan hydrochloride amorphous prepared according to CN100352817C.

Its isothermal sorption plot is shown in FIG. 21, with a weight change of 8.1% in the range of 0%-80% relative humidity.

The above characterization results indicate that lasmiditan hydrochloride obtained by the preparation method of CN100352817C embodiment 8 is an amorphous form.

Example 1

Five hundred miligrams of lasmiditan of Preparation Example 1 was dissolved in water-methanol solution (1 mL) containing 5% water, and the solution was volatilized for crystallization at room temperature, after 1 day of volatilization, lasmiditan Form 1 was obtained (487 mg, 95% yield).

Figure 6:
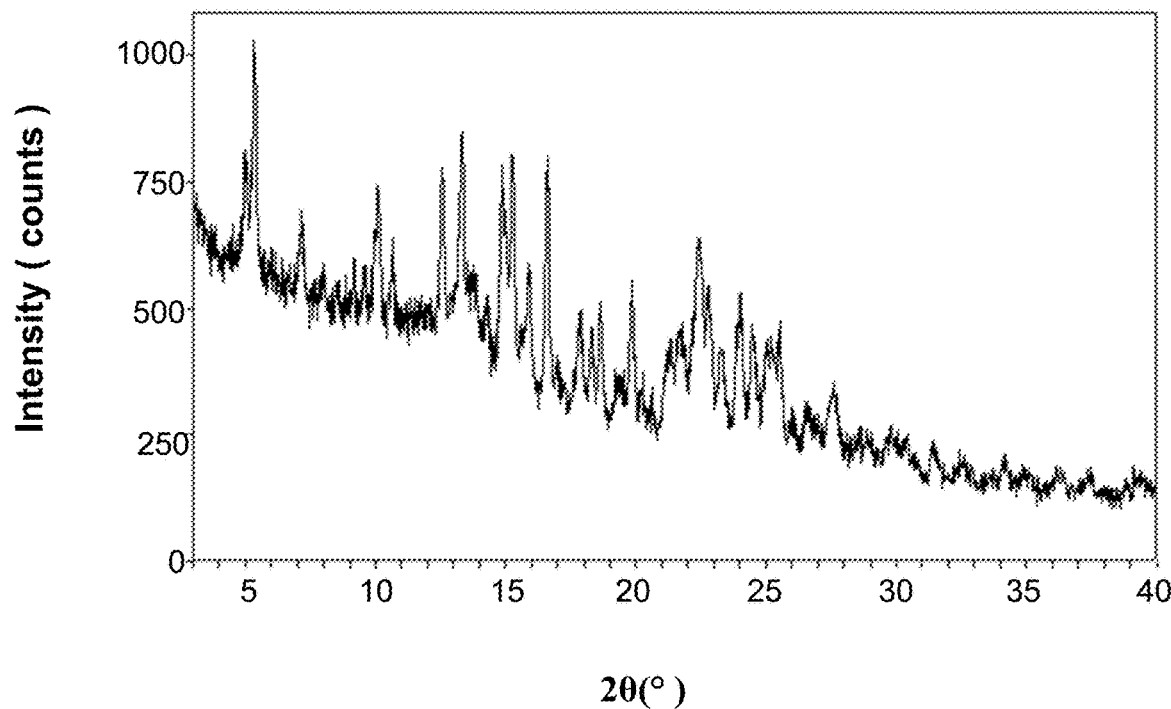
FIG. 6 is the XRPD pattern of lasmiditan Form 1 of the present invention.
Figure 7:
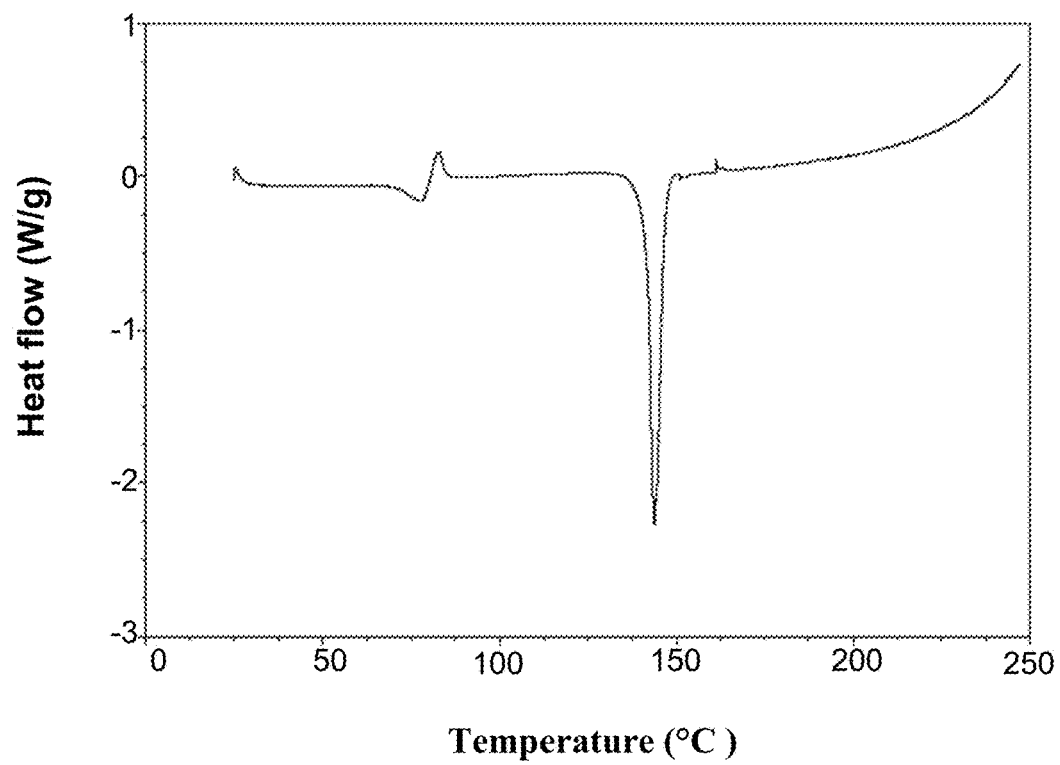
FIG. 7 is the DSC pattern of lasmiditan Form 1 of the present invention.
Figure 8:
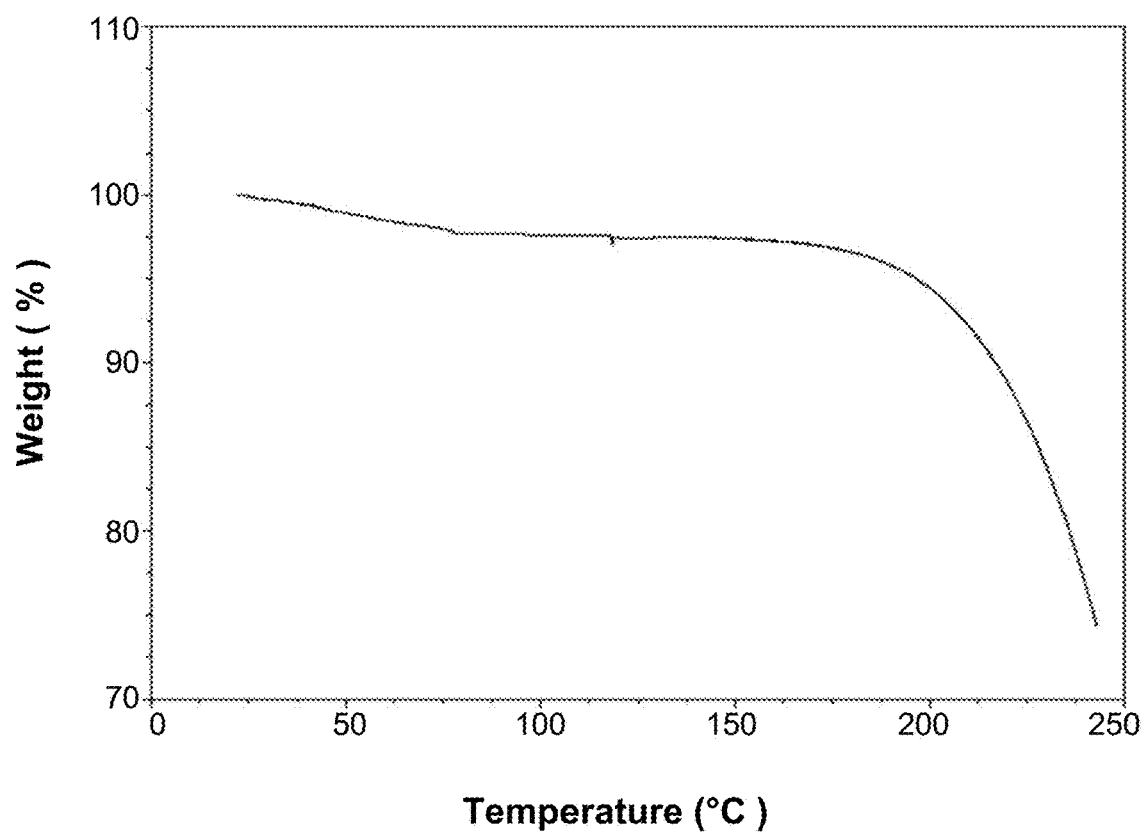
FIG. 8 is the TGA pattern of lasmiditan Form 1 of the present invention.
Figure 9:
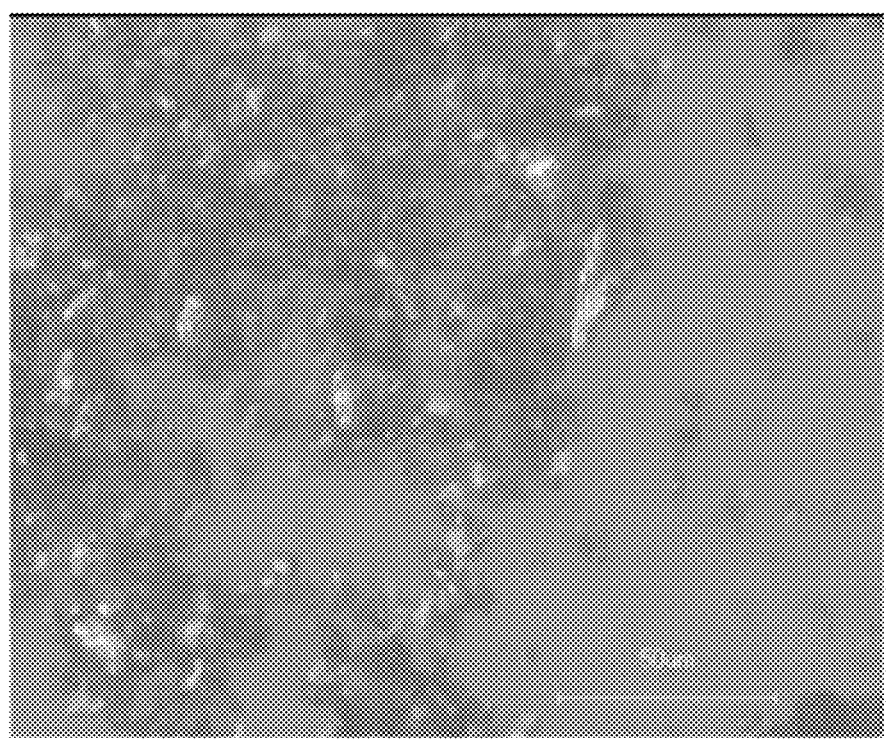
FIG. 9 is the PLM pattern of lasmiditan Form 1 of the present invention.
Figure 10:
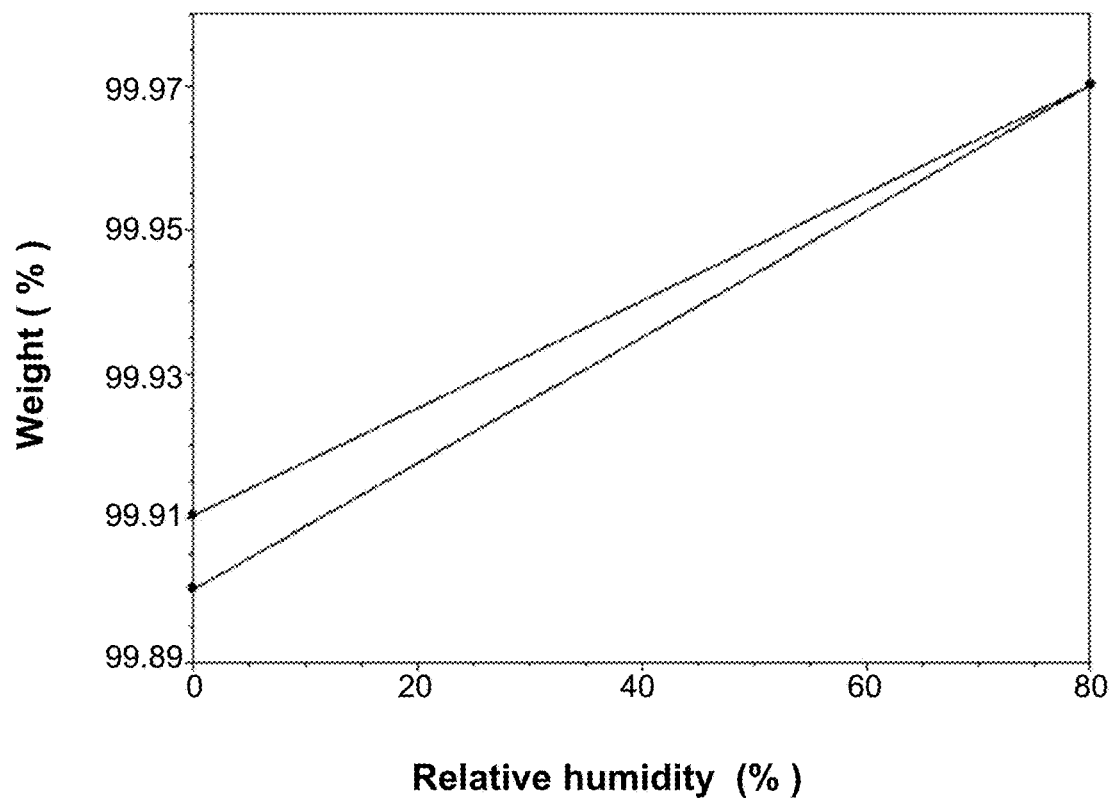
FIG. 10 is the DVS isothermal plot of lasmiditan Form 1 of the present invention.

The XRPD pattern is shown in FIG. 6.
The DSC pattern is shown in FIG. 7.
The TGA pattern is shown in FIG. 8.
The PLM pattern is shown in FIG. 9.
The isothermal sorption plot is shown in FIG. 10.

Example 2

Five hundred miligrams of lasmiditan of Preparation Example 1 was dissolved in water-acetone solution (2.5 mL) containing 10% water, and the solution was volatilized for crystallization at room temperature, after 1 day of volatilization, lasmiditan Form 1 was obtained (474 mg, 93% yield).

Example 3

Two hundred miligrams of lasmiditan of Preparation Example 1 was dissolved in water-acetonitrile solution (4 mL) containing 1% water, and the solution was volatilized for crystallization at room temperature, after 3 days lasmiditan Form 1 was obtained (152 mg, 74% yield).

Example 4

Two hundred miligrams of lasmiditan of Preparation Example 1 was placed in water-ethanol solution (2 mL) containing 80% water to form a suspension, the suspension was stirred for crystallization at room temperature, the suspension was filtered after 1 day of stirring and the solid was vacuum-dried at room temperature for 8 hours, lasmiditan Form 1 was obtained (165 mg, 80% yield).

Example 5

Five hundred miligrams of lasmiditan of Preparation Example 1 was placed in water-tetrahydrofuran solution (0.5 mL) containing 80% water to form a suspension, the suspension was stirred for crystallization at room temperature, it was filtered after 3 days of stirring, and the solid was vacuum-dried at room temperature for 8 hours, lasmiditan Form 1 was obtained (171 mg, 83% yield).

Example 6

Fifty miligrams of lasmiditan of Preparation Example 1 was placed in water-saturated ethyl acetate (5 mL) to form a suspension, the suspension was stirred for crystallization at room temperature, it was filtered after 0.5 days of stirring, and the solid was vacuum-dried at room temperature for 8 hours, lasmiditan Form 1 was obtained (22 mg, 43% yield).

Example 7

Fifty miligrams of lasmiditan of Preparation Example 1 was placed in water (1 mL) to form a suspension, the suspension was stirred for crystallization at room temperature, it was filtered after 3 days of stirring, and the solid was vacuum-dried at room temperature for 8 hours, lasmiditan Form 1 was obtained (34 mg, 66% yield).

The samples prepared in Examples 2-7 have the same or similar XRPD patterns, PLM patterns, DSC patterns, and TGA patterns (not shown) as those of the sample of Examples 1, indicating that the samples of Examples 2-7 and Example 1 have the same crystalline form.

Example 8

Acetone (1.0 mL) and methyl t-butyl ether (1.0 mL) were added in lasmiditan Form 1 (200 mg) of the present invention to form a suspension, the suspension was stirred for crystallization at room temperature, the suspension was filtered after 1 day of stirring, and the solid was vacuum-dried at room temperature for 8 hours, lasmiditan Form 2 was obtained (174 mg, 87% yield).

Figure 11:
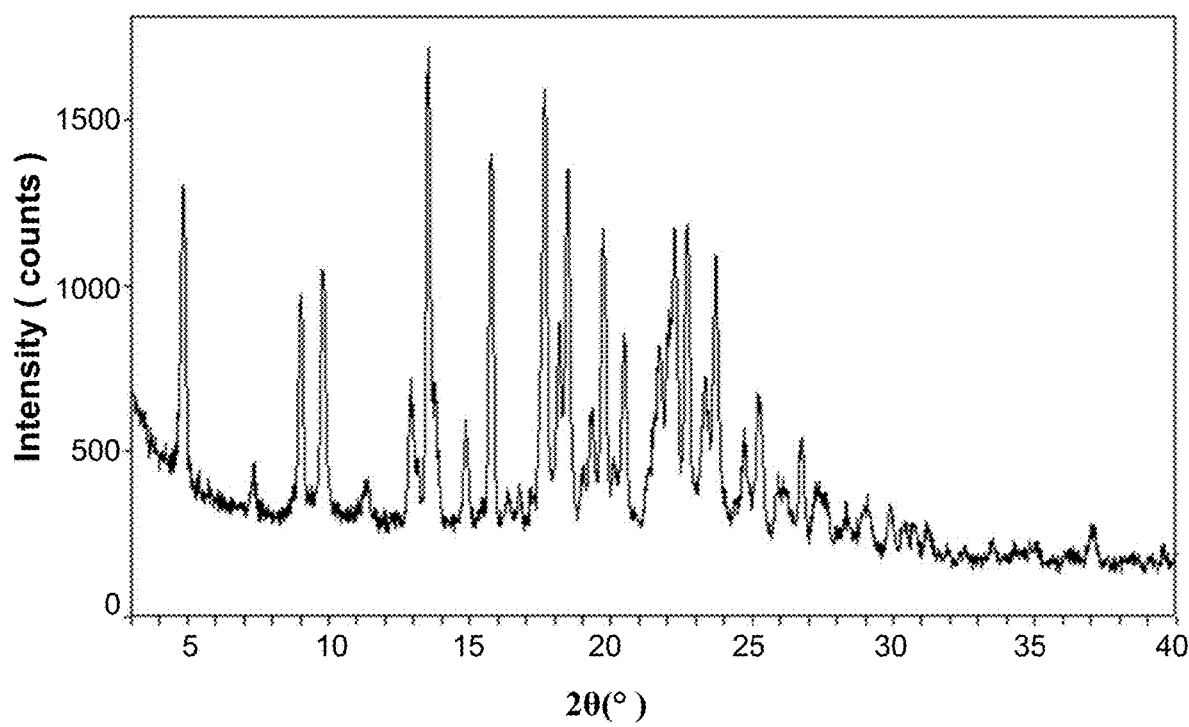
FIG. 11 is the XRPD pattern of lasmiditan Form 2 of the present invention.
Figure 12:
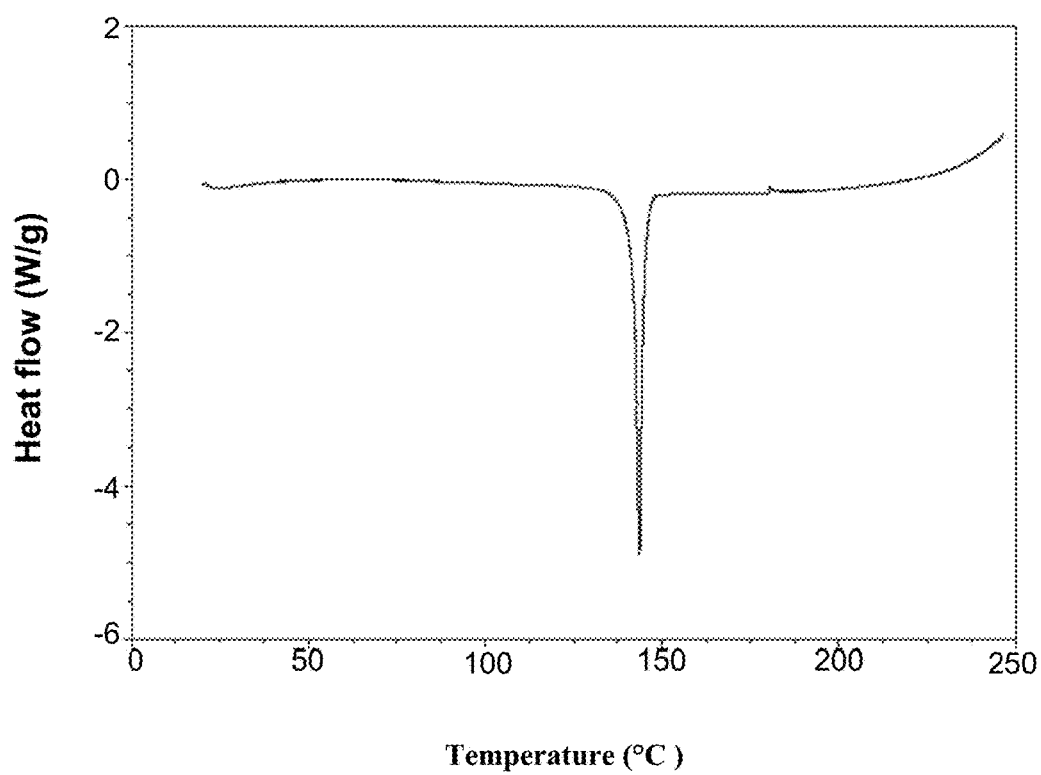
FIG. 12 is the DSC pattern of lasmiditan Form 2 of the present invention.
Figure 13:
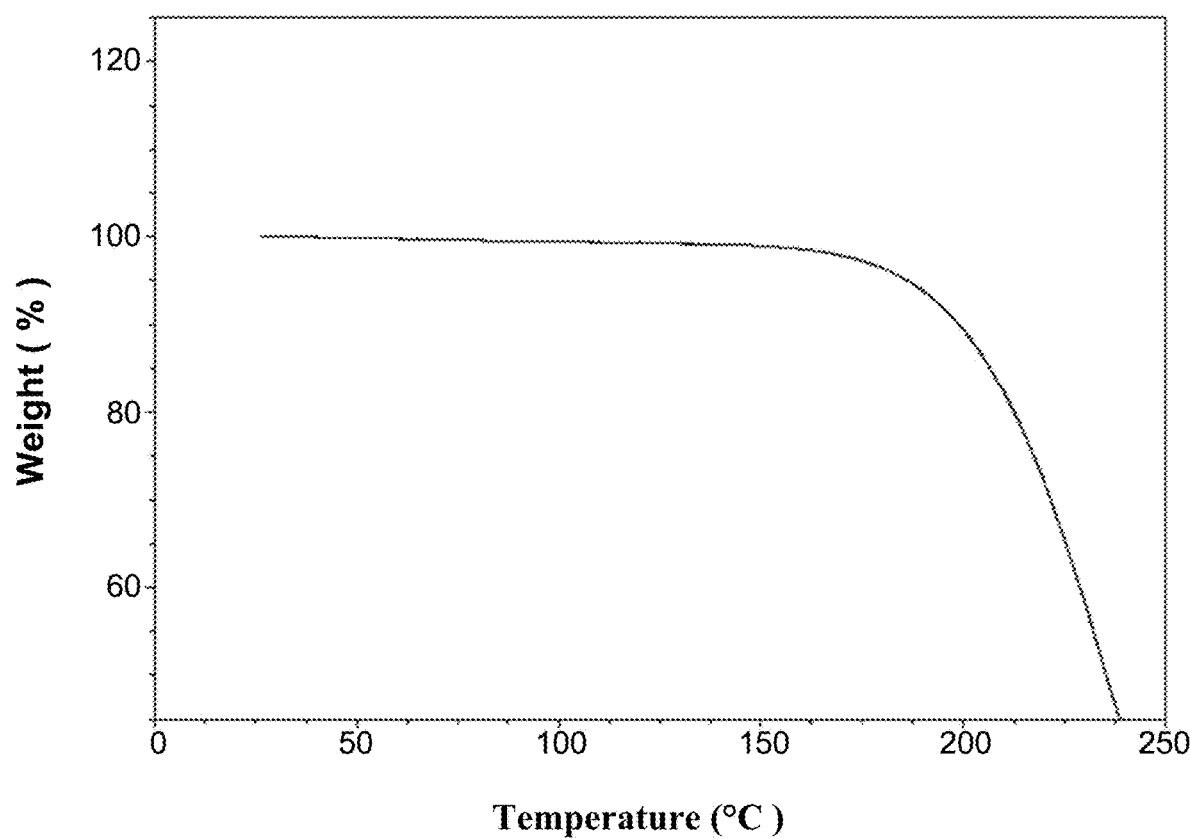
FIG. 13 is the TGA pattern of lasmiditan Form 2 of the present invention.
Figure 14:
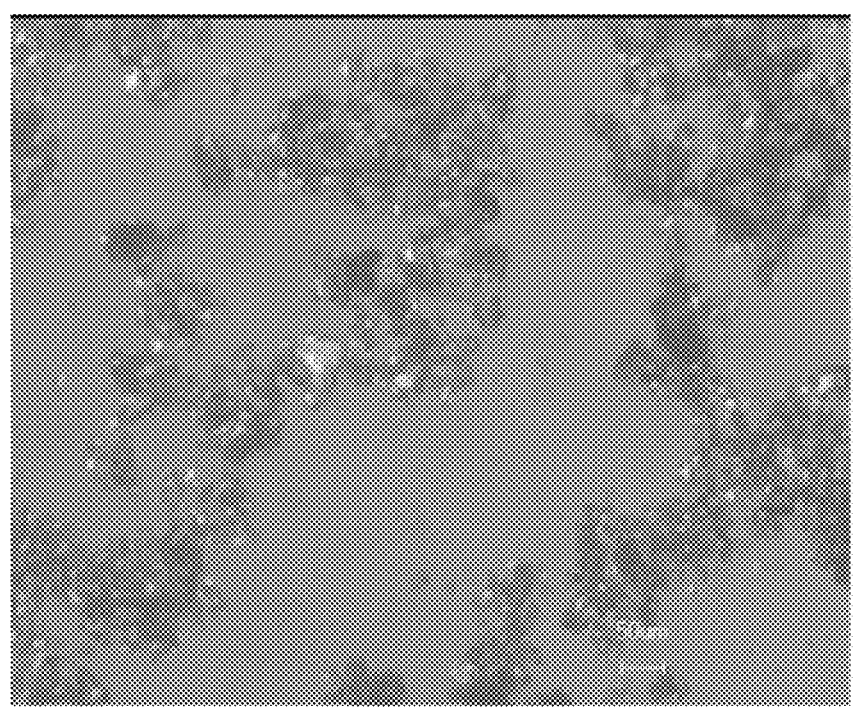
FIG. 14 is the PLM pattern of lasmiditan Form 2 of the present invention.
Figure 15:
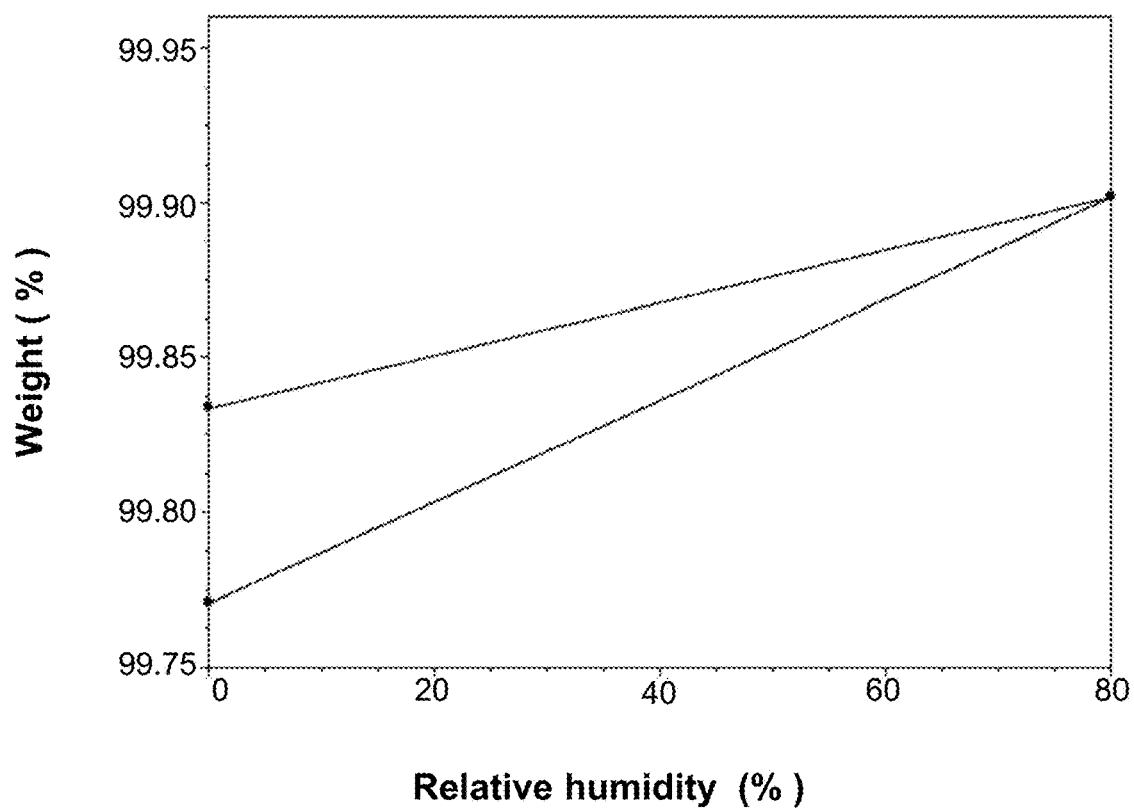
FIG. 15 is the isothermal sorption curve of Lasmiditan Form 2 of the present invention.
Figure 16:
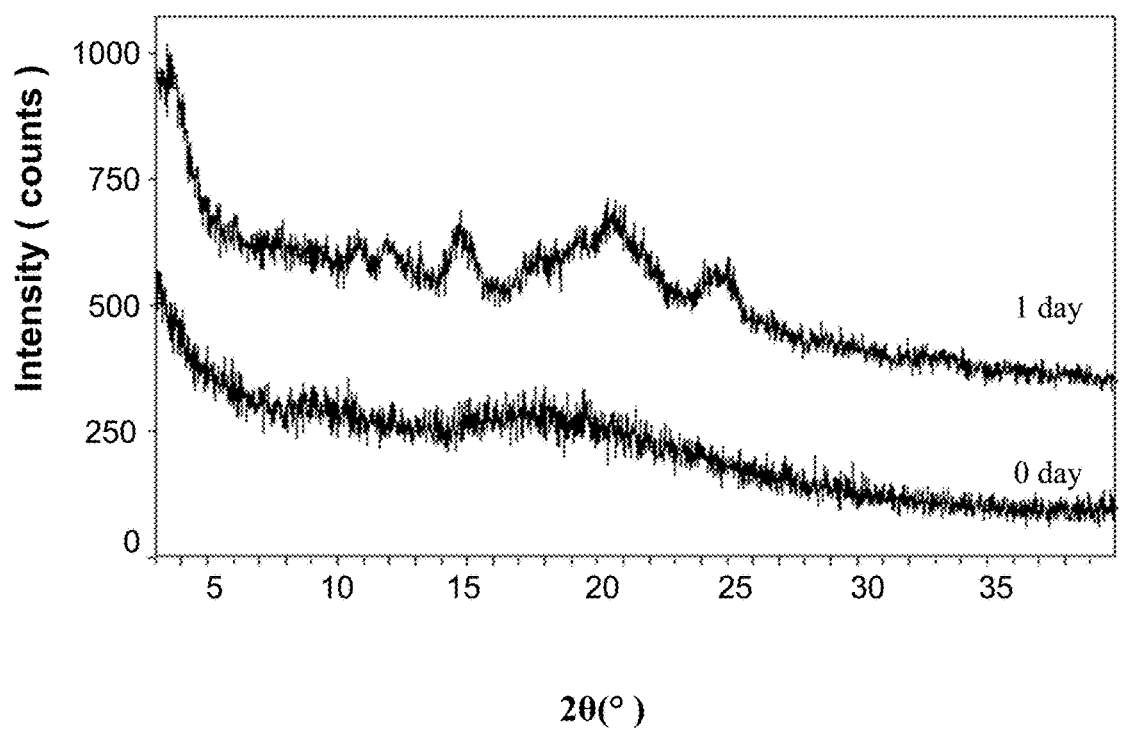
FIG. 16 is the XRPD comparison pattern of stability test of lasmiditan amorphous prepared according to CN100352817C.
Figure 17:
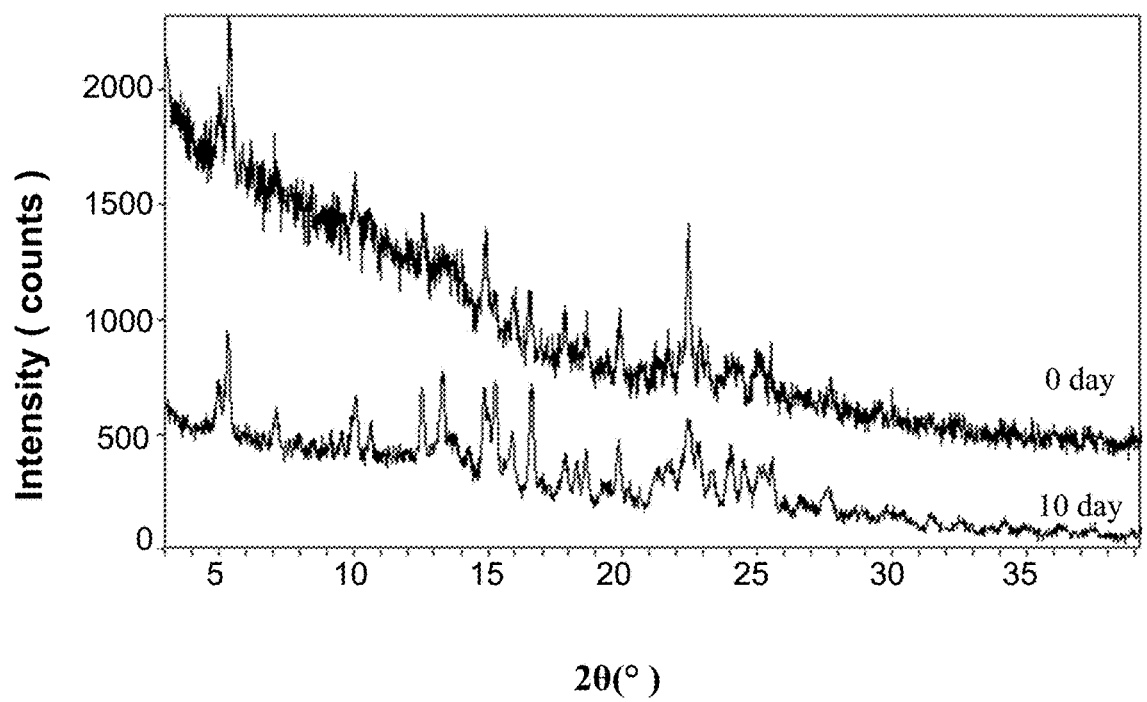
FIG. 17 is the XRPD comparison pattern of stability test of lasmiditan Form 1 of the present invention.
Figure 18:
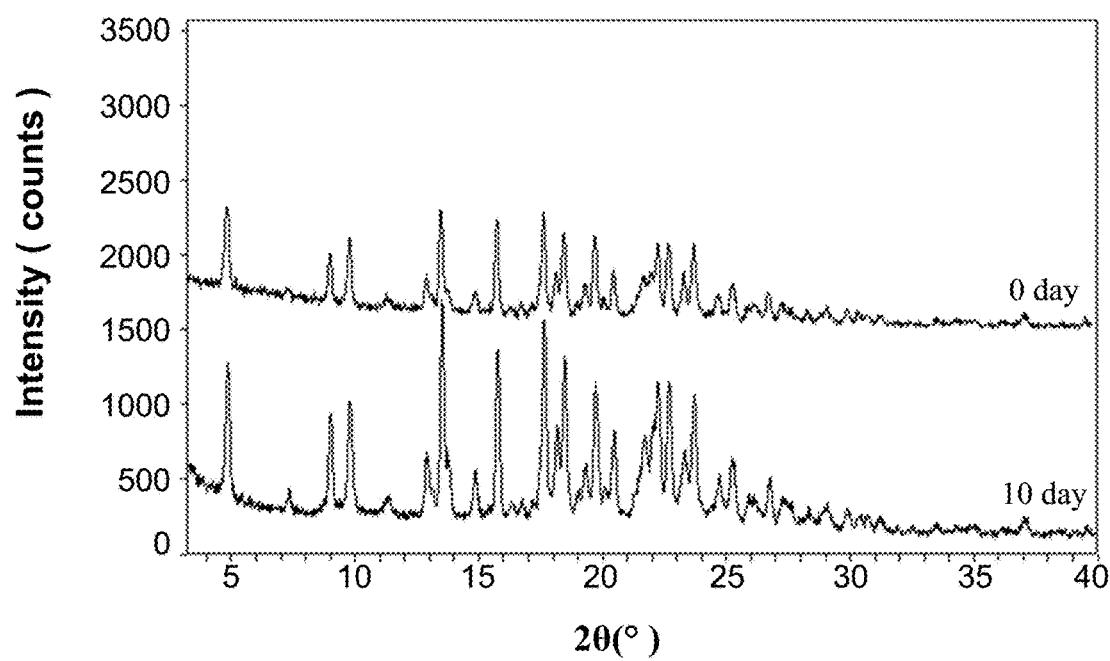
FIG. 18 is the XRPD comparison pattern of stability test of lasmiditan Form 2 of the present invention.

The XRPD pattern is shown in FIG. 11.
The DSC pattern is shown in FIG. 12.
The TGA pattern is shown in FIG. 13.
The PLM pattern is shown in FIG. 14.
The isothermal sorption plot is shown in FIG. 15.

Example 9

Five hundred miligrams of lasmiditan of Preparation Example 1 was added into ethyl acetate (0.5 mL) to form a suspension, the suspension was stirred for crystallization at room temperature, it was filtered after 3 days of stirring, and the solid was vacuum-dried at room temperature for 8 hours, lasmiditan Form 2 was obtained (325 mg, 65% yield).

Example 10 n-Heptane (4.5 mL) and isopropanol (0.5 mL) were added to lasmiditan Form 1 (50 mg) of the present invention to form a suspension, the suspension was filtered after 7 days of stirring, and the solid was vacuum-dried at room temperature for 8 hours, lasmiditan Form 2 was obtained (37 mg, 74% yield).

Example 11

Lasmiditan Form 2 can be obtained by replacing the solvent in Example 10 with the solvent in the following Table.

| Number | Solvent 1 | Solvent 2 |
| --- | --- | --- |
| Experiment 1 | Methanol | Isopropyl ether |
| Experiment 2 | Methyl formate | Hexane |
| Experiment 3 | Methyl ethyl ketone | Ether |
| Experiment 4 | Propyl propionate | n-octane |
| Experiment 5 | 3-pentanone | Methyl tert-butyl ether |
| Experiment 6 | n-butanol | n-heptane |

The samples prepared in Examples 9-11 have the same or similar XRPD patterns, PLM patterns, DSC patterns, TGA patterns (not shown) as those of the sample of Examples 8, indicating that the samples of Examples 9-11 and the sample of Example 8 have the same crystalline form.

Example 12

Fifty miligrams of lasmiditan of Preparation Example 1 was dissolved in ethanol (0.5 mL), then polyethylene glycol 4000 (0.5 mg) was added into the mixture ultrasound was applied to facilitate dissolution. The solution was volatilized to dryness at 40° C. to obtain lasmiditan Form 3 (48 mg, 96% yield).

Figure 39:
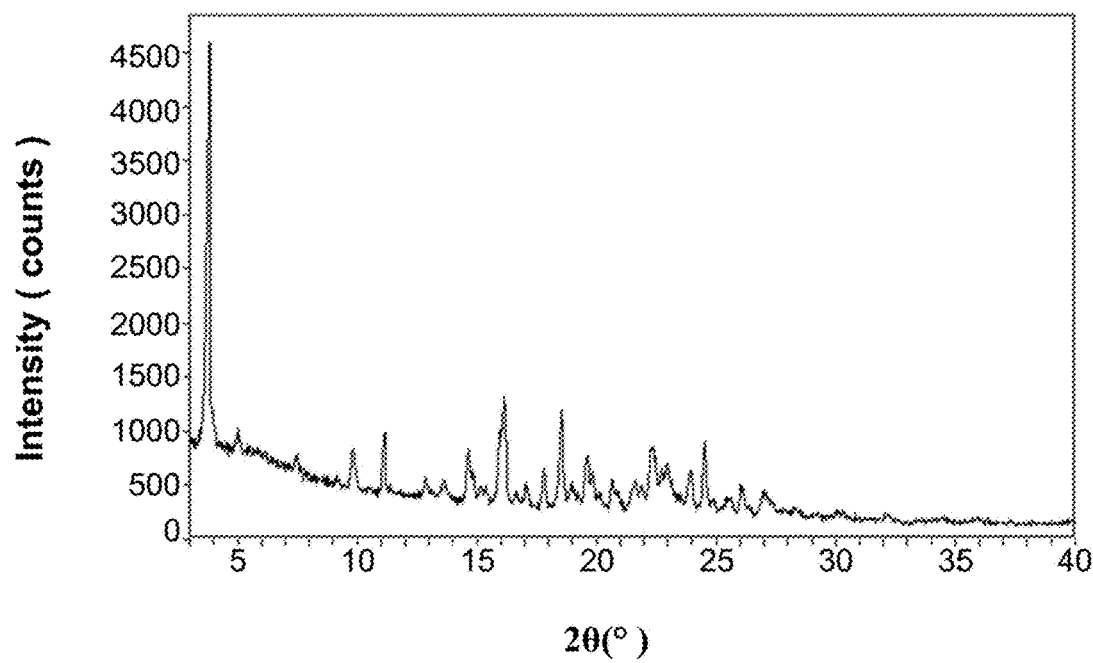
FIG. 39 is the XRPD pattern of lasmiditan Form 3 of the present invention.
Figure 40:
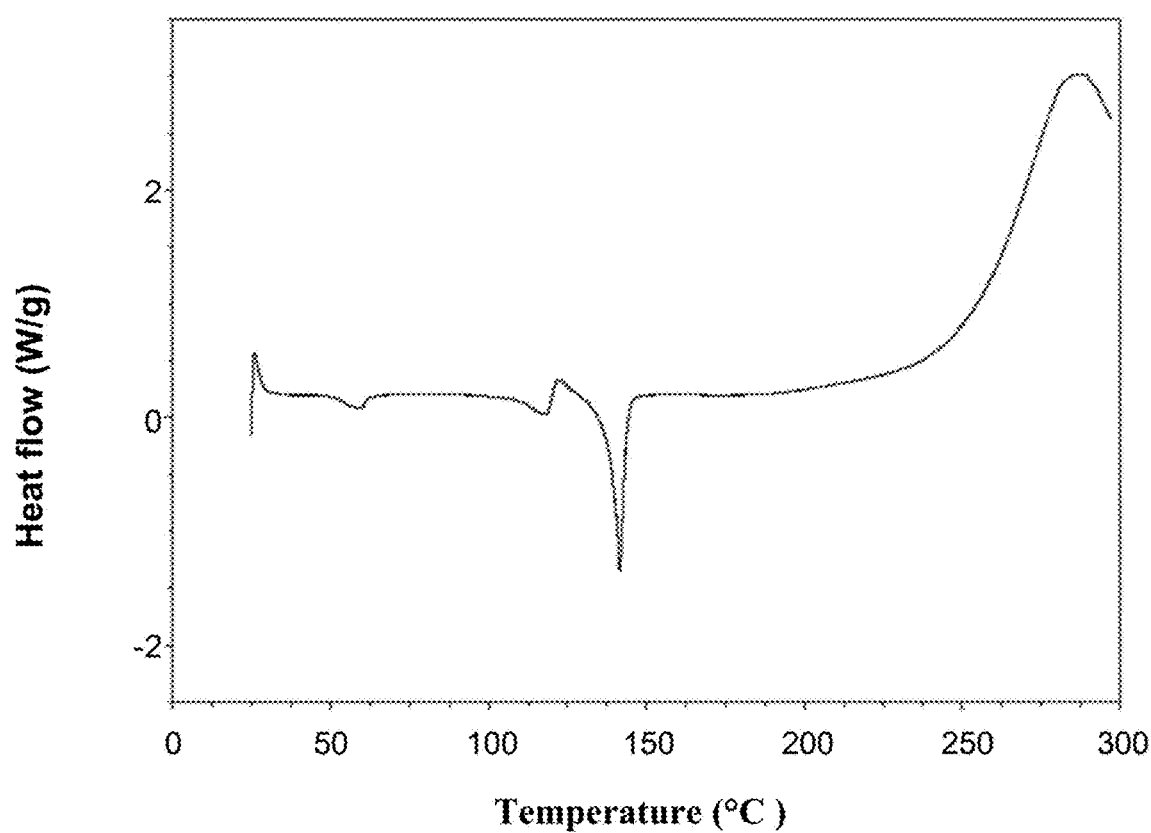
FIG. 40 is the DSC pattern of lasmiditan Form 3 of the present invention.
Figure 41:
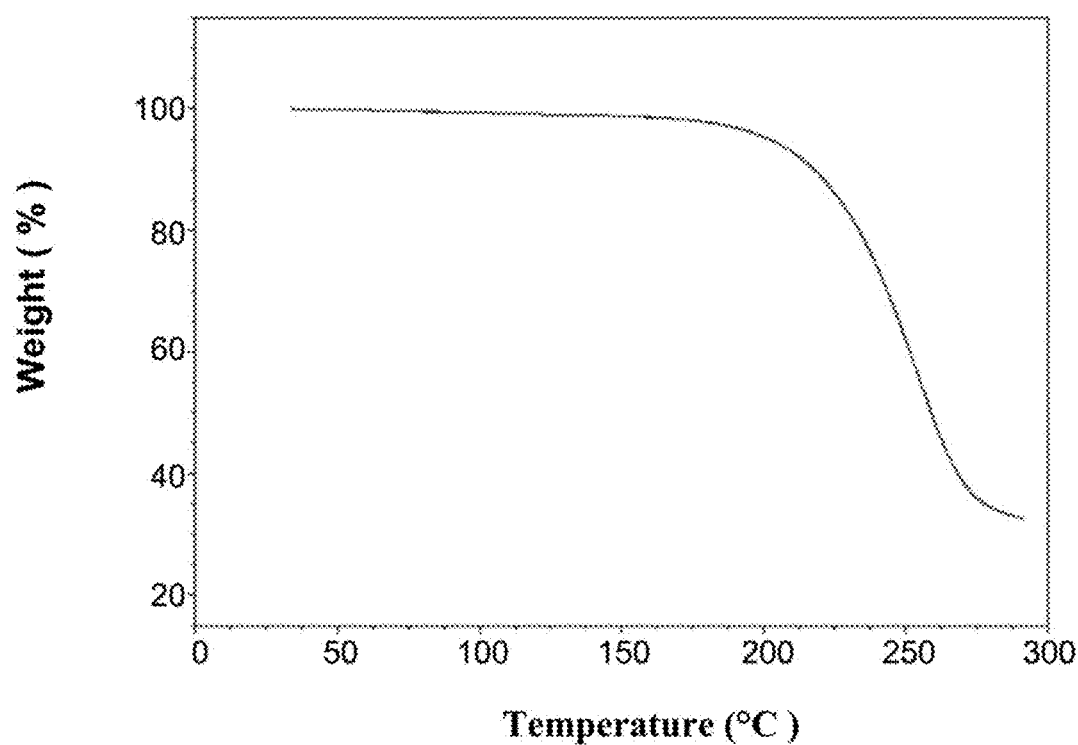
FIG. 41 is the TGA pattern of lasmiditan Form 3 of the present invention.
Figure 42:
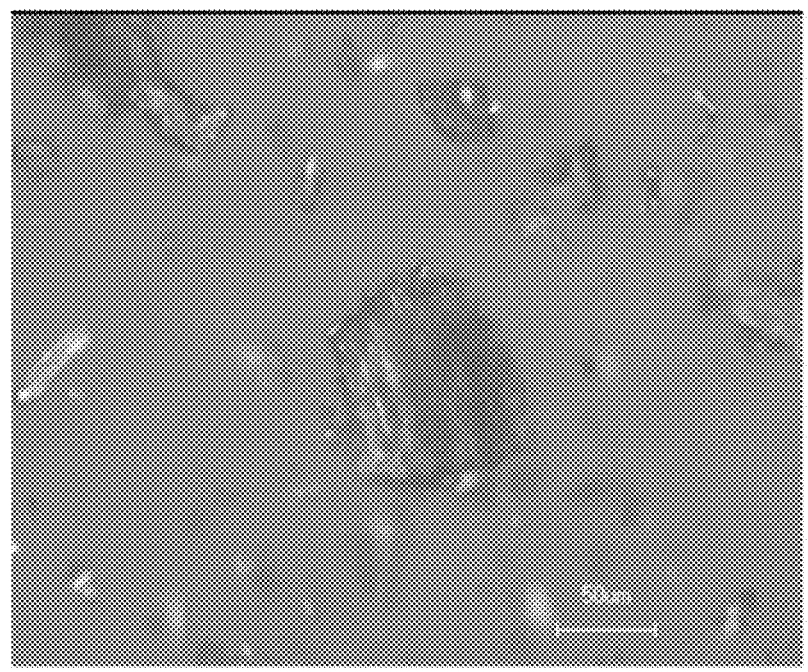
FIG. 42 is the PLM pattern of lasmiditan Form 3 of the present invention.
Figure 43:
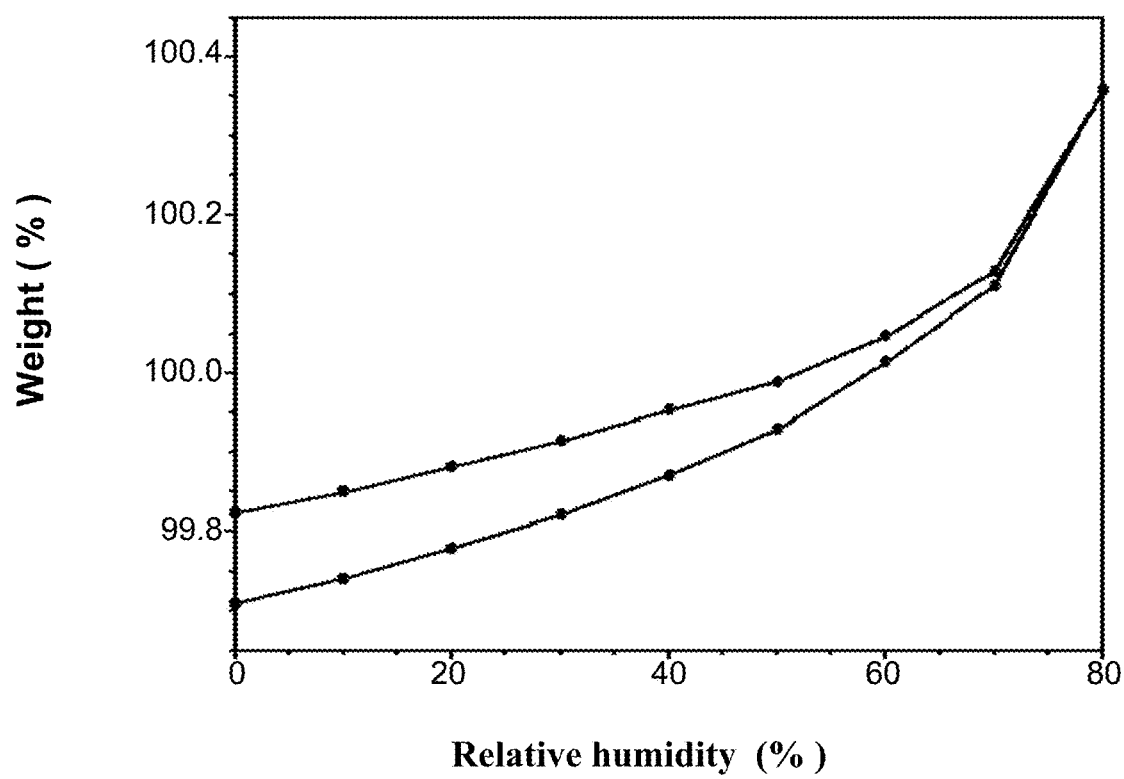
FIG. 43 is the isothermal sorption plot of lasmiditan Form 3 of the present invention.
Figure 44:
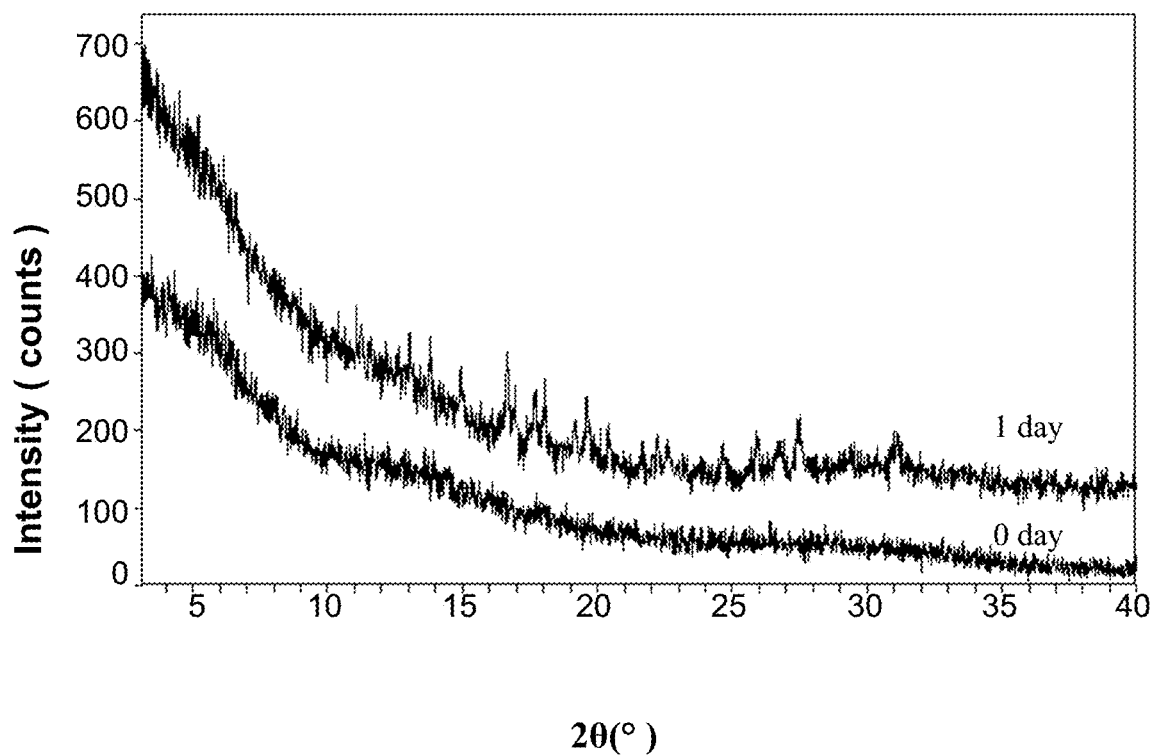
FIG. 44 is the XRPD comparison pattern of stability test of lasmiditan hydrochloride amorphous prepared according to CN100352817C.
Figure 45:
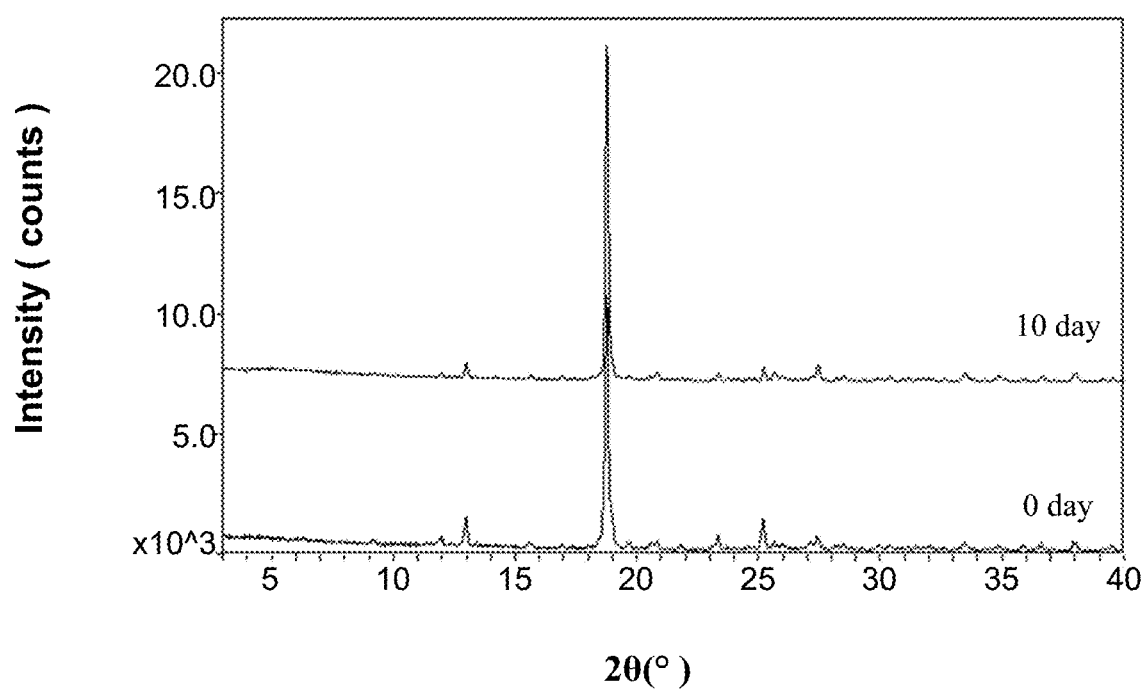
FIG. 45 is the XRPD comparison pattern of stability test of lasmiditan hydrochloride Form A of the present invention.
Figure 46:
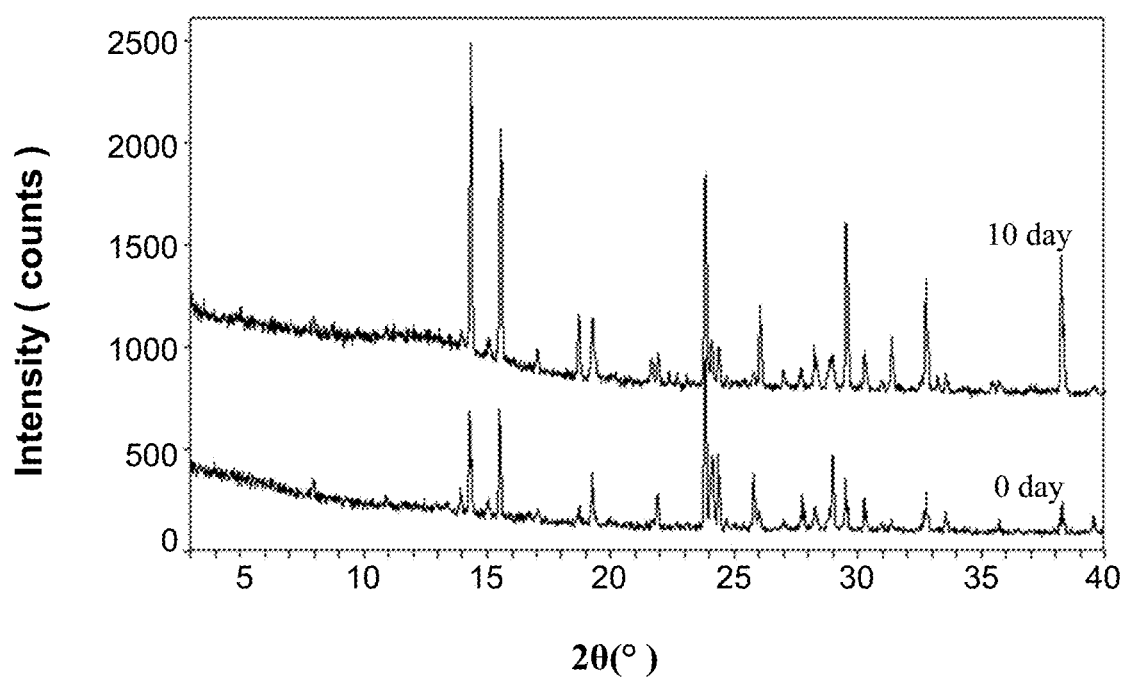
FIG. 46 is the XRPD comparison pattern of stability test of lasmiditan hydrochloride Form B of the present invention.
Figure 47:
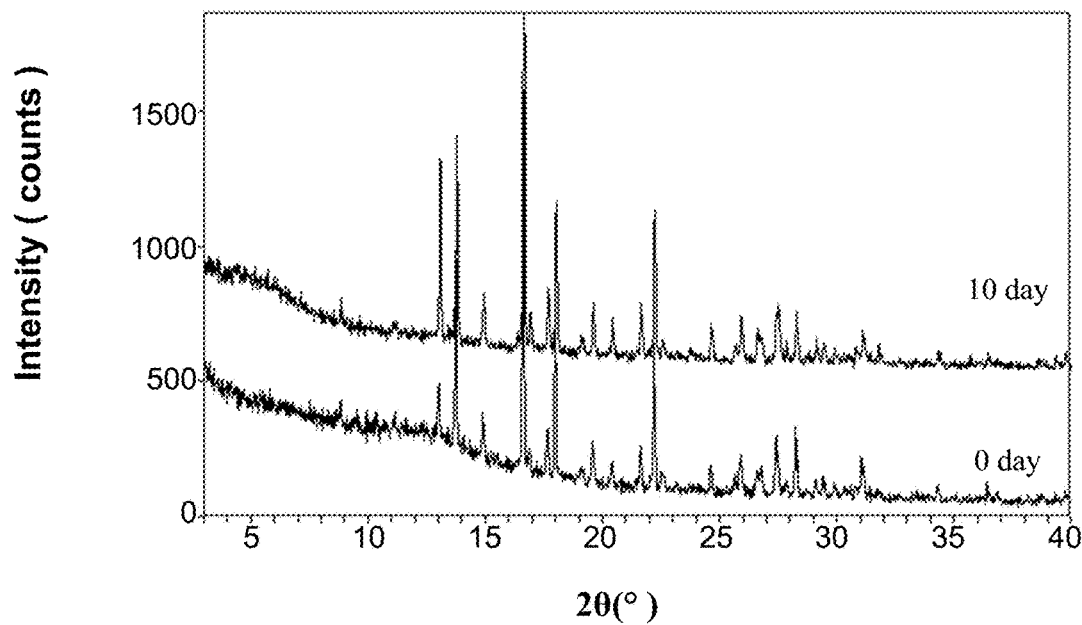
FIG. 47 is the XRPD comparison pattern of stability test of lasmiditan hydrochloride Form C of the present invention.
Figure 48:
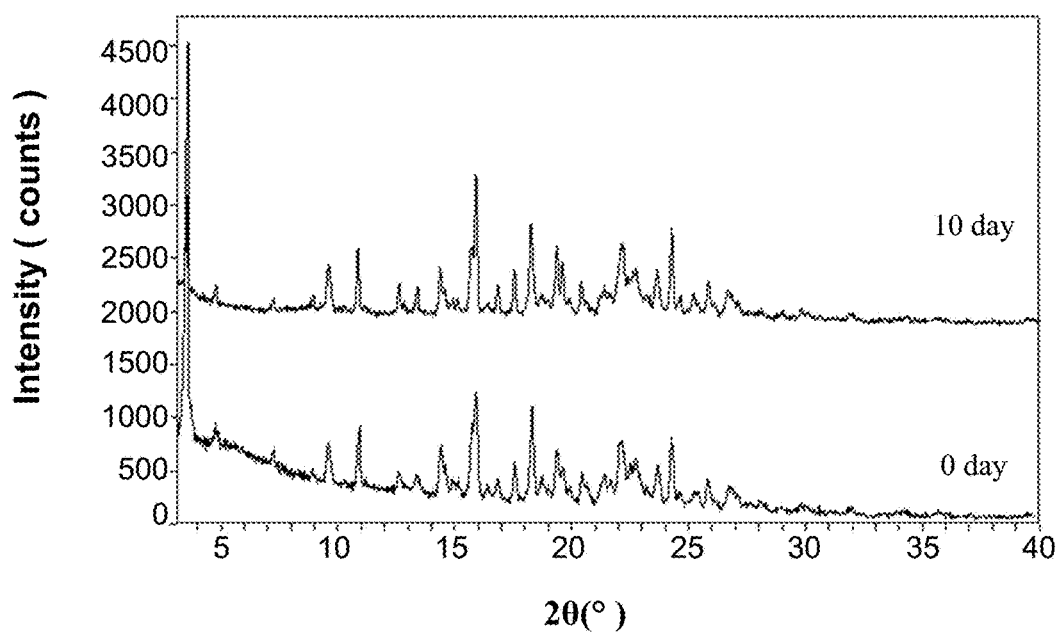
FIG. 48 is the XRPD comparison pattern of stability test of lasmiditan hydrochloride Form 3 of the present invention.

The XRPD pattern is shown in FIG. 39.
The DSC pattern is shown in FIG. 40.
The TGA pattern is shown in FIG. 41.
The PLM pattern is shown in FIG. 42.
The isothermal adsorption plot is shown in FIG. 43.

Example 13

Five hundred miligrams of lasmiditan of Preparation Example 1 was dissolved in methanol (10 mL), and then polyethylene glycol 4000 (50 mg) was added, ultrasound was applied to facilitate dissolution, and the solution was volatilized to dryness at 40° C. to obtain lasmiditan Form 3 (460 mg, 92% yield).

Example 14

Four hundred miligrams of lasmiditan of Preparation Example 1 was dissolved in n-butanol (5 mL), then polyethylene glycol 4000 (20 mg) was added, ultrasound was applied to facilitate dissolution, and the solution was volatilized to dryness at 40° C. to obtain lasmiditan Form 3 (340 mg, 85% yield).

Example 15

Twenty miligrams of lasmiditan of Preparation Example 1 was dissolved in isopropyl ether (10 mL), the solution was volatilized to dryness at room temperature to obtain lasmiditan Form 3 (14 mg, 70% yield).

Example 16

Two hundred miligram of lasmiditan of Preparation Example 1 was dissolved in isopropyl acetate (4 mL), the solution was volatilized to dryness at room temperature to obtain lasmiditan Form 3 (155 mg, 78% yield).

Example 17

Fifty miligrams of lasmiditan of Preparation Example 1 was dissolved in toluene (2 mL), the solution was volatilized to dryness at room temperature to obtain lasmiditan Form 3 (40 mg, 80% yield).

The samples prepared in Examples 13-17 have the same or similar XRPD patterns, PLM patterns, DSC patterns, and TGA patterns (not shown) as those of the sample of Examples 12, indicating that the samples of Examples 13-17 and the sample of Example 12 have the same crystalline form.

Example 18

Fifty miligrams of lasmiditan hydrochloride of Preparation Example 2 was dissolved in ethanol (2 mL), the solution was volatilized to dryness at room temperature to obtain lasmiditan hydrochloride Form A (46 mg, 92% yield).

Figure 22:
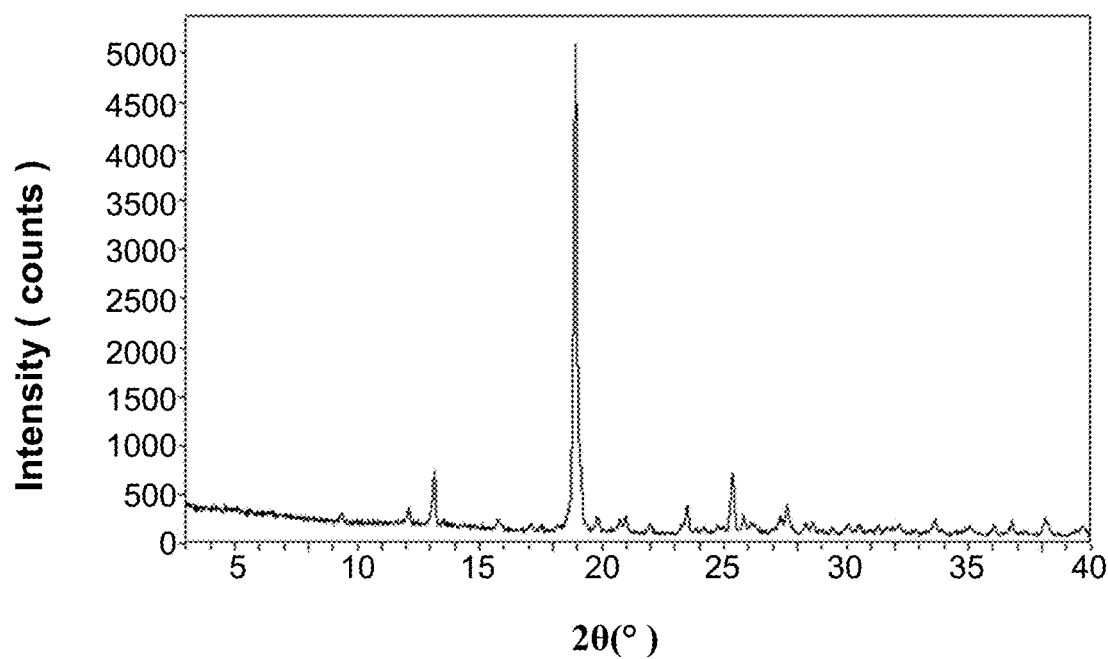
FIG. 22 is the XRPD pattern of lasmiditan hydrochloride Form A of the present invention.
Figure 23:
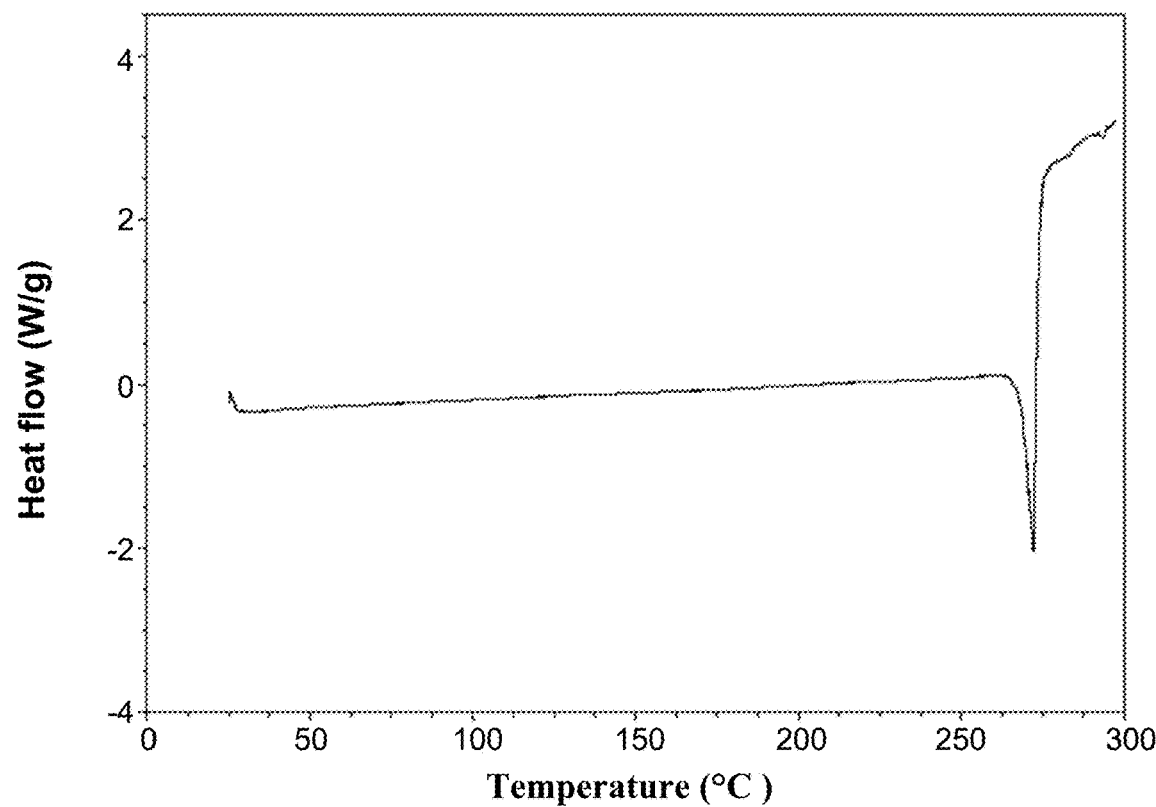
FIG. 23 is the DSC pattern of lasmiditan hydrochloride Form A of the present invention.
Figure 24:
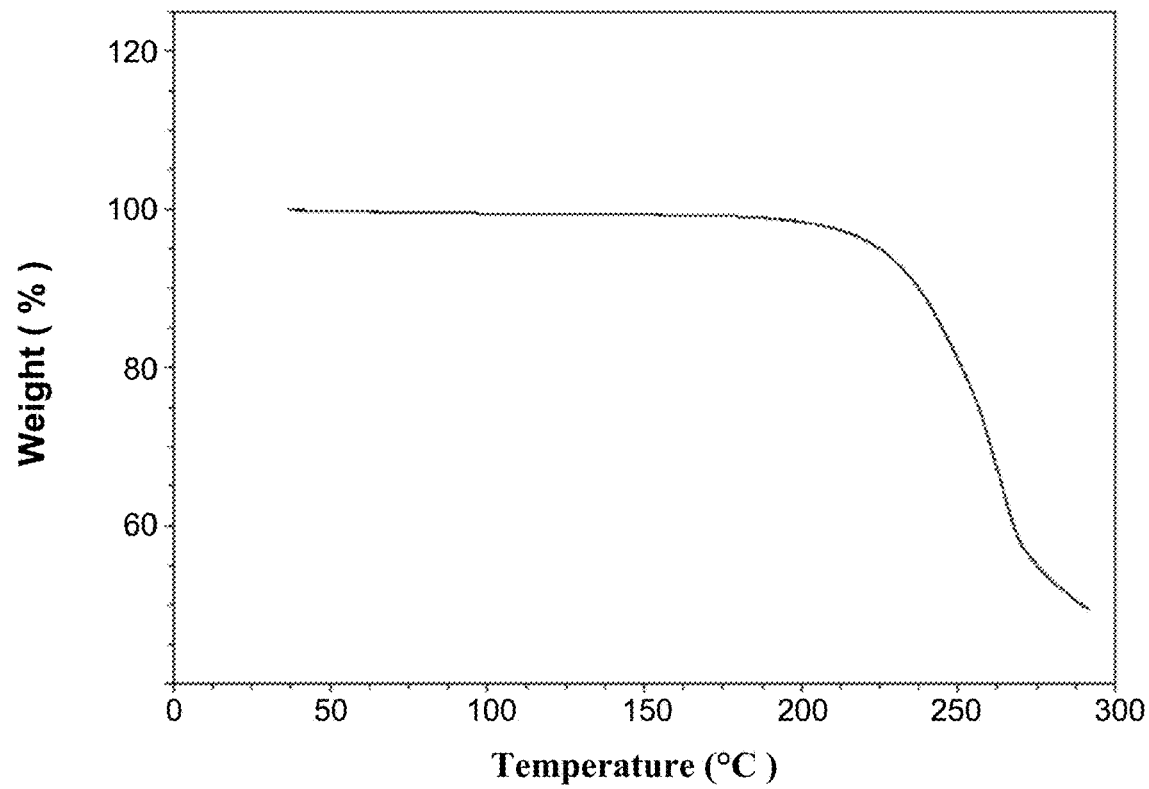
FIG. 24 is the TGA pattern of lasmiditan hydrochloride Form A of the present invention.
Figure 25:
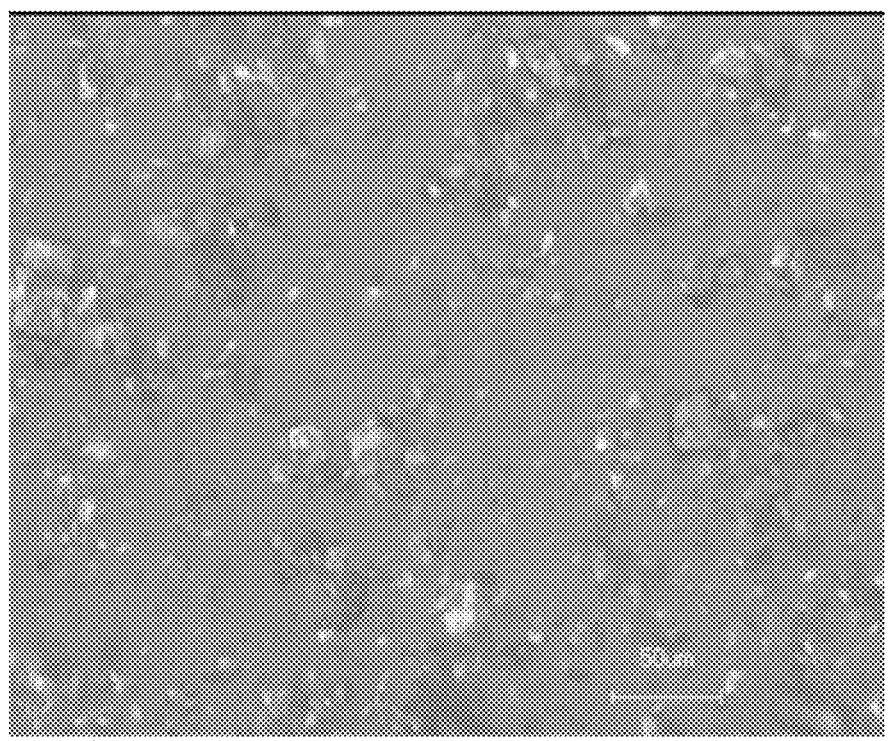
FIG. 25 is the PLM pattern of lasmiditan hydrochloride Form A of the present invention.
Figure 26:
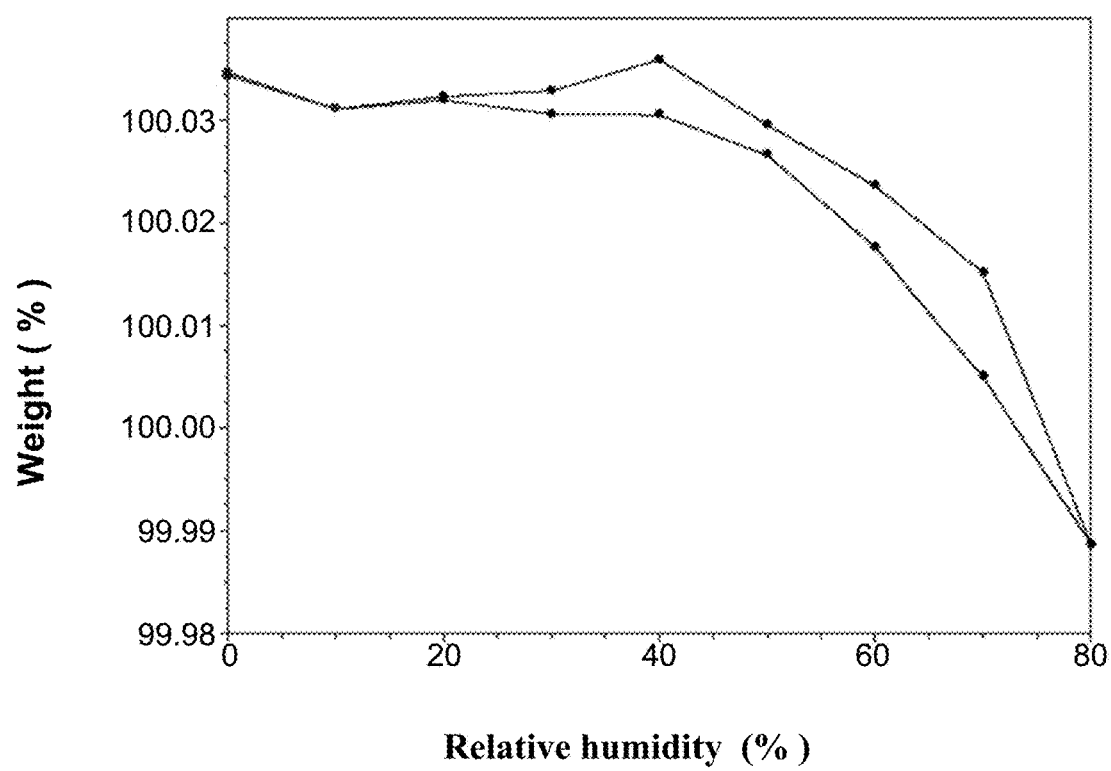
FIG. 26 is the isothermal sorpation plot of lasmiditan hydrochloride Form A of the present invention.

The XRPD pattern is shown in FIG. 22.
The DSC pattern is shown in FIG. 23.
The TGA pattern is shown in FIG. 24.
The PLM pattern is shown in FIG. 25.
The isothermal sorption plot is shown in FIG. 26.

Example 19

Twenty miligrams of lasmiditan hydrochloride of Preparation Example 2 was dissolved in nitromethane (4 mL), the solution was volatilized to dryness at room temperature to obtain lasmiditan hydrochloride Form A (17 mg, 85% yield).

Example 20

Lasmiditan hydrochloride Form A was obtained by replacing the solvent of Example 19 with the solvent in the following Table.

| Number | Solvent 1 | Solvent 2 |
| --- | --- | --- |
| Experiment 1 | Methanol | Dichloromethane |
| Experiment 2 | Ethanol | 1,4-dioxane |
| Experiment 3 | Isopropanol | Acetonitrile |
| Experiment 4 | Ethylene glycol | Nitromethane |
| Experiment 5 | Nitromethane | Acetonitrile |
| Experiment 6 | Dichloromethane | Acetonitrile |

Example 21

Five hundred miligrams of lasmiditan hydrochloride of Preparation Example 2 was added into acetone (5 mL) to form a suspension, which was first stirred for crystallization at room temperature, and then was filtered after 3 days of stirring, and the solid was vacuum-dried at room temperature to obtain lasmiditan hydrochloride Form A (425 mg, 85% yield).

Example 22

One hundred milligrams of lasmiditan hydrochloride of Preparation Example 2 was added into acetonitrile (0.5 mL) to form a suspension, which was first stirred for crystallization at room temperature, and then was filtered after 7 days of stirring, and the solid was vacuum-dried at room temperature to obtain lasmiditan hydrochloride Form A (80 mg, 80% yield).

Example 23

Three hundred milligrams of lasmiditan hydrochloride of Preparation Example 2 was added into acetonitrile (3 mL) and acetone (3 mL) to form a suspension, which was first stirred for crystallization at room temperature, and then was filtered after 1 day of stirring, and the solid was vacuum-dried at room temperature to obtain lasmiditan hydrochloride Form A (180 mg, 60% yield).

Example 24

Lasmiditan hydrochloride Form A can be obtained by replacing the solvent in Example 23 with the solvent in the following Table.

| Number | Solvent 1 | Solvent 2 |
| --- | --- | --- |
| Experiment 1 | Methanol | Isopropyl ether |
| Experiment 2 | Ethanol | Toluene |
| Experiment 3 | Isopropanol | Acetone |
| Experiment 4 | 2-Butanol | Methylcyclohexane |
| Experiment 5 | Ethyl acetate | Isopropyl ether |
| Experiment 6 | Tetrahydrofuran | Ethanol |
| Experiment 7 | n-Heptane | Methyl tert-butyl ether |
| Experiment 8 | 1,4-Dioxane | n-Heptane |

The samples prepared in Examples 19-24 have the same or similar XRPD patterns, PLM patterns, DSC patterns, TGA patterns (not shown) as those of the sample of Example 18, indicating that the samples of Examples 19-24 and the sample of Example 18 have the same crystalline form.

Example 25

Fifty milligrams of lasmiditan hydrochloride of Preparation Example 2 was dissolved in water-ethanol solution (0.25 mL) containing 60% water at 45° C., the solution was cooled to and kept at 4° C. for crystallization, after 5 days, it was filtered and the solid was vacuum-dried for 1 hour at room temperature to obtain lasmiditan hydrochloride Form B (32 mg, 59% yield).

Figure 27:
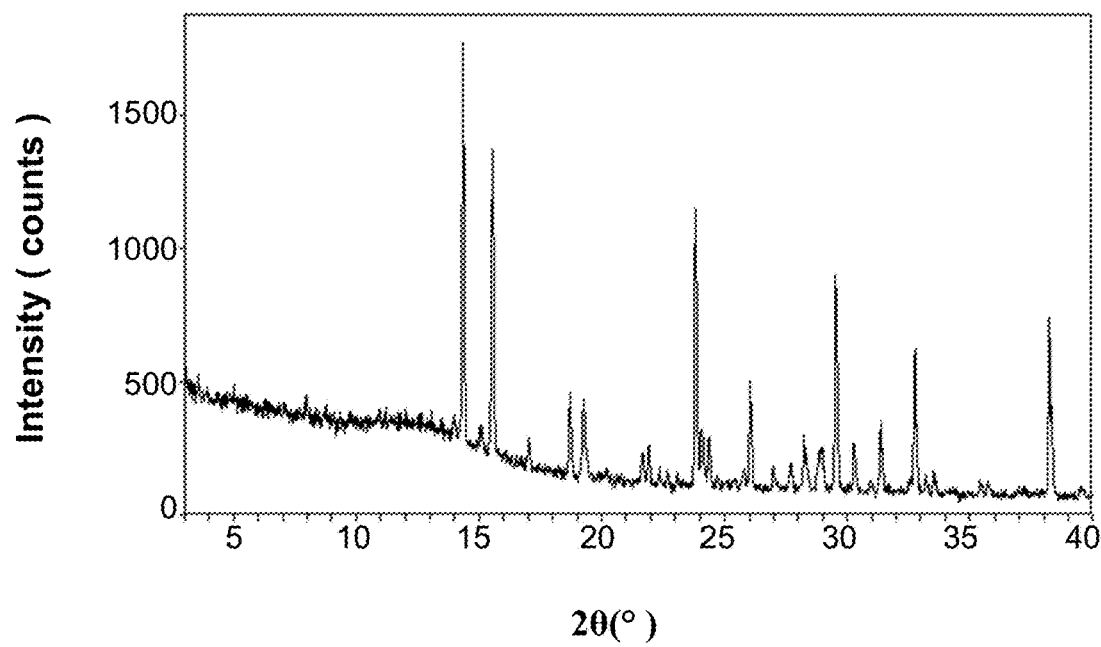
FIG. 27 is the XRPD pattern of lasmiditan hydrochloride Form B of the present invention.
Figure 28:
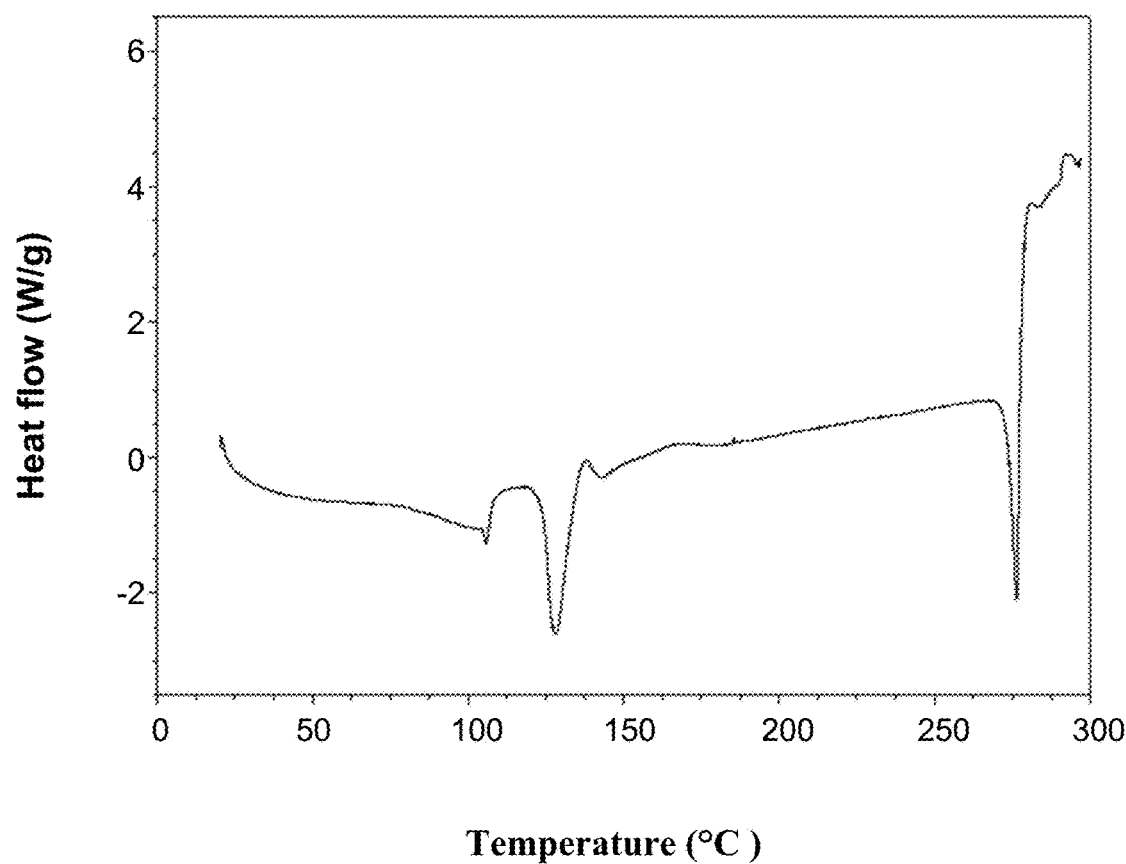
FIG. 28 is the DSC pattern of lasmiditan hydrochloride Form B of the present invention.
Figure 29:
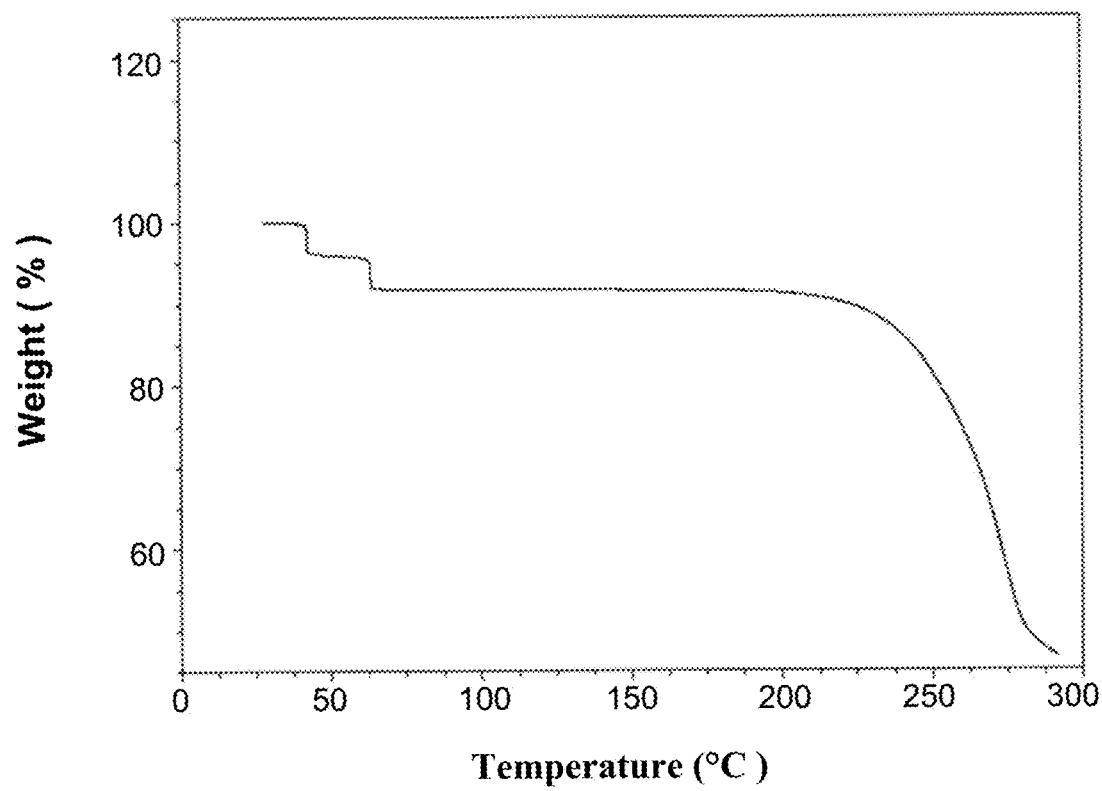
FIG. 29 is the TGA pattern of lasmiditan hydrochloride Form B of the present invention.
Figure 30:
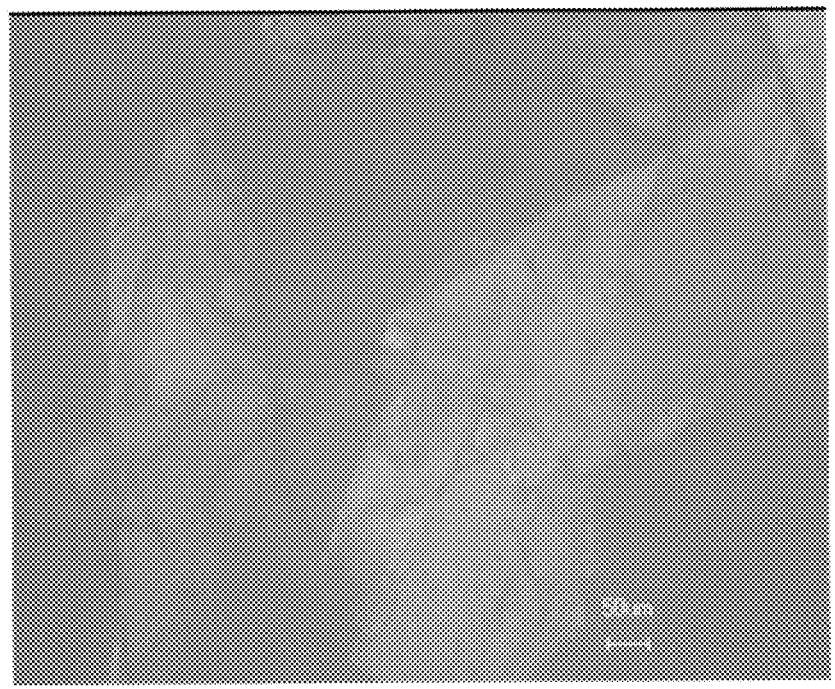
FIG. 30 is the PLM pattern of lasmiditan hydrochloride Form B of the present invention.
Figure 31:
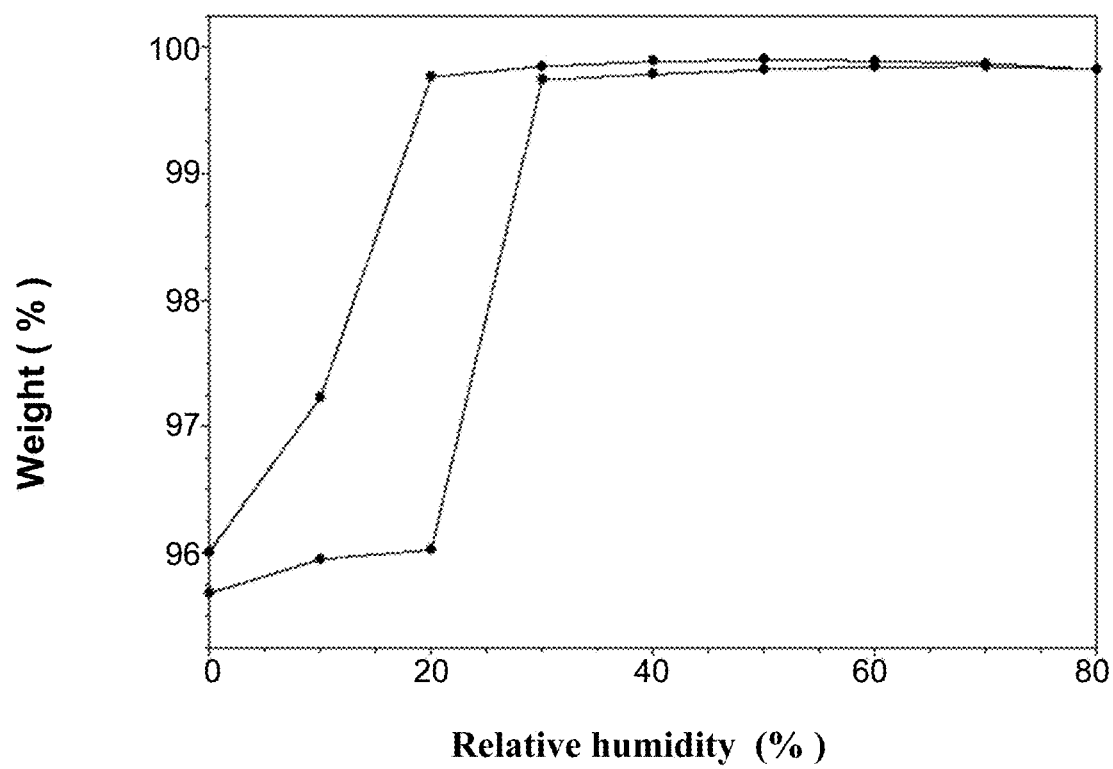
FIG. 31 is the isothermal sorption plot of lasmiditan hydrochloride Form B of the present invention.

Its XRPD pattern is shown in FIG. 27.
Its DSC pattern is shown in FIG. 28.
Its TGA pattern is shown in FIG. 29.
Its PLM pattern is shown in FIG. 30.
Its isothermal sorption plot is shown in FIG. 31.

Example 26

Sixty milligrams of lasmiditan hydrochloride of Preparation Example 2 was dissolved in water (0.6 mL) at 60° C. to form a solution, which was cooled to and kept at 4° C. for 3 days for crystallization, it was then filtered, and the solid was vacuum-dried for 5 hours at room temperature 25° C. to obtain lasmiditan hydrochloride Form B (56 mg, 86% yield).

Example 27

Sixty milligrams of lasmiditan hydrochloride salt of Preparation Example 2 was dissolved in water-ethanol solution (0.60 mL) containing 40% water at 60° C. to form a solution, which was then cooled to and kept at 4° C. for 3 days for crystallization, it was then filtered, and the solid was vacuum-dried 1 h at 40° C. to obtain lasmiditan hydrochloride Form B (30 mg, 46% yield).

Example 28

Lasmiditan hydrochloride Form B can be obtained by replacing the solvent in Example 27 with the solvent in the following Table.

| Number | Solvent 1 | Solvent 2 |
| --- | --- | --- |
| Experiment 1 | Methanol | Water |
| Experiment 2 | Trifluoroethanol | Water |
| Experiment 3 | Isopropanol | Water |
| Experiment 4 | Acetone | Water |
| Experiment 6 | Acetonitrile | Water |

Example 29

Sixty milligrams of lasmiditan hydrochloride of Preparation Example 2 was dissolved in water-ethanol solution (0.40 mL) containing 40% water at 50° C. to form a solution, which was then volatilized to dryness at room temperature to obtain lasmiditan hydrochloride Form B (46 mg, 71% yield).

Example 30

Sixty milligrams of lasmiditan hydrochloride of Preparation Example 2 was dissolved in water-n-propanol solution (0.60 mL) containing 60% water at 50° C. to form a solution, which was volatilized to dryness at room temperature to obtain lasmiditan hydrochloride Form B (40 mg, 67% yield).

Example 31

Lasmiditan hydrochloride Form B can be obtained by replacing the solvent in Example 30 with the solvent in the following Table.

| Number | Solvent 1 | Solvent 2 |
| --- | --- | --- |
| Experiment 1 | None | Water |
| Experiment 2 | Methanol | Water |
| Experiment 3 | Trifluoroethanol | Water |
| Experiment 4 | Isopropanol | Water |
| Experiment 5 | Acetone | Water |
| Experiment 6 | Acetonitrile | Water |

The samples prepared in Examples 26-31 have the same or similar XRPD patterns, PLM patterns, DSC patterns, TGA patterns (not shown) as those of the sample of Example 25, it indicates that the samples of Examples 26-31 and the sample of Example 25 have the same crystalline form.

Example 32

Figure 32:
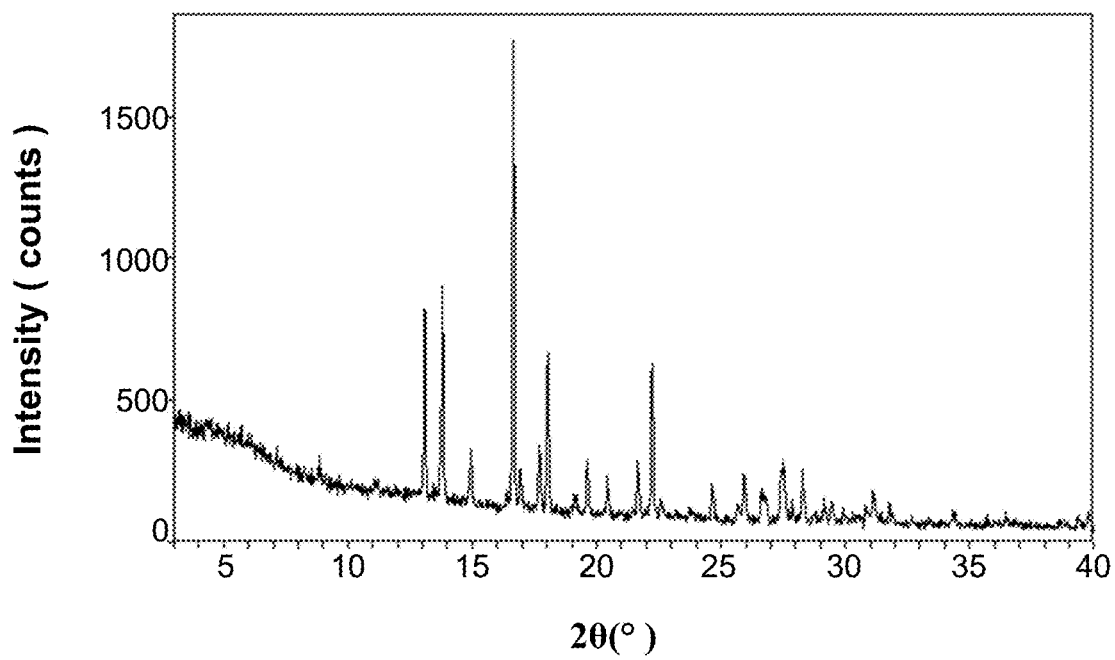
FIG. 32 is the XRPD pattern of lasmiditan hydrochloride Form C of the present invention.
Figure 33:
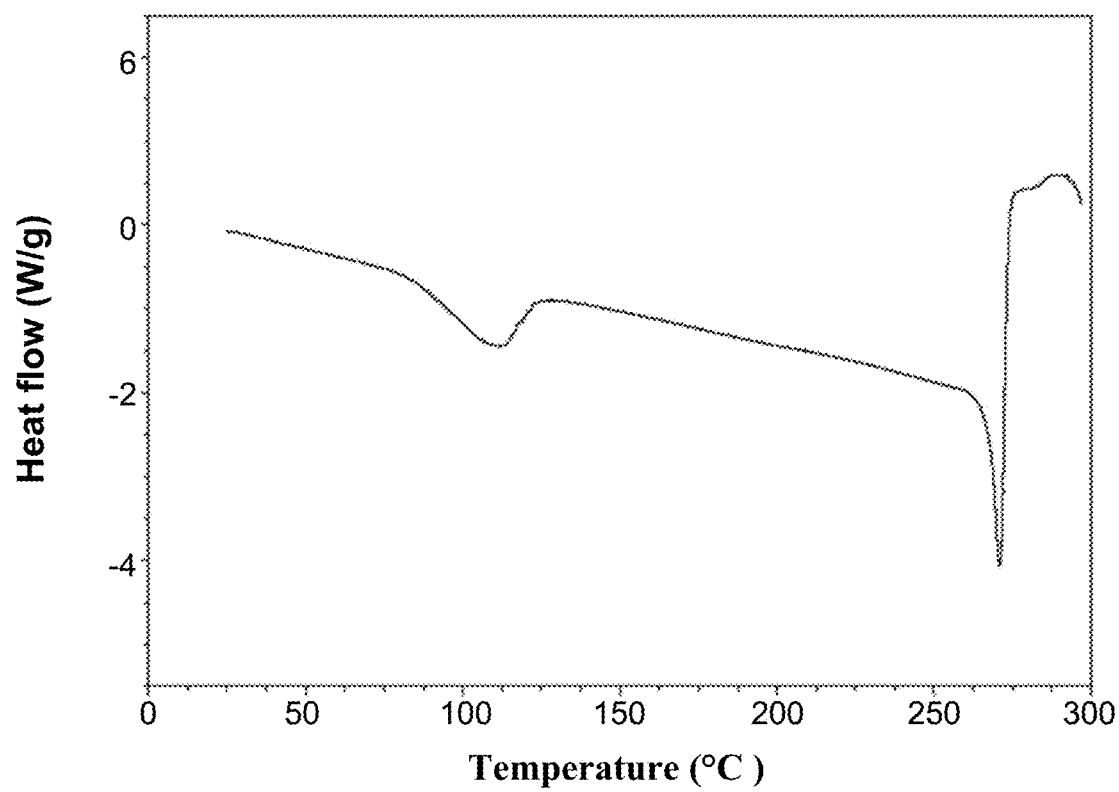
FIG. 33 is the DSC pattern of lasmiditan hydrochloride Form C of the present invention.
Figure 34:
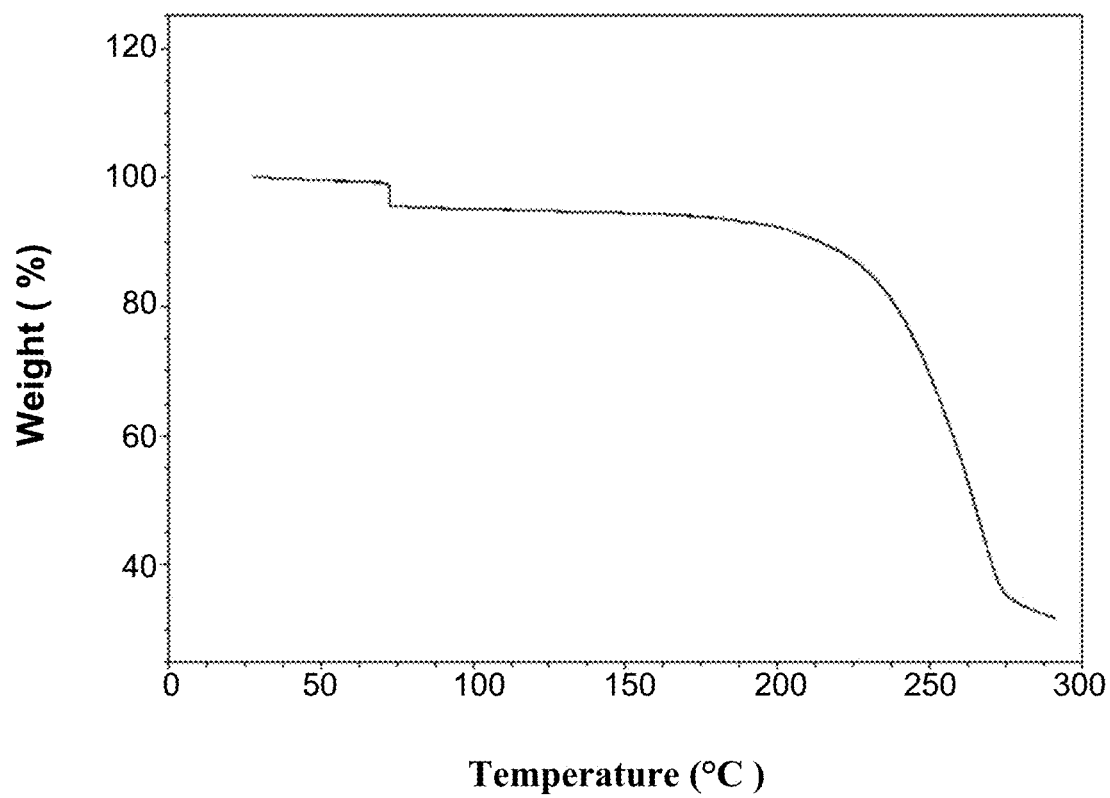
FIG. 34 is the TGA pattern of lasmiditan hydrochloride Form C of the present invention.
Figure 35:
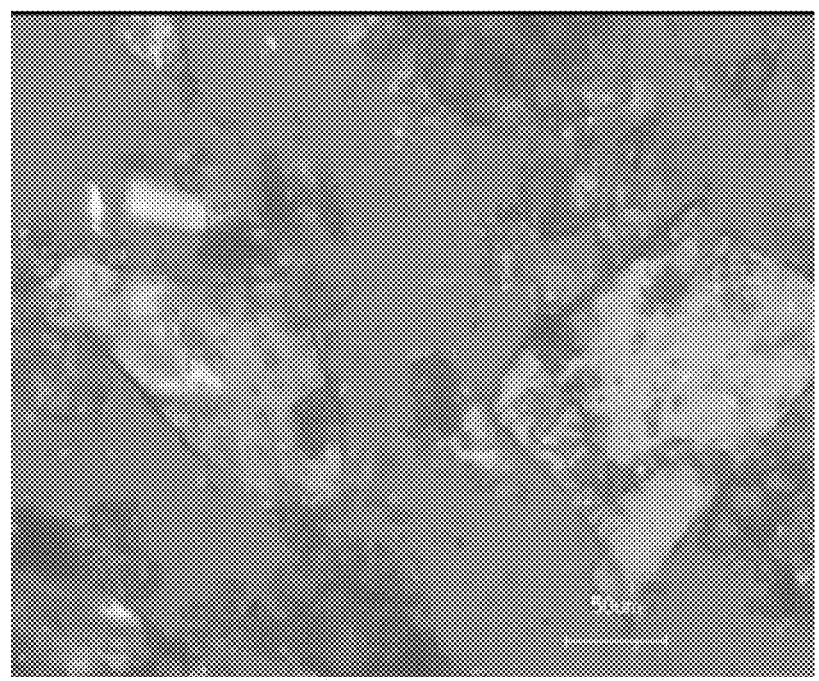
FIG. 35 is the PLM pattern of lasmiditan hydrochloride Form C of the present invention.
Figure 36:
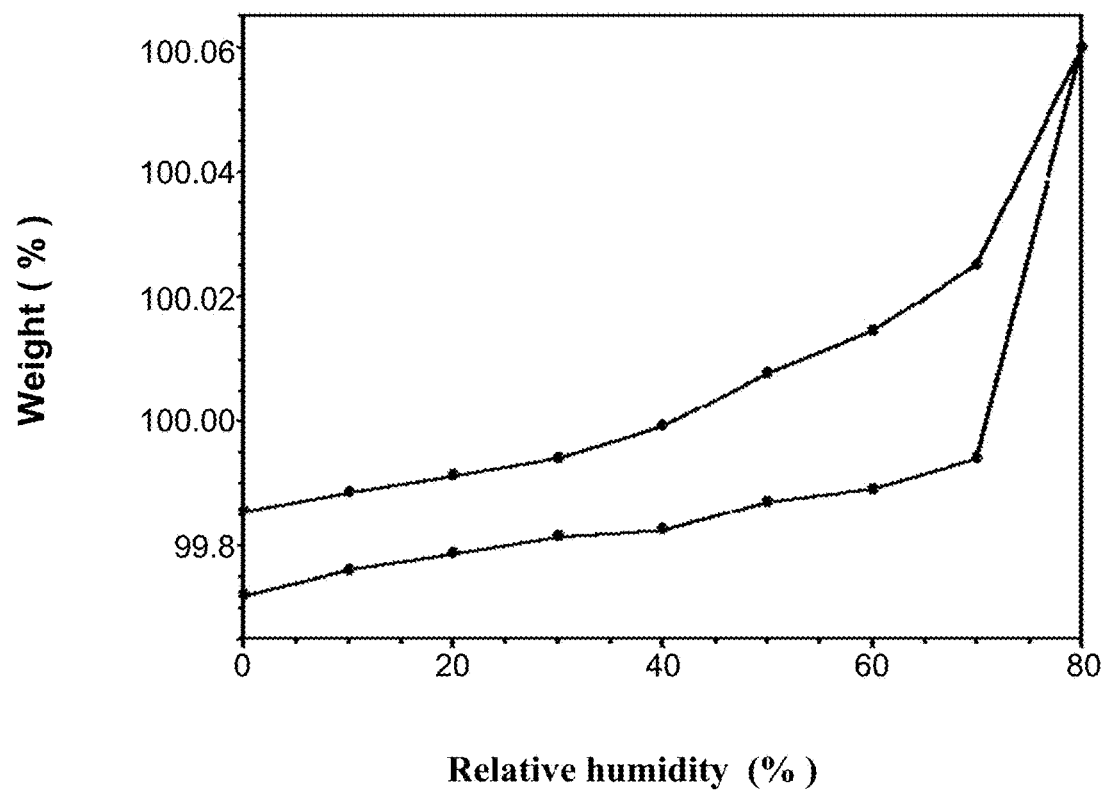
FIG. 36 is the isothermal sorption plot of lasmiditan hydrochloride Form C of the present invention.
Figure 37:
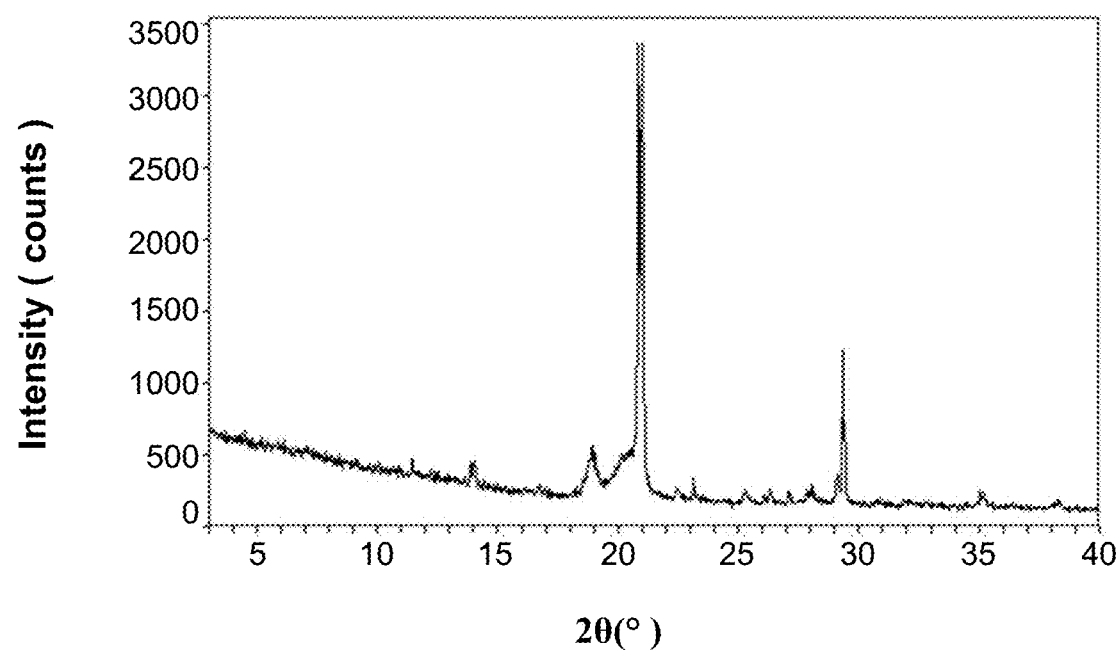
FIG. 37 is the XRPD pattern of lasmiditan hydrochloride Form E of the present invention.
Figure 38:
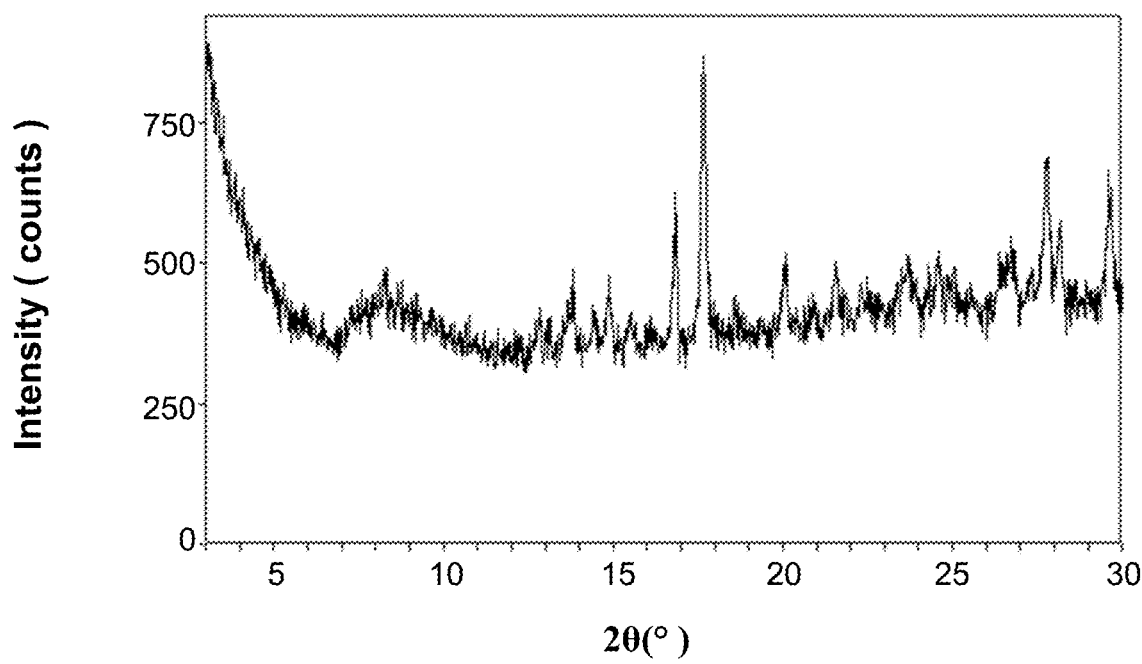
FIG. 38 is the XRPD pattern of lasmiditan hydrochloride Form G of the present invention.

Fifty milligrams of lasmiditan hydrochloride of Preparation Example 2 was dissolved in water-isopropanol solution (2.0 mL) containing 10% water at 50° C. to form a solution, which was volatilized to dryness at room temperature to obtain lasmiditan hydrochloride Form C (40 mg, 77% yield).
The XRPD pattern is shown in FIG. 32.
The DSC pattern is shown in FIG. 33.
The TGA pattern is shown in FIG. 34.
The PLM pattern is shown in FIG. 35.
The isothermal sorption plot is shown in FIG. 36.

Example 33

Fifty milligrams of lasmiditan hydrochloride of Preparation Example 2 was dissolved in water-trifluoroethanol solution (1.0 mL) containing 2% water at 60° C. to form a solution, which was volatilized to dryness at room temperature to obtain lasmiditan hydrochloride Form C (38 mg, 73% yield).

Example 34

Fifty milligrams of lasmiditan hydrochloride of Preparation Example 2 was dissolved in of water-saturated n-butanol (5 mL) at 55° C. to form a solution, which was volatilized to dryness at room temperature to obtain lasmiditan hydrochloride Form C (43 mg, 82% yield).

Example 35

Fifty milligrams of the lasmiditan hydrochloride of Preparation Example 2 was dissolved in water-saturated sec-butanol (5 mL) at 60° C. to form a solution, which was volatilized to dryness at room temperature to obtain lasmiditan hydrochloride Form C (41 mg, 79% yield).

Example 36

One hundred milligrams of lasmiditan hydrochloride of Preparation Example 2 was dissolved in water-acetone solution (2.0 mL) containing 2% water at 55° C. to form a solution, which was cooled to and kept at 4° C. for 3 days for crystallization, then filtered, and the solid was vacuum-dried 5 h at room temperature to obtain lasmiditan hydrochloride Form C (60 mg, 57% yield).

Example 37

Fifty milligrams of lasmiditan hydrochloride of Preparation Example 2 was dissolved in water-acetone solution (2.0 mL) containing 5% water at 60° C. to form a solution, which was cooled to and kept at 4° C. for 7 days for crystallization, then filtered, and the solid was vacuum-dried 12 h at 10° C. to obtain lasmiditan hydrochloride Form C (26 mg, 71% yield).

Example 38

Fifty milligrams of lasmiditan hydrochloride of Preparation Example 2 was dissolved in water-acetone solution (2.0 mL) containing 2% water at 60° C. to form a solution, which was cooled to and kept at 4° C. for 1 day for crystallization, then filtered, and the solid was vacuum-dried 1 h at 40° C. to obtain lasmiditan hydrochloride Form C (16 mg, 30% yield).

The samples prepared in Examples 33-38 have the same or similar XRPD patterns, PLM patterns, DSC patterns, TGA patterns (not shown) as those of the sample of Example 32, indicating that the samples of Examples 33-38 and the sample of Example 32 have the same crystalline form.

Example 39

| Component | Dosage (mg) |
|---|---|
| Lasmiditan Form 1 (Form 2 or Form 3 or lasmiditan hydrochloride Form A or Form B or Form C) (based on the active ingredient) | 100 |
| Starch | 235 |
| Magnesium stearate | 5 |
| Total | 340 |

Lasilmidan Form 1 (lasmiditan Form 2 or lasmiditan Form 3 or lasmiditan hydrochloride Form A or Form B or Form C), starch and magnesium stearate were mixed and filled into the capsule.

Example 40

| Component | Dosage (mg) |
|---|---|
| Lasmiditan Form 1 (Form 2 or Form 3 or lasmiditan hydrochloride Form A or Form B or Form C) (based on the active ingredient) | 50 |
| Microcrystalline cellulose | 175 |
| Silica colloid | 10 |
| Stearic acid | 5 |
| Total | 240 |

Lasmiditan Form 1 (Form 2 or Form 3 or lasmiditan hydrochloride Form A or Form B or Form C), microcrystalline cellulose, silica colloid, and stearic acid were mixed and compressed into tablets.

Example 41

| Component | Dosage (mg) |
|---|---|
| Lasmiditan Form 1 (Form 2 or Form 3 or lasmiditan hydrochloride Form A or Form B or Form C) (based on the active ingredient) | 200 |
| Microcrystalline cellulose | 270 |
| Silica colloid | 20 |
| Stearic acid | 10 |
| Total | 500 |

Lasmiditan Form 1 (lasmiditan Form 2 or Form 3 or lasmiditan hydrochloride Form A or Form B or Form C), microcrystalline cellulose, silica colloid, and stearic acid were mixed and compressed into tablets.

Comparative Example 1

Solid state stability experiment: Placed 20 mg of each of lasmiditan amorphous form of preparation Example 1, lasmiditan hydrochloride amorphous of Preparation Example 2, lasmiditan Form 1, lasmiditan Form 2, lasmiditan Form 3, lasmiditan hydrochloride Form A, lasmiditan hydrochloride Form B, lasmiditan hydrochloride Form C, and lasmiditan hydrochloride Form E of the present invention at room temperature under dry condition, took the samples out and analyzed by XRD at the corresponding time, their XRD pattern are shown in FIGS. 16-18 and FIGS. 46-50.

| Form | 1 day test results | 10 days test results |
|---|---|---|
| Lasmiditan amorphous form | Change to crystalline state | Not analyzed |
| Lasmiditan Form 1 | Form 1 | Form 1 |
| Lasmiditan Form 2 | Form 2 | Form 2 |
| Lasmiditan Form 3 | Form 3 | Form 3 |
| Lasmiditan hydrochloride amorphous form | Change to crystalline state | Not analyzed |
| Lasmiditan hydrochloride Form A | Form A | Form A |
| Lasmiditan hydrochloride Form B | Form B | Form B |
| Lasmiditan hydrochloride Form C | Form C | Form C |
| Lasmiditan hydrochloride Form E | Change to Form A | Not analyzed |

The results showed that lasmiditan amorphous form began to crystallize after having been placed for 1 day; lasmiditan hydrochloride amorphous form began to crystallize after having been placed for 1 day; lasmiditan hydrochloride Form E converted to Form A after having been placed for 1 day; and lasmiditan Form 1, Form 2, Form 3, and lasmiditan hydrochloride Form A, Form B, and Form C of the present invention still remained their original forms after having been placed for 10 days. It indicates that lasmiditan Form 1, Form 2, Form 3 and lasmiditan hydrochloride Form A, Form B and Form C of the present invention have better solid state stability than the prior art.

Comparative Example 2

Chemical stability experiment: Placed 20 mg of each of lasmiditan amorphous of Preparation Example 1, lasmiditan hydrochloride amorphous of Preparation Example 2, lasmiditan Form 1, lasmiditan Form 2, lasmiditan Form 3, lasmiditan hydrochloride Form A, lasmiditan hydrochloride Form B, lasmiditan hydrochloride Form C of the present invention at 40° C. under dry conditions for 10 days, then analyzed the purity of samples by HPLC. The results are shown in the following Table:

| Lasmiditan | Purity (%) 1 day | Purity (%) 10 days | Lasmiditan hydrochloride | Purity (%) 1 day | Purity (%) 10 days |
|---|---|---|---|---|---|
| Amorphous | 99.65 | 97.22 | Amorphous | 99.34 | 97.67 |
| Form 1 | 99.63 | 99.64 | Form A | 99.02 | 99.05 |
| Form 2 | 99.64 | 99.62 | Form B | 99.15 | 99.24 |
| Form 3 | 99.24 | 99.23 | Form C | 99.73 | 99.65 |

The results showed that after having been placed for 10 days, the chemical purity of lasmiditan amorphous was reduced more than 2%, and the chemical purity of lasmiditan hydrochloride amorphous was reduced more than 1.5%. Lasmiditan Form 1, Form 2, Form 3, lasmiditan hydrochloride Form A, Form B, and Form C of the present invention still maintained their original purity. It Indicated that lasmiditan Form 1, Form 2, Form 3 and lasmiditan hydrochloride Form A, Form B and Form C of the present invention have better chemical stability than the prior art.

The invention claimed is:

1. Lasmiditan Form 1 having the structure shown in formula (I) below,

(I)

wherein, measured using Cu-Kα radiation, the X-ray powder diffraction pattern of the lasmiditan Form 1, expressed as 2θ angles, has the following characteristic peaks: 5.3±0.2°, 12.5±0.2°, 13.3±0.2°, 15.2±0.2°, 16.6±0.2° and 19.8±0.2°.

2. The lasmiditan Form 1 according to claim 1, wherein the X-ray powder diffraction pattern of the lasmiditan Form 1, expressed as 2θ angles, has the following characteristic peaks: 5.0±0.2°, 5.3±0.2°, 7.2±0.2°, 10.1±0.2°, 12.5±0.2°, 13.3±0.2°, 14.9±0.2°, 15.2±0.2°, 16.6±0.2°, 19.8±0.2°, 21.7±0.2° and 22.4±0.2°.

3. The lasmiditan Form 1 according to claim 2, wherein the X-ray powder diffraction pattern of the lasmiditan Form 1, expressed as 2θ angles, has the following characteristic peaks and relative intensity:

| 2θ | Relative intensity % (I) |
|---|---|
| 5.0 ± 0.2° | 50.0 |
| 5.3 ± 0.2° | 96.2 |
| 7.2 ± 0.2° | 37.4 |
| 10.1 ± 0.2° | 52.9 |
| 10.7 ± 0.2° | 31.7 |
| 12.5 ± 0.2° | 62.0 |
| 13.3 ± 0.2° | 81.1 |
| 14.9 ± 0.2° | 77.3 |
| 15.2 ± 0.2° | 89.5 |
| 15.9 ± 0.2° | 46.2 |
| 16.6 ± 0.2° | 100.0 |
| 18.6 ± 0.2° | 39.9 |
| 19.8 ± 0.2° | 59.7 |
| 21.7 ± 0.2° | 26.1 |
| 22.4 ± 0.2° | 60.5 |
| 22.8 ± 0.2° | 46.2 |
| 24.0 ± 0.2° | 49.4 |
| 24.5 ± 0.2° | 29.0 |
| 25.5 ± 0.2° | 41.2. |

4. A method of preparing the lasmiditan Form 1 according to claim 1, comprising any one of the following methods:
1) dissolving lasmiditan free base in a mixed solvent to form a solution, volatilizing the solution to dryness to obtain the lasmiditan Form 1; the mixed solvent is a mixture of water and a water-miscible organic solvent; wherein:
the mixed solvent is a water-methanol mixture, water-acetone mixture or water-acetonitrile mixture;
the mass to volume ratio of lasmiditan to the mixed solvent is from 50 to 500 mg: 1 mL;
the volume percentage of water in the mixed solvent is from 1% to 10%; and
the volatilization is carried out at room temperature;
2) forming a suspension of lasmiditan free base in a solvent, stirring for crystallization, separating the crystals, and then drying to obtain the lasmiditan Form 1; the solvent is selected from solvents containing water; wherein:
the solvent is water, a mixed solvent of ethanol and water, a mixed solvent of tetrahydrofuran and water or ethyl acetate saturated with water;

the volume percentage of water in the solvent is from 1% to 100%;
the mass to volume ratio of lasmiditan to the solvent is from 10 to 1000 mg: 1 mL;
the stirring time is from 0.5 hours to 3 days; and
the stirring is carried out at room temperature.

5. Lasmiditan Form 2 having the structure shown in formula (I) below,

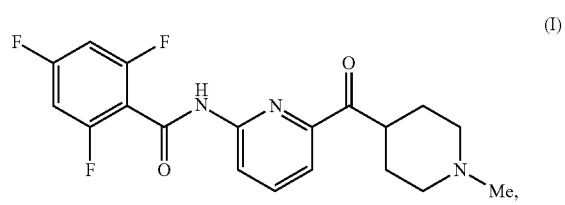

(I)

wherein, measured using Cu-Kα radiation, the X-ray powder diffraction pattern of the lasmiditan Form 2, expressed as 2θ angles, has the following characteristic peaks: 4.9±0.2°, 9.0±0.2°, 9.8±0.2°, 13.5±0.2°, 15.8±0.2° and 17.7±0.2°.

6. The lasmiditan Form 2 according to claim 5, wherein the X-ray powder diffraction pattern of the lasmiditan Form 2, expressed as 2θ angles, has the following characteristic peaks: 4.9±0.2°, 9.0±0.2°, 9.8±0.2°, 12.9±0.2°, 13.5±0.2°, 15.8±0.2°, 17.7±0.2°, 18.5±0.2°, 19.7±0.2°, 22.2±0.2°, 22.7±0.2° and 23.7±0.2°.

7. The lasmiditan Form 2 according to claim 6, wherein the X-ray powder diffraction pattern of the lasmiditan Form 2, expressed as 2θ angles, has the following characteristic peaks the relative intensity:

| 2θ | Relative intensity % (I) |
|---|---|
| 4.9 ± 0.2° | 60.9 |
| 9.0 ± 0.2° | 44.5 |
| 9.8 ± 0.2° | 49.7 |
| 12.9 ± 0.2° | 27.7 |
| 13.5 ± 0.2° | 100.0 |
| 14.9 ± 0.2° | 20.8 |
| 15.8 ± 0.2° | 77.1 |
| 17.7 ± 0.2° | 87.8 |
| 18.2 ± 0.2° | 37.9 |
| 18.5 ± 0.2° | 69.2 |
| 19.3 ± 0.2° | 18.7 |
| 19.7 ± 0.2° | 59.9 |
| 20.5 ± 0.2° | 34.7 |
| 21.7 ± 0.2° | 31.0 |
| 22.2 ± 0.2° | 55.5 |
| 22.7 ± 0.2° | 51.7 |
| 23.3 ± 0.2° | 24.6 |
| 23.7 ± 0.2° | 52.4 |
| 25.2 ± 0.2° | 28.1 |
| 26.8 ± 0.2° | 18.8. |

8. A method of preparing the lasmiditan Form 2 according to claim 5, comprising the steps as below: forming a suspension of lasmiditan free base in a solvent, then stirring for crystallization, separating the crystals, and drying to obtain the lasmiditan Form 2; wherein:
the solvent is selected from the group consisting of $C_4$ to $C_6$ ether, $C_3$ to $C_5$ ketone, $C_1$ to $C_4$ alcohol, $C_2$ to $C_6$ ester, and $C_6$ to $C_8$ alkane;
the mass to volume ratio of lasmiditan to the solvent is 10 to 1000 mg: 1 mL;
the stirring time is 1 to 7 days; and
the stirring is carried out at room temperature.

9. Lasmiditan Form 3 having the structure shown in formula (I) below,

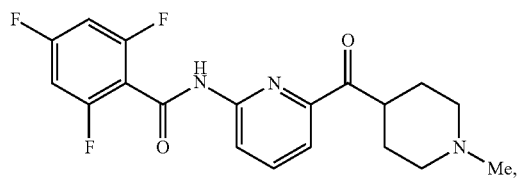

wherein, measured using Cu-Kα radiation, the X-ray powder diffraction pattern of the Form 3, expressed as 2θ angles, has the following characteristic peaks: 3.8±0.2°, 9.8±0.2°, 11.2±0.2°, 14.6±0.2°, 16.1±0.2° and 18.5±0.2°.

10. The lasmiditan Form 3 according to claim 9, wherein the X-ray powder diffraction pattern of the lasmiditan Form 3, expressed as 2θ angles, has the following characteristic peaks: 11.2±0.2°, 14.6±0.2°, 16.1±0.2°, 17.8±0.2°, 18.5±0.2°, 19.6±0.2°, 20.7±0.2°, 22.3±0.2°, 23.9±0.2° and 24.5±0.2°.

11. The lasmiditan Form 3 according to claim 10, wherein the X-ray powder diffraction pattern of the lasmiditan Form 3, expressed as 2θ angles, has the following characteristic peaks and their relative intensity:

| 2θ | Relative intensity % (I) |
|---|---|
| 3.8 ± 0.2° | 100.0 |
| 5.0 ± 0.2° | 5.3 |
| 7.5 ± 0.2° | 4.0 |
| 9.8 ± 0.2° | 10.2 |
| 11.2 ± 0.2° | 15.4 |
| 12.8 ± 0.2° | 4.6 |
| 13.6 ± 0.2° | 4.4 |
| 14.6 ± 0.2° | 12.4 |
| 16.1 ± 0.2° | 26.0 |
| 17.1 ± 0.2° | 4.9 |
| 17.8 ± 0.2° | 9.2 |
| 18.5 ± 0.2° | 23.0 |
| 18.9 ± 0.2° | 5.1 |
| 19.6 ± 0.2° | 11.6 |
| 20.7 ± 0.2° | 6.6 |
| 21.6 ± 0.2° | 5.5 |
| 22.3 ± 0.2° | 13.3 |
| 23.0 ± 0.2° | 8.5 |
| 23.9 ± 9.2° | 8.7 |
| 24.5 ± 9.2° | 16.5. |

12. A method of preparing the lasmiditan Form 3 according to claim 9, comprising any one of the following methods:
1) dissolving lasmiditan free base in a solvent to form a solution, then adding 1 to 10% (wt %) of polyethylene glycol 4000, applying ultrasound to facilitate dissolution, and volatilizing to dryness to obtain the lasmiditan Form 3; wherein:
the solvent is a $C_1$ to $C_4$ alcohol;
the mass ratio of lasmiditan to solvent is 50 to 100 mg: 1 mL; and
the volatilization process is carried out at 40° C.;
2) dissolving lasmiditan free base in a solvent to form a solution, and volatilizing to dryness to obtain the lasmiditan Form 3; wherein:
the solvent is selected from the group consisting of isopropyl ether, isopropyl acetate and toluene;

the mass to volume ratio of lasmiditan to the solvent is 2 to 50 mg: 1 mL; and
the volatilization process is carried out at room temperature.

13. Lasmiditan hydrochloride Form A having the structure shown in formula (II) below,

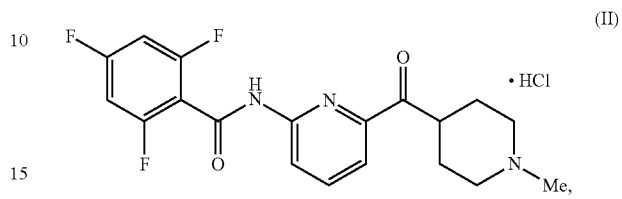

wherein, measured using Cu-Kα radiation, the X-ray powder diffraction pattern of the Form A, expressed as 2θ angles, has the following characteristic peaks: 12.1±0.2°, 13.1±0.2°, 15.8±0.2°, 18.9±0.2°, 19.8±0.2° and 25.3±0.2°.

14. The lasmiditan hydrochloride Form A according to claim 13, wherein the X-ray powder diffraction pattern of the lasmiditan hydrochloride Form A, expressed as 2θ angles, has the following characteristic peaks: 9.3±0.2°, 12.1±0.2°, 13.1±0.2°, 15.8±0.2°, 18.9±0.2°, 19.8±0.2°, 21.0±0.2°, 22.0±0.2°, 23.5±0.2°, 25.3±0.2°, 27.3±0.2° and 27.6±0.2°.

15. The lasmiditan hydrochloride Form A according to claim 14, wherein the X-ray powder diffraction pattern of the lasmiditan hydrochloride Form A, expressed as 2θ angles, has the following characteristic peaks and their relative intensity:

| 2θ | Relative intensity % (I) |
|---|---|
| 9.3 ± 0.2° | 1.9 |
| 12.1 ± 0.2° | 3.3 |
| 13.1 ± 0.2° | 11.3 |
| 15.8 ± 0.2° | 2.0 |
| 18.9 ± 0.2° | 100.0 |
| 19.8 ± 0.2° | 2.6 |
| 20.8 ± 0.2° | 2.5 |
| 21.0 ± 0.2° | 3.4 |
| 22.0 ± 0.2° | 1.9 |
| 23.5 ± 0.2° | 5.8 |
| 25.3 ± 0.2° | 11.7 |
| 25.8 ± 0.2° | 3.2 |
| 27.3 ± 0.2° | 3.6 |
| 27.6 ± 0.2° | 5.1. |

16. A method of preparing the lasmiditan hydrochloride Form A according to claim 13, comprising any one of the following methods:
1) dissolving lasmiditan hydrochloride in a solvent to form a solution, and volatilizing to dryness to obtain the lasmiditan hydrochloride Form A; wherein:
the solvent is selected from the group consisting of alcohol, nitromethane, dichloromethane, 1,4-dioxane, acetonitrile and a mixture thereof;
the mass to volume ratio of lasmiditan hydrochloride to solvent is 5 to 25 mg: 1 mL; and
the volatilization process is carried out at room temperature;
2) placing lasmiditan hydrochloride in a solvent to form a suspension, stirring for crystallization, separating the crystals, and drying to obtain the lasmiditan hydrochloride Form A; wherein:

the solvent is selected from the group consisting of alcohol, ether, ester, ketone, alkane, tetrahydrofuran, 1,4-dioxane, toluene and a mixture thereof;
the mass ratio of the lasmiditan hydrochloride to the solvent is 50 to 200 mg: 1 mL;
the stirring time is from 1 day to 7 days and the stirring process is carried out at room temperature.

17. Lasmiditan hydrochloride Form B having the structure shown in formula (III) below,

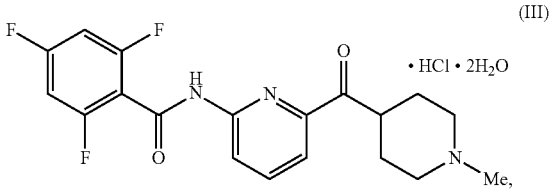 [SMILES: CN1CCC(C(=O)c2cccc(NC(=O)c3c(F)cc(F)cc3F)n2)CC1]

(III)

wherein the lasmiditan hydrochloride Form B is a dihydrate, and wherein, measured using Cu-Kα radiation, the X-ray powder diffraction pattern of the lasmiditan hydrochloride Form B, expressed as 2θ angles, has the following characteristic peaks: 14.3±0.2°, 15.6±0.2°, 23.8±0.2°, 29.5±0.2°.

18. The lasmiditan hydrochloride Form B according to claim 17, wherein the X-ray powder diffraction pattern of the lasmiditan hydrochloride Form B, expressed as 2θ angles, has the following characteristic peaks: 14.3±0.2°, 15.6±0.2°, 18.7±0.2°, 19.3±0.2°, 21.9±0.2°, 23.8±0.2°, 26.0±0.2°, 28.3±0.2°, 29.5±0.2°, 31.4±0.2°, 32.8±0.2° and 38.2±0.2°.

19. The lasmiditan hydrochloride Form B according to claim 18, wherein the X-ray powder diffraction pattern of the lasmiditan hydrochloride Form B, expressed as 2θ angles, has the following characteristic peaks and their relative intensity:

| 2θ | Relative intensity % (I) |
| --- | --- |
| 14.3 ± 0.2° | 100.0 |
| 15.6 ± 0.2° | 76.1 |
| 17.0 ± 0.2° | 7.0 |
| 18.7 ± 0.2° | 20.1 |
| 19.3 ± 0.2° | 19.9 |
| 21.7 ± 0.2° | 8.0 |
| 21.9 ± 0.2° | 10.7 |
| 23.8 ± 0.2° | 70.1 |
| 24.4 ± 0.2° | 12.7 |
| 26.0 ± 0.2° | 27.3 |
| 27.7 ± 0.2° | 6.3 |
| 28.3 ± 0.2° | 10.5 |
| 29.0 ± 0.2° | 10.9 |
| 29.5 ± 0.2° | 54.3 |
| 30.3 ± 0.2° | 12.3 |
| 31.4 ± 0.2° | 17.9 |
| 32.8 ± 0.2° | 36.4 |
| 38.2 ± 0.2° | 44.9. |

20. A method of preparing the lasmiditan hydrochloride Form B according to claim 17, comprising any one of the following methods:
1) dissolving lasmiditan hydrochloride in a solvent to form a solution, cooling for crystallization, separating the crystalline form and drying to obtain the lasmiditan hydrochloride Form B; wherein:
the solvent is a mixed solvent containing water;
the volume percentage of water in the mixed solvent is 40% to 100%;
the mass to volume ratio of lasmiditan hydrochloride to the solvent is 100 to 200 mg: 1 mL;
the crystallization time is 3 to 5 days, the crystallization temperature is lower than the temperature of forming the solution;
the drying temperature is from 10° C. to 40° C.; and
the drying time is from 1 to 12 hours;
2) dissolving lasmiditan hydrochloride in a solvent to form a solution, and volatilizing to dryness to obtain the lasmiditan hydrochloride Form B; wherein:
the solvent is a mixed solvent containing water;
the volume percentage of water in the mixed solvent is 40% to 100%;
the mass to volume ratio of lasmiditan hydrochloride to the solvent is 100 to 150 mg: 1 mL; and
the volatilization process is carried out at room temperature.

21. Lasmiditan hydrochloride Form C having the structure shown in formula (IV) below,

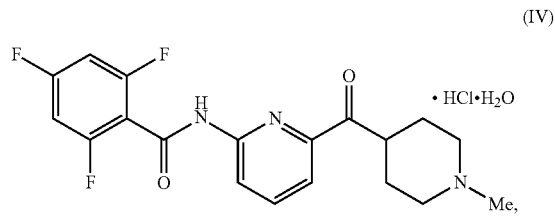

(IV)

wherein the lasmiditan hydrochloride Form C is a monohydrate, and wherein, measured using Cu-Kα radiation, the X-ray powder diffraction pattern of the lasmiditan hydrochloride Form C, expressed as 2θ angles, has the following characteristic peaks: 13.1±0.2°, 13.8±0.2°, 14.9±0.2°, 16.6±0.2°, 18.0±0.2° and 22.2±0.2°.

22. The lasmiditan hydrochloride Form C according to claim 21, wherein the X-ray powder diffraction pattern of the lasmiditan hydrochloride Form C, expressed as 2θ angles, has the following characteristic peaks: 13.1±0.2°, 13.8±0.2°, 14.9±0.2°, 16.6±0.2°, 17.7±0.2°, 18.0±0.2°, 19.6±0.2°, 20.4±0.2°, 21.6±0.2°, 22.2±0.2°, 24.6±0.2° and 27.5±0.2°.

23. The lasmiditan hydrochloride Form C according to claim 22, wherein the X-ray powder diffraction pattern of the lasmiditan hydrochloride Form C, expressed as 2θ angles, has the following characteristic peaks and their relative intensity:

| 2θ | Relative intensity % (I) |
| --- | --- |
| 8.9 ± 0.2° | 5.0 |
| 13.1 ± 0.2° | 40.4 |
| 13.8 ± 0.2° | 45.8 |
| 14.9 ± 0.2° | 11.5 |
| 16.6 ± 0.2° | 100.0 |
| 17.0 ± 0.2° | 5.6 |
| 17.7 ± 0.2° | 13.8 |
| 18.0 ± 0.2° | 33.2 |
| 19.1 ± 0.2° | 4.3 |
| 19.6 ± 0.2° | 11.6 |
| 20.4 ± 0.2° | 8.4 |
| 21.6 ± 0.2° | 11.7 |
| 22.2 ± 0.2° | 32.9 |
| 24.6 ± 0.2° | 7.7 |
| 25.9 ± 0.2° | 9.9 |
| 26.7 ± 0.2° | 5.9 |

-continued

| 2θ | Relative intensity % (I) |
|---|---|
| 27.5 ± 0.2° | 12.7 |
| 28.3 ± 0.2° | 11 |
| 29.1 ± 0.2° | 5.2 |
| 31.1 ± 0.2° | 7.1. |

24. A method of preparing the lasmiditan hydrochloride Form C according to claim 21, comprising any one of the following methods:
1) dissolving lasmiditan hydrochloride in a solvent to form a solution, and volatilizing to dryness to obtain the lasmiditan hydrochloride Form C; wherein:
the solvent is selected from the group consisting of a mixed solvent of trifluoroethanol and water, a mixed solvent of isopropyl alcohol and water, water-saturated n-butanol, and water-saturated 2-butanol;
the volume percentage of water in the mixed solvent is 2% to 10%;
the mass to volume ratio of lasmiditan hydrochloride to the solvent is 10 to 50 mg: 1 mL; and
the volatilization process is carried out at room temperature;
2) dissolving lasmiditan hydrochloride in a solvent to form a solution, cooling the solution for crystallization, separating the crystals and drying to obtain the lasmiditan hydrochloride Form C; wherein:
the solvent is a mixed solvent of water and acetone;
the volume percentage of water in the mixed solvent is 2% to 5%;
the mass ratio of lasmiditan hydrochloride to the solvent is 25 to 50 mg: 1 mL;
the crystallization time is 1 to 7 days;
the crystallization temperature is lower than the temperature of forming the solution;
the drying temperature is from 10° C. to 40° C.; and
the drying time is from 1 to 12 hours.

25. A pharmaceutical composition comprising a therapeutically and/or preventively effective amount of the lasmiditan Form 1 according to claim 1, and at least one pharmaceutically acceptable carrier.

26. A pharmaceutical composition comprising a therapeutically and/or preventively effective amount of the lasmiditan Form 2 according to claim 5, and at least one pharmaceutically acceptable carrier.

27. A pharmaceutical composition comprising a therapeutically and/or preventively effective amount of the lasmiditan Form A according to claim 13, and at least one pharmaceutically acceptable carrier.

28. A pharmaceutical composition comprising a therapeutically and/or preventively effective amount of the lasmiditan Form C according to claim 21, and at least one pharmaceutically acceptable carrier.

* * * * *